United States Patent
Breddam et al.

(10) Patent No.: US 7,420,105 B2
(45) Date of Patent: Sep. 2, 2008

(54) BARLEY FOR PRODUCTION OF FLAVOR-STABLE BEVERAGE

(75) Inventors: Klaus Breddam, Roskilde (DK); Ole Olsen, Copenhagen S (DK); Birgitte Skadhauge, Birkerod (DK); Finn Lok, Valby (DK); Soren Knudsen, Malov (DK); Lene Molskov Bech, Smorum (DK)

(73) Assignee: Carlsberg A/S, Copenhagen (DK)

( * ) Notice: Subject to any disclaimer, the term of this patent is extended or adjusted under 35 U.S.C. 154(b) by 437 days.

(21) Appl. No.: 10/800,200

(22) Filed: Mar. 11, 2004

(65) Prior Publication Data

US 2005/0204437 A1 Sep. 15, 2005

(51) Int. Cl.
- *A01H 5/00* (2006.01)
- *C12N 15/82* (2006.01)
- *C12C 1/00* (2006.01)
- *C12C 11/00* (2006.01)

(52) U.S. Cl. .................. 800/320; 800/298; 800/278; 435/184; 435/185; 426/11; 426/64

(58) Field of Classification Search .................. 800/320
See application file for complete search history.

(56) References Cited

U.S. PATENT DOCUMENTS

| | | | |
|---|---|---|---|
| 4,683,195 A | 7/1987 | Mullis et al. | |
| 4,800,159 A | 1/1989 | Mullis et al. | |
| 5,283,184 A | 2/1994 | Jorgensen et al. | |
| 5,942,661 A | 8/1999 | Keller | |
| 6,008,034 A | 12/1999 | Häusler et al. | |
| 6,150,145 A | 11/2000 | Häusler et al. | |
| 6,274,358 B1 | 8/2001 | Holtz et al. | |
| 6,355,862 B1 | 3/2002 | Handa et al. | |
| 6,660,915 B2 * | 12/2003 | Douma et al. | 800/320 |
| 2003/0074693 A1 | 4/2003 | Cahoon et al. | |
| 2003/0167544 A1 | 9/2003 | Douma et al. | |

FOREIGN PATENT DOCUMENTS

| | | |
|---|---|---|
| EP | 1 609 866 | 12/2005 |
| WO | WO 02/053720 | 7/2002 |
| WO | WO 02/053721 A1 | 7/2002 |
| WO | WO 2004/085652 | 10/2004 |

OTHER PUBLICATIONS

Hirota et al., Jun. 20-26 Jun. 2004, *9th International Barley Genetics Symposium*, Brno, Czech Republic, pp. 69-73. "Genetic Variation of Barley Seed Lipoxygenase-1: Null Mutants."

Alonso, J.M. et al., "Genome-wide insertional mutagenesis of *Arabidopsis thaliana*," *Science*, 301:653-657 (Aug. 1, 2003).

American Association of Cereal Chemists, "Approved methods of the American Association of Cereal Chemists," *ISBN*, 0-913250-86-4, 23 pages (1995).

American Society of Brewing Chemists, "Methods of analysis of the American Society of Brewing Chemists," *ISBN*, 1-881696-01-4, 10 pages (1992).

Anthon, G. E. and Barrett, D.M., "Colorimetric method for the determination of lipoxygenase activity," *J. Agric. Food Chem.*, 49:32-37 (2001).

Ashrafi, K. et al., "Genome-wide RNAi analysis of *Caenorhabditis elegans* fat regulatory genes," *Nature*, 421:268-272 (Jan. 16, 2003).

Auld, D.L. et al., "Rapeseed mutants with reduced levels of polyunsaturated fatty acids and increased levels of oleic acid," *Crop Sci.*, 32:657-662 (1992).

Axelrod, B. et al., "Lipoxygenase from soybeans," *Methods Enzymol.*, 71:441-451 (1981).

Bargmann, C.I., "High-throughput reverse genetics: RNAi screens in *Caenorhabditis elegans*," *Genome Biol. 2: Reviews*, 1005.1-1005.3 (Jan. 31, 2001).

Bell, E. et al., "A chloroplast lipoxygenase is required for wound-induced jasmonic acid accumulation in *Arabidopsis*," *Proc. Natl. Acad. Sci. USA*, 92:8675-8679 (Sep. 1995).

Bell, E. and Mullet, J.E., "Lipoxygenase gene expression is modulated in plants by water deficit, wounding, and methyl jasmonate," *Mol. Gen. Genet.*, 230:456-462 (1991).

Bell, E. and Mullet, J.E., "Characterization of an *Arabidopsis* lipoxygenase gene responsive to methyl jasmonate and wounding," *Plant Physiol.*, 103:1133-1137 (1993).

"Bios International,", *Data, Bios Intern.*, 4:38-42 (2001).

Blée, E. and Joyard, J., "Envelope membranes from spinach chloroplasts are a site of metabolism of fatty acid hydroperoxides," *Plant Physiol.*, 110:445-454 (1996).

Bohland, C. et al., "Differential induction of lipoxygenase isoforms in wheat upon treatment with rust fungus elicitor, chitin oligosaccharides, chitosan, and methyl jasmonate," *Plant Physiol.*, 114:679-685 (1997).

Burow, G.B. et al, "A peanut seed lipoxygenase responsive to *Aspergillus* colonization," *Plant Mol. Biol.*, 42:689-701 (2000).

Casey, R., "Lipoxygenases in the breadmaking process," In: "First European Symposium on Enzymes and Grain Processing." Angelino, S.A.G.F., van Hamer, R.J., Hartingsveldt, Heidekamp, F., van der Lugt, J.P., eds., pp. 188-194. TNO Nutrition and Food Research Institute, *ISBN*, 90-75202-04-0 (1997).

(Continued)

Primary Examiner—Medina A Ibrahim
(74) *Attorney, Agent, or Firm*—Merchant & Gould P.C.

(57) ABSTRACT

According to the invention, there is provided null-LOX-1 barley and plant products produced thereof, such as malt manufactured by using barley kernels defective in synthesis of the fatty acid-converting enzyme lipoxygenase-1. Said enzyme accounts for the principal activity related to conversion of linoleic acid into 9-hydroperoxy octadecadienoic acid, a lipoxygenase pathway metabolite, which—through further enzymatic or spontaneous reactions—may lead to the appearance of trans-2-nonenal. The invention enables brewers to produce a beer devoid of detectable trans-2-nonenal-specific off-flavors, even after prolonged storage of the beverage.

13 Claims, 28 Drawing Sheets

OTHER PUBLICATIONS

Figure 1A:
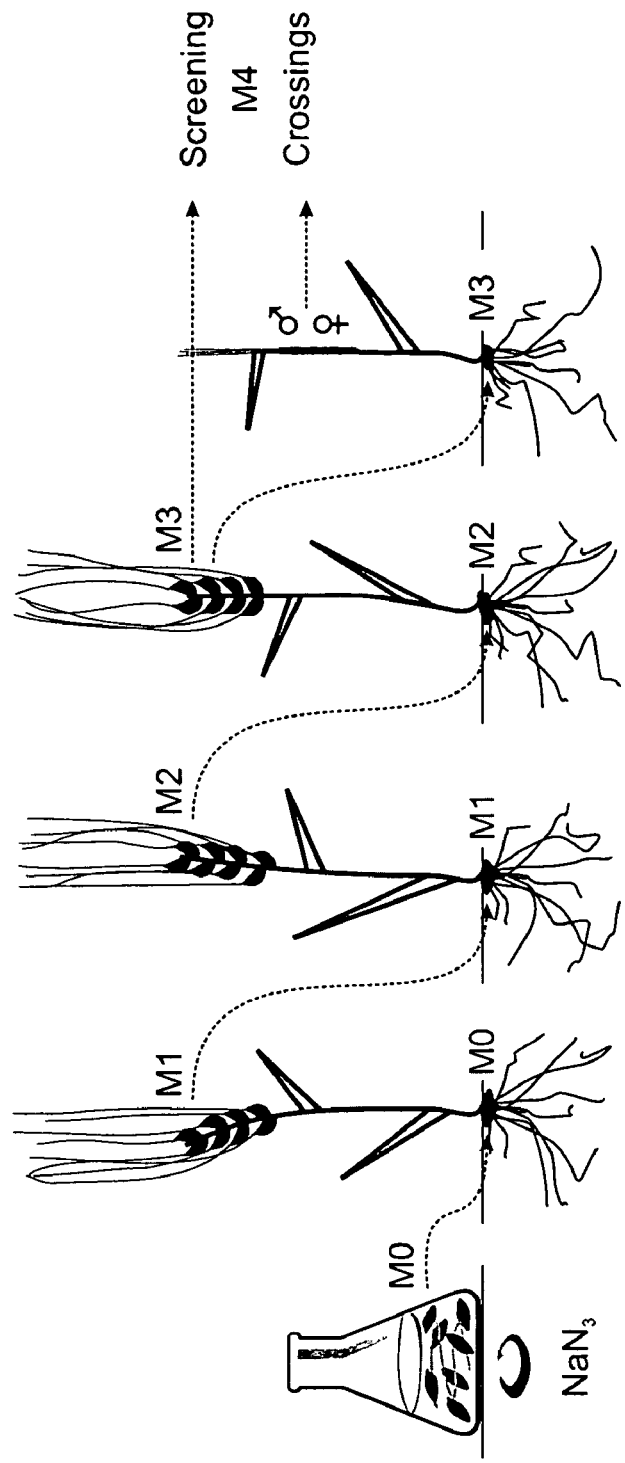

Christensen, A.H. et al., "Maize polyubiquitin genes: Structure, thermal perturbation of expression and transcript slicing, and promoter activity following transfer to protoplasts by electroporation," *Plant Mol. Biol.*, 18:675-689 (1992).

Colbert, T. et al., "High-throughput screening for induced point mutations," *Plant Physiol.*, 126:480-484 (Jun. 2001).

Cornish-Bowden, A., "Nomenclature for incompletely specified bases in nucleic acid sequences: Recommendations 1984," *Nucleic Acids Res.*, 13:3021-3030 (1985).

Croft, K.P.C. et al., "Volatile products of the lipoxygenase pathway evolved from *Phaseolus vulgaris* (L.) leaves inoculated with *Pseudomonas syringae* pv *phaseolicola*," *Plant Physiol.*, 101:13-24 (1993).

Davies, C.S. and Nielsen, N.C., "Genetic analysis of null-allele for lipoxygenase-2 in soybean," *Crop Sci.*, 26:460-463 (May-Jun. 1986).

Dougherty, W.G. and Parks, T.D., "Transgenes and gene suppression: Telling us something new!" *Curr. Opin. Cell Biol.*, 7:399-405 (1995).

Drost, B. W. et al., "Role of individual compounds in beer staling," *Tech. Q. MBAA*, 11:127-134 (1974).

Drost, B. W. et al., "Flavor stability," *J. Am. Soc. Brew. Chem.*, 48:124-131 (1990).

"EBC Analysis Committee, European Brewery Convention, "Analytica—EBC"," *ISBN*, 3-418-00759-7, 13 pages (1998).

Feussner, I. and Wasternack, C., "The lipoxygenase pathway," *Annu. Rev. Plant Biol.*, 53:275-297 (2002).

Forster, C. et al., "Molecular analysis of a null mutant for pea (*Pisum sativum* L.) seed lipoxygenase-2," *Plant Mol. Biol.*, 39:1209-1220 (1999).

Gardner, H.W. and Grove, M.J., "Method to produce (S)-hydroperoxides of linoleic and linolenic acids by maize lipoxygenase," *Lipids*, 36:529-533 (2001).

Glaever, G. et al., "Functional profiling of the *Saccharomyces cerevisiae* genome," *Nature*, 418:387-391 (Jul. 25, 2002).

Gönczy, P. et al., "Functional genomic analysis of cell division in *C. elegans* using RNAi of genes on chromosome III," *Nature*, 408:331-336 (Nov. 16, 2000).

Graef, G.L. et al., "Fatty acid development in a soybean mutant with high stearic acid," *J. Am. Oil Chem. Soc.*, 62:773-775 (Apr. 1985).

Griffiths, A. et al., "Fruit-specific lipoxygenase suppression in antisense-transgenic tomatoes," *Postharvest Biol. Technol.*, 17:163-173 (1999).

Gronqvist, A. et al., "Carbonyl compounds during beer production and in beer," *Proceedings of the 24th EBC Congress, Oslo*, pp. 421-428 (1993).

Grosch, W. and Schwartz, J.M., "Linoleic and linolenic acid as precursors of the cucumber flavor," *Lipids*, 6:351-352 (1971).

Hamberg, M., "Trihydroxyoctadecenoic acids in beer: Qualitative and quantitative analysis," *J. Agric. Food Chem.*, 39:1568-1572 (1991).

Hannon, G.J., "RNA interference," *Nature*, 418:244-251 (Jul. 11, 2002).

Hildebrand, D.F. and Hymowitz, t., "Inheritance of lipoxygenase-1 activity in soybean seeds," *Crop Sci.*, 22:851-853 (Jul.-Aug. 1982).

Holtman, W.L. et al., "Differential expression of lipoxygenase isoenzymes in embryos of germinating barley," *Plant Physiol.*, 111:569-576 (1996).

Hoseney, R.C., "An overview of malting and brewing," *Cereal Foods World*, 39:675-679 (Sep. 1994).

Husson, F. and Belin, J.M., "Purification of hydroperoxide lyase from green bell pepper (*Capsicum annuum* L.) fruits for the generation of C6-aldehydes in vitro," *J. Agric. Food Chem.*, 50:1991-1995 (Feb. 26, 2002).

The Analysis Committee of The Institute of Brewing, "Institute of Brewing. Methods of analysis," *ISBN*, 0-900489-10-3, 14 pages (1997).

IUPAC-IUB Joint Commission on Biochemical Nomenclature, "Nomenclature and symbolism for amino acids and peptides. Recommendations 1983," *Biochem. J.*, 219:345-373 (1984).

Isshiki, M. et al., "Nonsense-mediated decay of mutant *waxy* mRNA in rice," *Plant Physiol.*, 125:1388-1395 (Mar. 2001).

Jalloul, A. et al., Lipid peroxoidation in cotton: *Xanthomonas* interactions and the role of lipoxygenases during the hypersensitive reaction, *Plant J.*, 32:1-12 (2002).

Jamieson, A.M. and Van Gheluwe, J.E.A., "Identification of a compound responsible for cardboard flavor in beer," *Proc. Am. Soc. Brew. Chem.*, 29:192-197 (1970).

Jende-Strid, B., "Gene-enzyme relations in the pathway of flavonoid biosynthesis in barley," *Theor. Appl. Genet.*, 81:668-674 (1991).

Jende-Strid, B., "Genetic control of flavonoid biosynthesis in barley," *Hereditas*, 119:187-204 (1993).

Jensen, L.G. et al, "Transgenic barley expressing a protein-engineered, thermostable (1,3-1,4)-β-glucanase during germination," *Proc. Natl. Acad. Sci. USA* 93, 3487-3491 (Apr. 1996).

Kamath, R.S. et al., "Effectiveness of specific RNA—mediated interference through ingested double-stranded RNA in *Caenorhabdtis elegans*," *Genome Biol. 2: Research*, 0002.10 (Dec. 20, 2000).

Kamath, R.S. et al., "Systematic functional analysis of the *Caenorhabditis elegans* genome using RNAi," *Nature*, 421:231-237 (Jan. 2003).

Kitamura et al., "Genetic analysis of a null-allele for lipoxygenase-3 in soybean seeds," *Crop Sci.*, 23:924-927 (Oct. 1983).

Kleinhofs, A. et al., "Induction and selection of specific gene mutations in Hordeum and Pisum," *Mut. Res.*, 51:29-35 (1978).

Kolomiets, M.V. et al., "Lipoxygenase is involved in the control of potato tuber development," *Plant Cell*, 13:613-626 (Mar. 2001).

Kuroda et al., "Characterization of factors involved in the production of 2(E)-nonenal during mashing," *Biosci. Biotechnol. Biochem.*, 67:691-697 (2003).

Kusaba, M. et al., "*Low glutelin content1*: A dominant mutation that suppresses the *Glutelin* multigene family via RNA silencing in rice," *Plant Cell*, 15:1455-1467 (Jun. 2003).

Laemmli, U.K., "Cleavage of structural proteins during the assembly of the head of bacteriophage T4," *Nature*, 227:680-685 (Aug. 15, 1970).

León, J. et al., "Lipoxygenase H1 gene silencing reveals a specific role in supplying fatty acid hydroperoxides for aliphatic aldehyde production," *J. Biol. Chem.*, 277:416-423 (Jan. 4, 2002).

Lermusieau, G. et al., "Nonoxidative mechanism for development of trans-2-nonenal in beer," *J. Am. Soc. Brew. Chem.*, 57(1):29-33 (1999).

Liégeois, C. et al., "Release of deuterated (E)-2-nonenal during beer aging from labeled precursors synthesized before boiling," *J. Agric. Food Chem.*, 50:7634-7638 (2002) (web: Nov. 19, 2002).

Maquat, L.E. and Carmichael, G.G., "Quality control of mRNA function," *Cell*, 104:173-176 (Jan. 26, 2001).

Matsui, K. et al., "Effects of overexpression of fatty acid 9-hydroperoxide lyase in tomatoes (*Lycopersicon esculentum* Mill.)," *J. Agric. Food Chem.*, 49:5418-5424 (2001) (web: Oct. 27, 2001).

May, C. et al., "The N-terminal β-barrel structure of lipid body lipoxygenase mediates its bindings to liposomes and lipid bodies," *Eur. J. Biochem.*, 267:1100-1109 (2000).

McElroy, D. and Jacobsen, J., "Whats brewing in barley biotechnology?" *Bio/Technology*, 13:245-249 (Mar. 1995).

Meilgaard, M.C., "Flavor chemistry of beer: Part II: Flavor and threshold of 239 aroma volatiles," *Tech. Q. MBAA*, 12:151-168 (1975).

Melan, M.A. et al., "An *Arabidopsisthaliana* lipoxygenase gene can be induced by pathogens, abscisic acid, and methyl jasmonate," *Plant Physiol.*, 101:441-450 (1993).

Mendell, J.T. and Dietz, H.C., "When the message goes awry: Disease-producing mutations that influence mRNA content and performance," *Cell*, 107:411-414 (Nov. 16, 2001).

Narziss, L., "Centenary Review: Technological factors of flavour stability," *J. Inst. Brew.*, 92:346-353 (Jul.-Aug. 1986).

Noël, S. and Collin, S., "Trans-2-nonenal degradation products during mashing," *Eur. Brew. Conv. Proc. Congr. 25th*, Brussels: 483-490 (1995).

Noordermeer, M.A. et al., "Fatty acid hydroperoxide lyase: A plant cytochrome P450 enzyme involved in wound healing and pest resistance," *ChemBioChem*, 2:494-504 (2001).

Noordermeer, M.A. et al., "Development of a biocatalytic process for the production of C6-aldehydes from vegetable oils by soybean lipoxygenase and recombinant hydroperoxide lyase," *J. Agric. Food Chem.*, 50:4270-4274 (2002) (web: Jun. 21, 2002).

Norden, A.J. et al., "Variability in oil quality among peanut genotypes in the Florida breeding program," *Peanut Sci.*, 14:7-11 (1987).

Nyborg, M. et al., "Investigations of the protective mechanism of sulfite against beer staling and formation of adducts with *trans*-2-nonenal," *J. Am. Soc. Brew. Chem.*, 57:24-28 (1999).

Ohtsu, K. et al., "Flavor stability of packaged beer in relation to the oxidation of wort," *Brew. Dig.*, 61(6):18-23 (Jun. 1986).

Olsen, O. et al., "Sodium azide mutagenesis: Preferential generation of A•T→G•C transitions in the barley *Ant*18 gene," *Proc. Natl. Acad. Sci. USA*, 90:8043-8047 (Sep. 1993).

Osorio, J. et al., "Mutant sunflowers with high concentration of saturated fatty acids in the oil," *Crop Sci.*, 35:739-742 (May-Jun. 1995).

Parinov, S. and Sundaresan, V., "Functional genomics in Arabidopsis: Large-scale insertional mutagenesis complements the genome sequencing project," *Curr. Opin. Biotechnol.*, 11:157-161 (2000).

Phillips, D.R. and Galliard, T., "Flavour biogenesis, partial purification and properties of a fatty acid hydroperoxide cleaving enzyme from fruits of cucumber," *Phytochemistry*, 17:355-358 (1978).

Ramezanzadeh, F.M. et al., "Prevention of oxidative rancidity in rice bran during storage," *J. Agric. Food Chem.*, 47:2997-3000 (1999) (web: Jul. 15, 1999).

Rancé, I. et al., "The incompatible interaction between *Phytophthora parasitica* var. *nicotianae* race 0 and tobacco is suppressed in transgenic plants expressing antisense lipoxygenase sequences," *Proc. Natl. Acad. Sci. USA*, 95:6554-6559 (May 1998).

Rasmussen, S.K. and Hatzack, F., "Indentification of two low-phytate barley (*Hordeum vulgare* L.) grain mutants by TLC and genetic analysis," *Hereditas*, 129:107-112 (1998).

Rogers, K.R. et al., "Lipid peroxidation is a consequence of elicitor activity," *Plant Physiol.*, 86:547-533 (1988).

Rouster, J. et al., "Identification of a methyl jasmonate-responsive region in the promoter of a lipoxygenase I gene expressed in barley grain," *Plant J.*, 11:513-523 (1997).

Royo, J. et al., "Antisense-mediated depletion of a potato lipoxygenase reduces wound induction of proteinase inhibitors and increases weight gain of insect pest," *Proc. Natl. Acad. Sci. USA*, 96:1146-1151 (Feb. 1999).

Rustécci, C. et al., "Involvement of lipoxygenase-dependent production of fatty acid hydroperoxides in the development of the hypersensitive cell death induced by cryptogein on tobacco leaves," *J. Biol. Chem.*, 274:36446-36455 (Dec. 17, 1999).

Sambrook, J. et al., "Molecular Cloning: A Laboratory Manual, 2nd Ed., Cold Spring Harbor Laboratory Press, Cold Spring Harbor, New York," *ISBN*, 0-87969-309-6, 5 pages (1989).

Sambrook, J. and Russell, D.W., "Molecular Cloning. A Laboratory Manual, 3rd Ed.," Cold Spring Harbor Laboratory Press, Cold Spring Harbor, New York, *ISBN*, 0-87969-577-3, 11 pages (2001).

Saravitz, D.M. and Siedow, J.N., "The differential expression of wound-inducible lipoxygenase genes in soybean leaves," *Plant Physiol.*, 110:287-299 (1996).

Schmitt, N.F. and Van Mechelen, J.R., "Expression of lipoxygenase isoenzymes in developing barley grains," *Plants Sci.*, 128:141-150 (1997).

Soldatov, K.I., "Chemical mutagenesis in sunflower breeding," *In: Proceedings of the VIIth International Sunflower Conference (Jun. 27-Jul. 3, 1976)* Krasnodar, USSR,—International Sunflower Association, Toowoomba, Australia, vol. 1, pp. 352-357 (1976).

Srivastava, S. et al., "Structural and kinetic determinants of aldehyde reduction by aldose reductase," *Biochemistry*, 38:42-54 (1999) (web: Dec. 10, 1998).

Start, W.G. et al., "Two soybean seed lipoxygenase nulls accumulate reduced levels of lipoxygenase transcripts," *Plant Mol. Biol.*, 7:11-23 (1986).

Tatulian, S.A. et al., "Uncovering a calcium-regulated membrane-binding mechanism for soybean lipoxygenase-1," *Biochemistry*, 37:15481-15490 (1998) (web: Oct. 16, 1998).

Tijet, N. et al., "Biogenesis of volatile aldehydes from fatty acid hydroperoxides: Molecular cloning of a hydroperoxide lyase (CYP74C) with specificity for both the 9- and 13-hydroperoxides of linoleic and linolenic acids," *Arch. Biochem. Biophys.*, 386:281-289 (Feb. 15, 2001).

Tingay, S. et al., "*Agrobacterium tumefaciens*-mediated barley transformation," *Plant J.*, 11:1369-1376 (1997).

Towbin, H. et al., "Electrophoretic transfer of proteins from polyacrylamide gels to nitrocellulose sheets: Procedure and some applications," *Proc. Natl. Acad. Sci. USA*, 76:4350-4354 (Sep. 1979).

Turner, J.G. et al., "The jasmonate signal pathway," *Plant Cell*, 14:S153-S164 (2002).

Vancanneyt, G. et al., "Hydroperoxide lyase depletion in transgenic potato plants leads to an increase in aphid performance," *Proc. Natl. Acad. Sci. USA*, 98:8139-8144 (Jul. 3, 2001).

van Mechelen, J.R. et al., "Primary structure of a lipoxygenase from barley grain as deduced from its cDNA sequence," *Bioche. Biophys. Acta*, 1254:221-225 (1995).

van Mechelen, J.R. et al., "Molecular characterization of two lipoxygenases from barley," *Plant Mol. Biol.*, 39:1283-1298 (1999).

von Wettstein, D. et al., "Biochemical mutant in barley renders chemical stabilization of beer superfluous," *Carlsberg Res. Commun.*, 42:341-351 (1977).

von Wettstein, D. et al., "Proanthocyanidin-free barley for brewing: Progress in breeding for high yield and research tool in polyphenol chemistry," *Tech. Q. MBAA*, 22:41-52 (1985).

Wan, Y. and Lemaux, P.G., "Generation of large numbers of independently transformed fertile barley plants," *Plant Physiol.*, 104:37-48 (1994).

Wang, J. et al., "Alternatively spliced TCR mRNA induced by disruption of reading frame," *Science*, 297:108-110 (Jul. 5, 2002).

Wang, M.-B. et al., "*Agrobacterium tumefaciens*-mediated transformation of an elite Australian barley cultivar with virus resistance and reporter genes," *Aust. J. Plant Physiol.*, 28:149-156 (2001).

Wang, W.H. et al., "Molecular basis of a null mutation in soybean lipoxygenase 2: Substitution of glutamine for an iron-ligand histidine," *Proc. Natl. Acad. Sci. USA*, 91:5828-5832 (Jun. 1994).

Wang, W.-H. et al., "Two single-base substitutions involved in altering in a paired-box of AAATAC in the promoter region of soybean lipoxygenase L-3 gene impair the promoter function in tobacco cells," *Plant Sci.*, 109:67-73 (1995).

Weber, H. et al., "Divinyl ether fatty acid synthesis in late blight-diseased potato leaves," *Plant Cell*, 11:485-493 (Mar. 1999).

Wesley, S.V. et al., "Construct design for efficient, effective and high-throughput gene silencing in plants," *Plant J.*, 27:581-590 (2001).

White, J. et al., "A cassette containing the *bar* gene of *Streptomyces hygroscopicus*: A selectable marker for plant transformation," *Nucleic Acids Res.*, 18:1062 (1990).

Zhang, Y. et al., "Expression of antisense SnRK1 protein kinase sequence causes abnormal pollen development and male sterility in transgenic barley," *Plant J.*, 28:431-441 (2001).

Drost et al., "Flavor Stability." *ASBC Journal*, 1990. vol. 48(4), pp. 124-131.

Kuroda et al, "Characterization of Factors That Transform Linoleic Acid into Di- and Trihydroxyoctadecenoic Acids in Mash." *Journal of Bioscience and Bioengineering*, 2002. vol. 92(1) pp. 73-77.

Kuroda et al., "Enzymes that Transform Linoleic Acid into Di- and Trihydroxyoctadecenoic Acids in Malt." *BAA TQ*, 2003. vol. 40(1) pp. 11-16.

Kobayashi et al., "Behavior of Mono-,Di- and Trihydroxyoctadecenoic Acids during Mashing and Methods of Controlling Their Production." *Journal of Bioscience and Bioengineering*, 2000. vol. 90(1) pp. 69-73.

Rutgersson et al., "Optimization of Temperature, Time and Lactic Acid Concentration to Inactivate Lipoxygenase and Lipase and Preserve Phytase Activity in Barley (cv. Blenheim) During Soaking." *Cereal Chemistry*, 1997. vol. 74(6) pp. 727-732.

Robbins et al., 1998, *Plant Physiol.*, 116:1133-1144 "Genetic Manipulation of Condensed Tannins in Higher Plants".

Stahl et al., 2004, *The Plant Journal*, 39:599-611 "Antisense Downregulation of the Barley Limit Dextrinase Inhibitor Modulates Starch Granule Size Distribution, Starch Composition and Amylopectin Structure".

Narzib et al., 1990, Brauwelt international, pp. 126-134 "Latest findings on beer foam".

* cited by examiner

|  | Gene | | | Protein | |
|---|---|---|---|---|---|
|  | Change | Position in genomic DNA | Result | Length in amino acids | Mass in kDa |
| Wild-type | — | — | — | 862 | 96.4 |
| Mutant A618 | G→A | 2311 | RNA splicing error; translational stop | 399 | 44.5 |
| Mutant D112 | G→A | 3574 | Translational stop | 665 | 74.2 |

Figure 16

US 7,420,105 B2

BARLEY FOR PRODUCTION OF FLAVOR-STABLE BEVERAGE

1. FIELD OF THE INVENTION

The present invention relates to plant biotechnology, disclosing barley and malt defective in synthesis of the lipoxygenase (LOX) enzyme LOX-1, thus providing a new raw material for industrial usage. For example, said raw material can be used for manufacturing a new and distinctive flavor-stable beer having no or negligible quantities of the off-flavor compound trans-2-nonenal (T2N). Said T2N is formed by the sequential action of LOX pathway enzymes, where the LOX-1 represents the primary activity, conferring dioxygenation of linoleic acid to yield 9-hydroperoxy octadecadienoic acid (9-HPODE). Barley and plant products of the invention exhibit no or only negligible quantities of 9-HPODE. In addition, the invention relates to beverages produced using said barley and/or malt.

2. BACKGROUND OF THE INVENTION

One of the research goals related to modern beer production is determining the molecular factors for beer quality and stability. A large fraction of beer is produced on the basis of barley (*Hordeum vulgare*, L.). It is a monocotyledonous crop plant grown in many parts of the world, not only due to its economic importance as a source of industrial products, such as beer, but also as a source of animal feed. The United States is now one of the leading producers of malting barley, with around 13% of the world crop; Canada, Australia and Europe together account for about 70% of the production (Bios Intern., 2001).

A continuing effort of barley breeders is to develop stable, high-yielding cultivars that are agronomically sound. To accomplish this goal, attempts have included random mutagenesis by chemical treatment or irradiation to modify traits of interest, for example to alter the expression of specific genes that may have deleterious effects on plant growth and crop productivity in general—but also on traits conferring added quality to a product manufactured from the crop. It is well established that sodium azide, $NaN_3$, is a useful chemical to mutagenize barley. Specifically, $NaN_3$-derived mutagenesis has been used to induce genetic changes in barley to generate mutants blocked in the synthesis of anthocyanins and proanthocyanidins (von Wettstein et al., 1977; von Wettstein et al., 1985; Jende-Strid, 1991; Jende-Strid, 1993; Olsen et al., 1993). A second example relates to barley kernels mutagenized with $NaN_3$ to screen for high levels of free phosphate with the aim to identify low-phytate mutants (Rasmussen and Hatzak, 1998); a total of 10 mutants out of 2,000 screened kernels were identified. Although a major drawback in barley genetics has been the inability to specifically study gene function through reverse genetics, forward genetic screens—e.g. following $NaN_3$-induced mutagenesis—continue regarding improvements that relate to nutritional and product quality parameters of barley and malt.

Except in a gross and general fashion, a breeder cannot predict the outcome of new plant lines under development in a conventional plant breeding process. This unpredictability is mainly caused by the lack of control at the cellular level, more specifically at the level of nuclear DNA—the complexity of which is enormous. A number of other factors influence the outcome of a plant breeding process, for example the climate and soil quality at the geographical location of plant propagation. As a result, different barley breeders that use conventional techniques will never develop plants with identical traits. In the conventional breeding process, a most difficult task is the identification of plants that are genetically superior, not only with respect to the trait of interest, but also with respect to physiological issues of relevance for plant growth. The selection process is particularly difficult when other confounding traits mask the trait of interest. When present-day plant breeding procedures include DNA sequence determination of the mutated gene, it is at a late stage of the breeding program—i.e. after mutant characterization, for example as recently described for screening of chemically induced mutations in *Arabidopsis* and other plants (Colbert et al., 2001).

Thus far, the creation of gene-indexed loss-of-function mutations on a whole-genome scale has been reported for the yeast *Saccharomyces cerevisiae* (Giaever et al., 2002). For the plant *Arabidopsis*, 21,700 of the ~29,454 predicted genes have been inactivated by the insertion of *Agrobacterium* T-DNA sequences (Alonso et al., 2003).

Until now, it is not unusual that a conventional breeding process from the first mutagenesis or crossing to marketing of plants or seeds takes >10 years. Specifically, it would be excellent to provide the plant breeder with methods to detect mutations in the gene related to the trait of interest. Such improvements would enhance the level of predictability in breeding programs, especially when the selection of mutants is directed toward those having nonsense mutations in the protein-coding part of the gene of interest. In other cases, it may also be preferred with an early identification of DNA mutations, for example to cancel further breeding with lines characterized by promoter mutations in the gene of intererest or where other DNA mutations influence expression—simply because environmental or physiological factors could confer reversion of the trait induced by the mutagen. Accordingly, there is a demand for finding alternative ways of detecting mutations of interest early in the breeding program. This should make the entire breeding process faster and economically of higher interest, thus maximizing the amount of grain produced on the land.

A major proportion of the barley produced comprises malting varieties, the kernels of which are converted to malt through processes of controlled steeping, germination, and drying of the barley. A small proportion of the malt is used as ingredients in the food industry, whereas the majority of the malt is subsequently used as the main ingredient in the production of malt-derived beverages, including, but not limited to, beer and whisky. In the brewhouse, milled malt is subjected to a mashing process comprising a step-wise increase in temperature of a malt-water suspension which confers partial, enzymatic degradation and extraction of, for example, the kernel polymers starch and β-glucan. Following filtration, the aqueous mash is boiled with hops to yield the wort. Said wort is subsequently fermented with yeast, giving the beer product which—upon maturation—is bottled. The wort can also be used for the production of non-fermented malt beverages.

Palatability and flavor stability of a beverage is an important factor of relevance to the composition of barley and malt. This is because natural flavor molecules derived from said barley and malt—or generated by the action of enzymes extracted from said barley and malt—may confer undesirable taste characteristics to the final product (Drost et al., 1990). In this respect, formation of the volatile compound giving a cardboard-like flavor appears to be of particular biochemical as well as economic interest. In 1970, the molecule responsible for cardboard-like flavor was isolated and identified as T2N, a nine-carbon ($C_9$) alkenal (Jamieson and Gheluwe, 1970). Since the taste-threshold level for T2N in humans is extremely low, previously determined to be around 0.7 nM or 0.1 ppb (Meilgaard, 1975), products with even minute levels of the aldehyde are regarded as being aged due to the off-flavor taste of the product. Moreover, liberation of T2N from decomposing T2N adducts during beer storage may cause deterioration of the product (Nyborg et al., 1999).

Radioactive labeling studies with plant tissue established that nonenals are derived from the $C_{18}$ fatty acid linoleic acid, whereas the hexanals and nonadienals are formed from the $C_{18}$ fatty acid linolenic acid (Grosch and Schwartz, 1971; Phillips and Galliard, 1978). These and numerous subsequent observations—for example as summarized by Tijet et al. (2001), Noordermeer et al. (2001), and Matsui et al. (2003)—have been interpreted as evidence that T2N is formed by the sequential action of LOX pathway-specific enzymes, with the action of LOX representing an early enzymatic step. Consistent with this notion, Kurodo et al. (2003) found that malt contains a heat-stable enzymatic factor which is necessary for the transformation of the products made by LOX into T2N. The barley kernel contains three LOX enzymes known as LOX-1, LOX-2 and LOX-3 (van Mechelen et al., 1999). While LOX-1 catalyzes the formation of 9-HPODE—a precursor of T2N—from linoleic acid, LOX-2 catalyzes the conversion of linoleic acid to 13-HPODE which is further metabolized to hexanal (FIG. 1B), a $C_6$ aldehyde with a taste threshold level of around 0.4 ppm (Meilgaard, supra). Although the product specificity of LOX-3 remains elusive, the very low expression level of the corresponding gene, as shown by van Mechelen et al. (supra), suggests that its contribution to T2N formation is negligible. Research is ongoing to determine if LOX activity is the sole enzymatic source for the generation of linoleic acid hydroperoxide precursors of relevance for the formation of the T2N-specific off-flavors, or whether the process of fatty acid autooxidation contributes as well. It is notable that $C_{18}$ hydroperoxides can be further converted by more than seven different families of plant and animal enzymes, with all reactions collectively called the LOX pathway (Feussner and Wasternack, 2002); this pathway is also referred to as the oxylipin pathway. Oxylipins, as their name implies, are oxygenated lipid-derived molecules, which result from the oxygenation of unsaturated fatty acids via the LOX reaction and also include any molecules derived from such oxygenated molecules.

Barley kernels and barley plants having a LOX-1 protein characterized by reduced activity were disclosed in PCT application PCT/IB01/00207 published as WO 02/053721A1 to Douma et al. However, said application does not teach the generation and analysis of barley kernels with inactive LOX-1 enzyme.

Several examples on mutated plants that synthesize low levels of LOX are known. For example, three soybean lines were identified in the early 1980s, each deficient in one of the three LOX enzymes in mature soybean seed:
 (i) LOX-1. Although the molecular basis of the LOX-1 null mutation remains uncertain, it correlates with the absence of the corresponding mature mRNA (Hildebrandt and Hymowitz, 1982; Start et al., 1986);
 (ii) LOX-2. Transcripts for the mutated gene were detected, and a single base change was observed which replaces a histidine ligand to the active site iron, leading to enzyme instability (Davies and Nielsen, 1986; Wang et al., 1994);
 (iii) LOX-3. LOX-3 null mutants exhibited no detectable levels of the corresponding transcript, probably as a consequence of cis-acting elements in the gene promoter (Kitamura et al., 1983; Wang et al., 1995).

In pea seed, a null-LOX-2 line was found to carry a defect leading to the absence of most LOX-2 protein (Forster et al., 1999). Since this line exhibited a great decrease in the amount of mRNA for LOX-2, it was suggested that the mutation caused a dramatic reduction in mRNA stability.

In rice, immunoblot screening of extracts revealed the presence of two natural cultivars, Daw Dam and CI-115, each lacking one of three LOX enzymes (Ramezanzadeh et al., 1999). It was determined that the amount of hexanal, pentanal, and pentanol in normal rice with all three LOXs was markedly induced during storage, while that in Daw Dam and CI-115 was reduced in the range from 66% to 80%. Despite that the results suggest the absence of LOX enzymes in rice grains alleviate oxidative deterioration, the molecular determinants which impart the LOX-less characteristics of Daw Dam and CI-115 remain elusive.

Both antisense-mediated and co-suppression-mediated transgenic depletion of genes for LOX have proved useful to elucidate the function of specific LOX enzymes and their corresponding products in plant defense signaling. In Arabidopsis, for example, depletion of a LOX enzyme led to a reduction in the wound-induced accumulation of jasmonic acid (Bell et al., 1995). And results of antisense-mediated depletion of a gene encoding LOX established the involvement of the corresponding enzyme in the incompatibility trait of a tobacco plant resistant to a fungal pathogen (Rancé et al., 1998). A third example where transgenic approaches have been used to elucidate LOX functions relates to the role of a potato LOX, denoted LOX-H1, in growth and development of potato plants (León et al., 2002). It was shown that LOX-H1 depletion resulted in a marked reduction of volatile aliphatic $C_6$ aldehydes, compounds involved in plant defense responses and acting as either signaling molecules for wound-induced gene expression or as antimicrobial substances. A further study showed that transgenic potato plants depleted in the expression of a gene for a LOX enzyme exhibited abnormal tuber development (Kolomiets et al., 2001). However, specific oxylipins that accounted for the tuber phenotype were not identified. In another study, antisense-mediated depletion of potato LOX-H3 suppressed the inducible defense response of the plant, concomitant with a higher tuber yield (Royo et al., 1999). Collectively, these data suggest that expression of genes encoding LOX enzymes is important in plant development, possibly with some LOX enzymes playing a defensive role against pathogens, whereas other LOX enzymes generate products that may act to regulate cell development.

It is also of importance to note that tomato fruits with 2-20% reduced levels of two LOX enzymes showed no significant changes in flavor volatiles when compared to wild-type fruits (Griffiths et al., 1999). This finding suggests that either very low levels of LOX are sufficient for the generation of aldehydes and alcohols, or that other LOX enzymes are active in the generation of these compounds.

The role of LOX enzymes is also related to issues outside the field of manufacturing beer, such as LOX-catalyzed generation of hydroperoxy fatty acids that inhibit mycotoxin formation in plants susceptible to fungal contamination, for example as disclosed in U.S. Pat. No. 5,942,661 to Keller. Although the role for LOX enzymes in plant defense and wounding responses remains less clear, the enzymes are induced upon wounding and pathogen challenge (Bell and Mullet, 1991; Bell and Mullet, 1993; Melan et al., 1993; Sarvitz and Siedow, 1996). LOX enzymes' role in wounding and plant defence could be to produce reactive fatty acid hydroperoxides against pathogens (Rogers et al., 1988).

Alternatively, LOXs may be induced by stresses to produce signal molecules, such as methyl jasmonate (Bell et al., supra).

Strategies have also been described where 13-HPODE, produced by the action of a LOX enzyme, acts as a substrate for hydroperoxide-converting enzymes to produce flavor-active aldehydes (Noordermeer et al., 2002; Husson and Belin, 2002). Similar processes are disclosed in numerous patents, e.g. U.S. Pat. No. 6,150,145 to Häusler et al. and U.S. Pat. No. 6,274,358 to Holtz et al.

Also, LOX enzymes have been shown to contribute several beneficial effects to bread-making (Casey, 1997). Moreover, U.S. Pat. No. 6,355,862 B1 to Handa and Kausch discloses that fruit quality can be enhanced by inhibiting production of LOX, such as giving a longer shelf life to the product.

3. SUMMARY OF THE INVENTION

There exists thus an unmet need for barley plants with essentially no LOX-1 activity, because beverages prepared from such plants will have very low levels of T2N. In addition, such plants may be useful for other purposes.

Surprisingly, the present invention discloses methods for preparing barley plants with no or very little LOX-1 activity. In particular, the invention discloses null mutations in the gene for LOX-1. The prospective benefits of the invention include a total elimination of T2N from the corresponding branch of the LOX pathway, and the invention thus provides a superior way for controlling T2N levels in the barley kernel; and beer produced from these kernels exhibit exceptional taste stability after prolonged storage, even at elevated temperatures.

Interestingly, the present invention also provides methods for early mutation detection, and hence the disadvantages of late mutant characterization have been solved by the present invention. This makes use of a new attractive procedure for generating improved malting barley cultivars, introducing the sequential use of phenotype characterization and DNA sequence determination of target genes in a mutant population at an early time point in the breeding process. Isolated plants can be further improved using a variety of plant breeding methods.

The present invention solves the current problems, limitations and disadvantages related to the presence of active LOX-1 enzyme in barley. First, this invention provides a novel, efficient screening method that significantly reduces the time and labor for screening chemically mutagenized barley. Second, the present invention includes novel null-LOX-1 barleys, for example useful in the production of flavor-stable beer.

The theoretical background art for plant LOX mutants, as described above, is related to plants having reduced levels of LOX activity. In contrast, the present invention overcomes the limitations and disadvantages related to low or residual LOX activity by providing ways to effectively generate null-LOX-1 barley plants. Specific differences include:

(i) In contrast to barley plants disclosed in PCT application PCT/IB01/00207 published as WO 02/053721A1 to Douma et al., plants of the present invention comprise essentially no LOX-1 activity, preferably the plants are true null-LOX-1 plants—i.e. the plants exhibit a total lack-of-function of LOX-1 protein;

(ii) The true null-LOX-1 trait described herein could be identified by screening for the presence of a nonsense mutation in the corresponding gene. Accordingly, barley plants homozygous for that trait would be completely blocked in the synthesis of active enzyme—irrespective of growth conditions or environmental effects. This is an ideal property in the art of plant breeding and contrasts the outcome of a possible molecular scenario in the soybean LOX mutants of the background art, where biotic or abiotic conditions could affect changes in the physiological state of cells to confer mRNA stabilization with subsequent translation of LOX;

(iii) Where the trait of relevance in LOX mutants of soybean and rice comprised reduced levels of the odor-intense compound hexanal in a staple food, the present invention relates to lower levels of the taste-specific compound T2N in a beverage;

(iv) The soybean and rice LOX mutants are affected in molecules of the LOX pathway downstream of 13-HPODE, while the null-LOX-1 trait relates to that branch of the LOX pathway which comprises molecules downstream of 9-HPODE;

(v) While the soybean mutants comprise irradiation-induced mutations in genes for LOX, and Daw Dam and CI-115 represent selected naturally occurring cultivars of rice breeding lines, mutations in barley plants having the null-LOX-1 trait were induced by the chemical $NaN_3$.

Hence, it is an objective of the present invention to provide barley plants, parts or fragments thereof comprising less than 5%, preferably less than 1% of the LOX-1 activity of a wild-type barley plant.

It is a second objective of the invention to provide kernels from a barley plant comprising less than 5%, preferably less than 1% of the LOX-1 activity of a wild-type plant.

A third objective of the present invention is to provide compositions comprising a barley plant, or parts or fragments thereof comprising less than 5%, preferably less than 1% of the LOX-1 activity of a wild-type barley plant.

It is a further objective of the invention to provide malt compositions comprising a processed barley plant comprising less than 5%, preferably less than 1% of the LOX-1 activity of a wild-type barley plant. Malt compositions may preferably be pure malt compositions. However, malt compositions may also be for example blends of barley and malt.

It is also an objective of the present invention to provide beverages having stable organoleptic qualities, wherein said beverages are manufactured using the barley plant of the invention or part thereof. In particular, it is preferred that said beverages are manufactured using the malt composition, such as a pure malt composition or a blend of barley and malt, described herein above. In a preferred embodiment of the invention said beverages consist of beer.

It is an additional objective of the invention to provide a beverage having stable organoleptic qualities, wherein said beverage is manufactured using a barley plant and wherein the ratio of 9,12,13-trihydroxyoctadecenoic acid to 9,10,13-trihydroxyoctadecenoic acid within said beverage is at the most 1.8. Preferably, said beverage is beer.

Moreover, an objective of the invention is to provide compositions, such as food compositions, feed compositions, or fragrance raw material compositions that comprise the barley plant according to the invention or parts thereof.

In addition, it is an objective of the present invention to provide methods for expressing a recombinant protein in a barley plant according to the invention, wherein said method comprises transforming said plant with a nucleic acid sequence comprising, as operably linked components a promoter expressable in barley plants or parts thereof, a DNA sequence encoding said recombinant protein, and a transcriptional termination region, thereby expressing said recombinant protein in said barley plant.

Further, an objective of the present invention is to provide methods for reducing the levels of a protein in a barley plant of the invention, wherein said method includes transforming said plant with a nucleic acid sequence comprising, as operable linked components, a promoter expressable in barley plants or parts thereof, a DNA sequence, and a transcriptional termination region, wherein expression of said DNA sequence reduces the expression of a gene encoding said protein by antisense, or co-suppression or RNA interference.

An additional objective of the present invention is to provide methods of preparing a barley plant comprising less than 5%, preferably less than 1% of the LOX-1 activity of a wild-type barley plant comprising the steps of:
  (i) Determining the LOX-1 activity in wild-type barley kernels or parts thereof; and
  (ii) Mutagenizing barley plants and/or barley kernels and/or barley embryos, thereby obtaining generation MO barley; and
  (iii) Breeding said mutagenized barley plants, kernels and/or embryos for at least 2 generations, thereby obtaining generation Mx barley plants, wherein x is an integer $\geq 2$; and
  (iv) Obtaining kernels or parts thereof from said Mx barley plants; and
  (v) Determining the LOX-1 activity in said kernels or parts thereof; and
  (vi) Selecting plants wherein the LOX-1 activity of the mutagenized kernels or parts thereof is less than 5% than the LOX-1 activity of the wild-type kernels or part thereof;

thereby obtaining a barley plant comprising less than 5% of the LOX-1 activity of a wild-type barley plant.

Still further, it is an objective of the present invention to provide methods of producing a beverage having stable organoleptic qualities comprising the steps of:
  (i) Providing a malt composition according to the invention;
  (ii) Processing said malt composition into a beverage;

thereby obtaining a beverage with stable organoleptic qualities.

It is an additional objective of the present invention to provide methods of producing a malt composition with low LOX-1 activity, comprising the steps of
  (i) Providing kernels according to the invention;
  (ii) Steeping said kernels;
  (iii) Germinating the steeped kernels under predetermined conditions;
  (iv) Treating germinated kernels with heat;

thereby producing a malt composition with low or no LOX-1 activity.

In one preferred embodiment, the present invention is based on the unpredicted outcome of functional studies of barley mutant D112, which revealed a total loss-of-function with respect to the major 9-HPODE-forming enzyme LOX-1. It was a surprising discovery to detect a 10%:90% distribution of 9-HPODE:13-HPODE in biochemical assays designed to determine the product profile following LOX-catalyzed conversion of linoleic acid. Given the extremely low taste-threshold of T2N, it was even more surprising that degradation of residual 9-HPODE and the like in kernels of mutant D112 only caused very low liberation of T2N—well below the taste threshold level—during aging of beer products manufactured from malt of said kernels.

Examination of the results from analyses using wild-type and null-LOX-1 kernels provide clear evidence that high LOX-1 activity can intensify the stale cardboard flavor of T2N, thus confirming an important role of the LOX pathway in controlling formation of the alkenal. This conclusion contrasts the notion of Liegeois et al. (supra), who suggested that LOX activity only contributes with a small fraction of the T2N precursor molecules.

The null-LOX-1 trait can be introduced into established malting barley varieties, thus allowing production of flavor-stable beverages with prolonged shelf lives. This approach will not only be independent of the geographical region where mutant D112-derived barley is grown, but also independent of the location where mutant D112-derived beer is produced and sold to customers. Barley plants of mutant D112, or plants derived thereof, are potentially an important economical factor for farmers that grow the crop, and for breweries that use it as a raw material for beer production. Other applications that depend on raw materials without 9-HPODE/9-HPOTE-forming activities are also anticipated to benefit from the properties of barley mutant D112.

In accordance with one embodiment of the invention, there is provided several novel malting barley mutants, for example the mutants designated D112 or A618. The present invention is therefore related to the kernels of barley mutants D112 or A618, to the plants of barley D112 or A618 and to methods for producing a barley plant derived from crossing barley mutants D112 or A618 with itself or another barley line. Moreover, the present invention comprises null-LOX-1 variants generated by mutagenesis or transformation of barley mutant D112 or A618. Thus, all plants produced using barley mutants D112 or A618—or a derivative thereof—as a parent are within the scope of this invention.

In another aspect, the invention provides regenerable cells for use in tissue culture of barley mutant plant D112 or A618. The tissue culture will preferably be used for regeneration of plants having the characteristics of the foregoing barley plants, including morphological and genetic characteristics. The regenerated cells in such tissue cultures will be embryos, protoplasts, meristematic cells, callus, pollen, anthers, etc. It is understood that the present invention provides barley plants regenerated form the tissue cultures of the invention.

In a preferred embodiment, the present invention comprises malt derived from null-LOX-1 barley kernels.

The present invention also relates to wort compositions prepared from null-LOX-1 barley plants or parts thereof or from malt compositions prepared from such barley plants.

The invention further comprises beverages, such as beer manufactured using either null-LOX-1 barley kernels of the present invention or malt derived from said kernels.

In addition, the invention relates to a plant product produced from a null-LOX-1 barley plant or parts thereof. Said plant product may be any product resulting from processing of said barley plant or part thereof. Preferably, said plant product is selected from the group consisting of malt, wort, fermented beverages such as beer, non-fermented beverages, food products such as barley meal and feed products.

It is also an object of the present invention to provide null-LOX-1 barley kernels exhibiting such levels of disease resistance that are indistinguishable from wild-type barley plants or even have improved disease resistance.

Still further, the invention comprises null-LOX-1 barley kernels and malt derived from said kernels, where both kernels and malt exhibit reduced levels of mycotoxins.

Also, the present invention comprises null-LOX-1 barley varieties with enhanced disease resistance relative to wild-type plants. Further, null-LOX-1 barley having reduced disease resistance relative to wild-type plants are disclosed, provided that other characteristics of said plants provide benefits that are more important than the property of reduced disease resistance.

In addition, the present invention provides null-LOX-1 barley kernels useful for the production of LOX pathway-derived fragrances, including green note compounds.

Moreover, the present invention provides for transgenic plants of null-LOX-1 barley mutants D112 or A618, or plants derived thereof, where the introduced gene(s) confer such traits as herbicide resistance, insect resistance, resistance for bacterial, fungal, or viral diseases, enhanced nutritional quality, and industrial usage. The gene may be an endogenous barley gene or, alternatively, a transgene introduced through genetic engineering techniques.

These and other features, aspects, and advantages of the present invention will be better understood when related to the following definitions, descriptions, examples, appended claims as well as accompanying sequence listings and drawings.

3.1 Definitions

In the description, figures, and tables which follow, a number of terms are used. In order to provide the specifications and claims, including the scope to be given such terms, the following definitions are provided:

As used herein, "a" can mean one or more, depending on the context in which it is used.

The term "agronomic trait" describes a phenotypic trait of a plant that contributes to the performance or economic value of said plant. Such traits include disease resistance, insect resistance, virus resistance, nemtatode resistance, drought tolerance, high salinity tolerance, yield, plant height, days to maturity, kernel nitrogen content and the like.

By "antisense nucleotide sequence" is intended a sequence that is in inverse orientation to the normal coding 5'-to-3' orientation of that nucleotide sequence. When present in a plant cell, the antisense DNA sequence preferably prevents normal expression of the nucleotide sequence for the endogenous gene, and may disrupt production of the corresponding, native protein.

The term "barley" in reference to the process of making beer, particularly when used to describe the malting process, means barley kernels. In all other cases, unless otherwise specified, "barley" means the barley plant (*Hordeum vulgare*, L.) including any varieties.

By "disease resistance" is intended that the plants avoid the disease symptoms that are the outcome of plant-pathogen interactions. In this way, pathogens are prevented from causing plant diseases and the associated disease symptoms, or alternatively, the disease symptoms. Alternatively, the disease symptoms caused by the pathogen are minimized or reduced.

A "cereal" plant as defined in this publication is a member of the *Graminae* plant family cultivated primarily for their starch-containing seeds. Cereal plants include barley (*Hordeum*), wheat (*Triticum*), rice (*Oryza*), maize (*Zea*), rye (*Secale*), oat (*Avena*), sorghum (*Sorghum*), and *Triticale,* a rye-wheat hybrid.

By "encoding" or "encoded," in the context of a specified nucleic acid, is meant comprising the information for translation into the specified protein. A nucleic acid encoding a protein may comprise non-translated sequences (e.g. introns) within translated regions of the nucleic acid, or may lack such intervening non-translated sequences (e.g. in cDNA). The information by which a protein is encoded is specified by the use of codons.

As used herein, "expression" in the context of nucleic acids is to be understood as the transcription and accumulation of sense mRNA or antisense RNA derived from a nucleic acid fragment. "Expression" used in the context of proteins refers to translation of mRNA into a polypeptide.

By "flavor molecules" is intended aldehydes and/or alcohols that are produced and are constituents of odor and/or taste in plants. In particular, flavor molecules include certain volatile alcohols and aldehydes. Examples of flavor molecules which are volatile include but are not limited to hexanal, (3Z)-hexenal, (2E)-hexenal, (2E)-hexenol, (3Z)-nonenal, (2E)-nonenal. The invention can be used to modulate levels of flavor molecules in plants.

The term "gene" means the segment of DNA involved in producing a polypeptide chain; it includes regions preceding and following the coding region (promoter and terminator). Eukaryotic genes are discontinuous with proteins encoded by them, consisting of "exons" interrupted by "introns.". After transcription into RNA, the introns are removed by splicing to generate a mature messenger RNA (mRNA). The "splice sites" between exons are typically determined by consensus sequences acting as splice signals for the splicing process, consisting of a deletion of the intron from the primary RNA transcript and a joining or fusion of the ends of the remaining RNA on either side of the excised intron. In some cases alternate or different patterns of splicing can generate different proteins from the same single stretch of DNA. A native gene may be referred to as an endogenous gene.

"Gene-silencing" is a method to alter gene expression. It refers to RNA silencing, which is a post-transcriptional gene-silencing mechanism conserved among various organisms. The method includes post-transcriptional gene silencing (PTGS) and RNA interference (RNAi). PTGS is a gene-silencing phenomenon of endogenous and exogenous homologous genes. Although most examples on PTGS are on the effects caused by co-suppression constructs or expression of transgenes in antisense orientation, it has also been observed in plants of conventional breeding programs, e.g. the Lgc1 mutation in rice (Kusaba et al., 2003). This mutation was found to suppress glutelin expression via RNA silencing, possibly due to a 3.5-kbp deletion between two highly similar genes for glutelin that forms a tail-to-tail inverted repeat that might produce a double-stranded RNA molecule—and thus a potent inducer of RNA silencing. A second form of RNA silencing is known as RNA interference (RNAi), where the basic premise is the ability of double-stranded RNA to specifically block expression of its homologous gene when injected or ingested into cells (Goenczy et al., 2000).

As used herein, "heterologous" in reference to a nucleic acid is a nucleic acid that originates from a foreign species, or, if from the same species, is substantially modified from its native form in composition and/or genomic locus by deliberate human intervention.

The term "germination" as used herein means the beginning or resumption of growth by a barley kernel in various compositions, such as normal soil as found in nature. Germination can also take place in the soil of pots placed in growth chambers an the like, or for example take place on wet filter paper placed in standard laboratory Petri dishes. Germination is generally understood to include hydration of the kernels, swelling of the kernels and inducing growth of the embryo. Environmental factors affecting germination include moisture, temperature and oxygen level. Root and shoot development are observed.

"Green notes" is a term describing volatile flavor and fragrance molecules present in numerous plants, and characterized in organoleptic terms as fresh green and grassy. These molecules are produced by the plant from the degradation of lipids and free fatty acids, such as linoleic acid and linolenic acid.

As used herein, the term "isolated" means that the material is removed from its original environment. For example, a naturally-occuring polynucleotide or polypeptide present in a living organism is not isolated, but the same polynucleotide or polypeptide, separated from some or all of the coexisting materials in the natural system, is isolated. Such polynucleotides could be part of a vector and/or such polynycleotides or polypeptides could be part of a composition, and still be isolated because such vector or composition is not part of its natural environment.

The term "kernel" is defined to comprise the cereal caryopsis, also denoted internal seed, the lemma and palea. In most barley varieties the lemma and palea adhere to the caryopsis and are a part of the kernel following threshing. However, naked barley varieties also occur. In these, the caryopsis is free of the lemma and palea and threshes out free as in wheat. The terms "kernel" and "grain" are used interchangeably herein.

"Kernel maturation" or "grain development" refers to the period starting with fertilization in which metabolizable reserves, e.g. sugars, oligosaccharides, starch, phenolics, amino acids, and proteins are deposited, with and without vacuole targeting, to various tissues in the kernel (grain), e.g. endosperm, testa, aleurone, and scutellum, leading to kernel (grain) enlargement, kernel (grain) filling, and ending with kernel (grain) desiccation.

The term "LOX-1 activity" refers to the enzymatic activity of the barley LOX-1 enzyme. In particular, in the context of the present invention "LOX-1 activity" is the enzyme catalyzed dioxygenation of linoleic acid to 9-HPODE. Even though the LOX-1 enzyme is capable of catalyzing other reactions, for the purpose of determining the activity of LOX-1 according to the present invention only the 9-HPODE forming activity should be considered. FIG. 1B outlines the biochemical pathway wherein linoleic acid is converted to T2N.

The term "low-LOX" refers to the presence of one or several mutations in one or several endogenous genes, causing a partial loss-of-function of a specified LOX enzyme, preferably with respect to—but not restricted to—enzymic activity. For example, the barley plants disclosed in PCT application PCT/IB01/00207 published as WO 02/053721 A1 to Douma et al. produce a mutated LOX-1 enzyme having 10% residual activity compared with the corresponding wild-type enzyme. "Low-LOX" with reference to a plant refers to a plant having partial loss-of-function of the specified LOX enzyme.

"Malting" is a special form of germination of barley kernels taking place under controlled environmental conditions, including, but not limited to maltery steep tanks and germination boxes. In accordance with the process of the present invention, malting begins to occur during and/or after the barley kernels have been steeped. The malting process may be stopped by drying of the barley kernels. A malt composition prepared from null-LOX-1 barley is understood to comprise null-LOX-1 malt, such as pure null-LOX-1 malt or any blend of malt comprising null-LOX-1 malt.

"Mashing" is the incubation of milled malt in water. Mashing is preferably performed at a specific temperature and in a specific volume of water. The temperature and volume of water is important as this affects the rate of decrease of enzyme activity derived from the malt, and hence the amount of especially starch hydrolysis that can occur. Mashing can occur in the presence of adjuncts, which is understood to comprise any carbohydrate source other than malt, e.g. barley (including null-LOX-1 barley), maize or rice adjunct, used principally as an additional source of extract. The requirements for processing of the adjunct in the brewery depend on the state and type of adjunct used, and in particular the starch gelatinization or liquefaction temperatures. If the gelatinization temperature is above the normal malt saccharification temperature, then the starch is gelatinized and liquefied before adding to the mash.

"Mutations" include deletions, insertions, transversions and point mutations in the coding and noncoding regions of a gene. Deletions may be of the entire gene or of only a portion of the gene. Point mutations may result in stop codons, frameshift mutations or amino acid substitutions. Somatic mutations are those which occur only in certains cells or tissues of the plant and are not inherited to the next generation. Germ-line mutations can be found in any cell of the plant and are inherited.

The term "null-LOX" refers to the presence of a mutation in a LOX-encoding gene, causing a total loss-of-function of the encoded LOX enzyme. Mutations that generate premature termination (nonsense) codons in a gene encoding LOX represent only one mechanism by which total loss-of-function can be obtained. Molecular approaches to obtain total loss-of-funtion of a LOX enzyme comprise the generation of mutations that cause a total absence of transcripts for said enzyme, or mutations that totally inactivate the encoded enzyme. "null-LOX" with reference to a plant refers to a plant having a total loss-of-function of the specified LOX enzyme.

"Operably linked" is a term used to refer to the association of two or more nucleic acid fragments on a single polynucleotide so that the function of one is affected by the other. For example, a promoter is operably linked with a coding sequence when it is capable of affecting the expression of that coding sequence, i.e. that the coding sequence is under the transcriptional control of the promoter. Coding sequences can be operably linked to regulatory sequences in sense or anti-sense orientation.

"PCR" or "polymerase chain reaction" is well known by those skilled in the art as a technique used for the amplification of specific DNA segments (U.S. Pat. Nos. 4,683,195 and 4,800,159 to Mullis et al.).

"Plant" or "plant material" includes plant cells, plant protoplasts, plant cell tissue cultures from which barley plants can be regenerated, plant calli, and plant cells that are intact in plants or parts of plants, such as embryos, pollen, ovules, flowers, kernels, leaves, roots, root tips, anthers, or any part or product of a plant.

By the term "plant product" is meant a product resulting from the processing of a plant or plant portion. Said plant product may thus for example be malt, wort, a fermented or non-fermented beverage, a food or a feed product.

As used herein, "recombinant" in reference to a protein is a protein that originates from a foreign species, or, if from the same species, is substantially modified from its native form in composition by deliberate human intervention.

"RNA transcript" refers to the product resulting from RNA polymerase-catalyzed transcription of a DNA sequence. When the RNA transcript is a perfect complementary copy of the DNA sequence, it is referred to as the primary transcript. When an RNA sequence is derived from post-translational processing of the primary transcript, it is referred to as the mature RNA. "Messenger RNA" or "mRNA" refers to the RNA that is without introns and that can be translated into proteins by the cell. "cDNA" refers to DNA that is complementary to and derived from an mRNA template. The cDNA can be single-stranded or converted to a double-stranded form using, for example, the Klenow fragment of DNA polymerase I. "Sense RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e. at the 5' non-coding sequence, 3' non-coding sequence, introns, or the protein coding sequence. "Functional RNA" refers to sense RNA, antisense RNA or other RNA that may not be translated into a protein but yet has an effect on cellular processes.

Unless otherwise noted, "T2N" means the free form of T2N. By the term "T2N potential" is described the chemical substances which have the capacity to release T2N, or be converted into T2N, in one or more reactions. The T2N potential can be measured as the concentration of T2N in a solution, e.g. in wort or beer, following an incubation (e.g. for 2 h) at an elevated temperature (e.g. 100° C.) and low acidity (e.g. pH 4.0). This sample treatment causes liberation of T2N from the T2N potential, e.g. from "T2N adducts," a term used to describe T2N conjugated to one or more substances, including, but not limited to, protein(s), sulfite, cellular debris, cell walls, or the like. In general, T2N adducts per se are not sensed by humans as off-flavors. However, T2N released from said T2N adducts, for example by heat or acid, may give rise to an off-flavor.

"Tissue culture" indicates a composition comprising isolated cells of the same or a different type or a collection of such cells organized into parts of a plant, for example protoplasts, calli, embryos, pollen, anthers, and the like.

"Transformation" means introducing DNA into an organism so that the DNA is maintained, either as an extrachromosomal element (without integration and stable inheritance) or chromosomal integrant (genetically stable inheritance). Unless otherwise stated, the method used herein for transformation of *E. coli* was the CaCl$_2$-method (Sambrook and Russel, supra), and *Agrobacterium*-mediated transformation of the barley cultivar Golden Promise was basically as described by Tingay et al. (1997) and Wang et al. (2001), except that only the cultivar Golden Promise was used as host.

A "transgene" is a gene that has been introduced into the genome by a transformation procedure.

As used herein, "transgenic" includes reference to a cell that has been modified by the introduction of a heterologous nucleic acid or that the cell is derived from a cell so modified. Thus, for example, transgenic cells express genes that are not found in an identical form within the native form of the cell, or express native genes that are otherwise abnormally expressed, underexpressed, or not expressed at all as a result of deliberate human intervention. The term "transgenic" in reference to plants, particularly barley plants, as used herein does not encompass the alteration of the cell by methods of traditional plant breeding, e.g. NaN$_3$-derived mutagenesis, and by naturally occurring events such as those occuring without deliberate human invention.

The term "wild-type barley plant" refers to a conventional barley plant, preferably the term refers to the barley plant, from which the barley plants of the invention have been derived, i.e. the parent plants. In one preferred embodiment of the invention, the "wild-type barley plant" is selected from the group consisting of cv.s Celeste, Lux, Prestige, Saloon, and Neruda. More preferably, the "wild-type barley plant" is cultivar Barke.

4. BRIEF DESCRIPTION OF THE SEQUENCE LISTING

The invention can be more fully understood from the following detailed description and the accompanying Sequence Listing (summarized in Table 9), which forms a part of this application. Said table lists the nucleic acids and polypeptides that are described herein, the designation of the cDNA clones that comprise the nucleic acid fragments encoding polypeptides representing all or a substantial portion of these polypeptides, and the corresponding identifier [SEQ ID NO:]. The sequence descriptions and Sequence Listing attached hereto comply with the rules governing nucleotide and/or amino acid sequence disclosures in patent applications.

The Sequence Listing contains the one letter code for nucleotide and amino acid sequence characters as defined in conformity with the standardized recommendations (Cornish-Bowden, 1985; IUPAC-IUB Joint Commission on Biochemical Nomenclature, 1984), which are herein incorporated by reference. The symbols and format used for nucleotide and amino acid sequence data comply with the rules governing sequence disclosures in patent applications.

5. BRIEF DESCRIPTION OF THE DRAWINGS

Figure 1B:
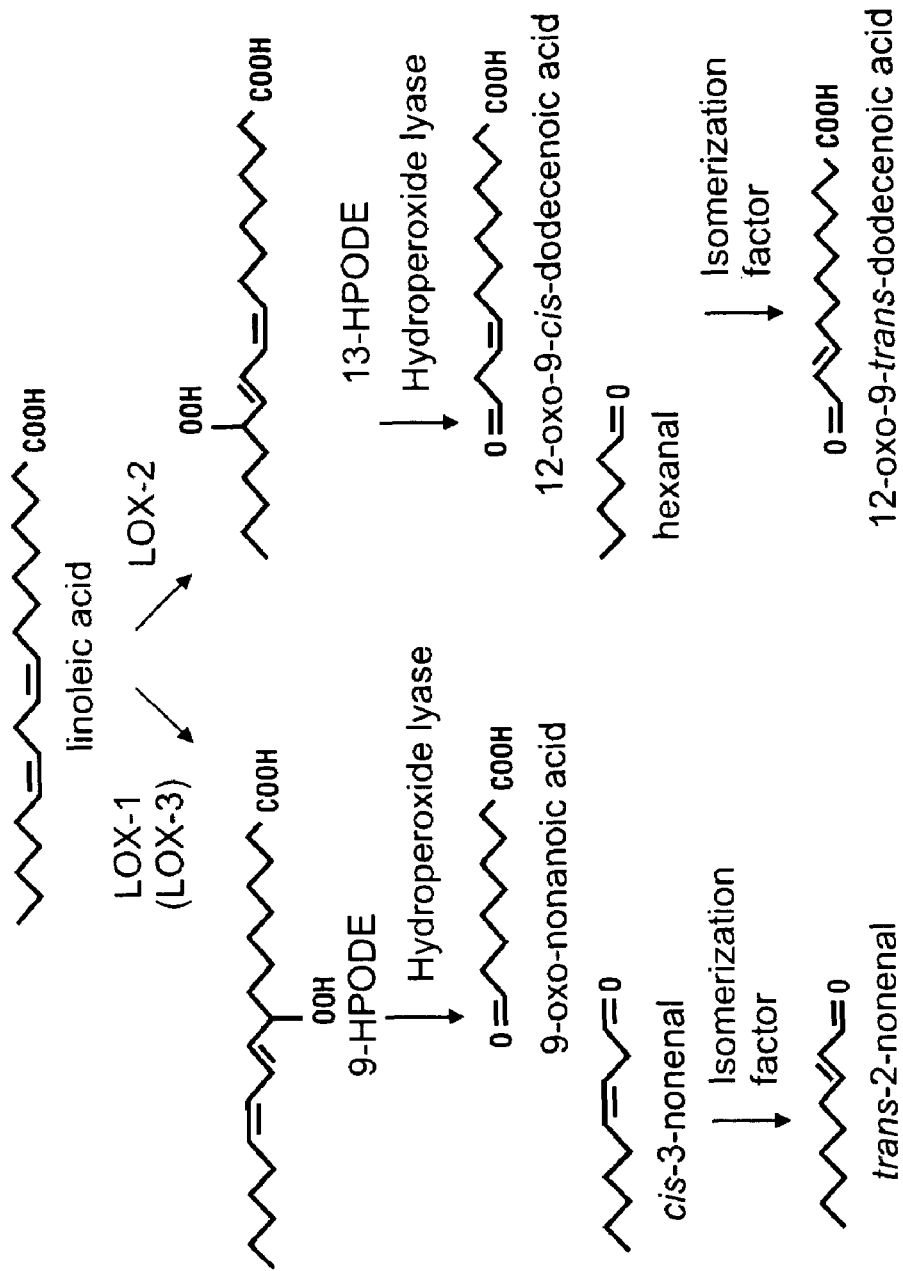

FIG. 1 is divided into two flow diagrams A and B. FIG. 1A shows how NaN$_3$-mutagenized barley kernels may be propagated. Kernels of generation M0 grow into plants that develop kernels of generation M1. These may be sown and develop into M1 plants which produce new kernels of generation M2. Next, M2 plants grow and set kernels of generation M3, which may be harvested and used for screening analyses. M3 seeds may also be sown, and flowers of the corresponding plants used for crossings to obtain plants of generation M4. FIG. 1B is a simplified representation how the biochemical LOX pathway operates to degrade linoleic acid, eventually yielding T2N.

Figure 2:
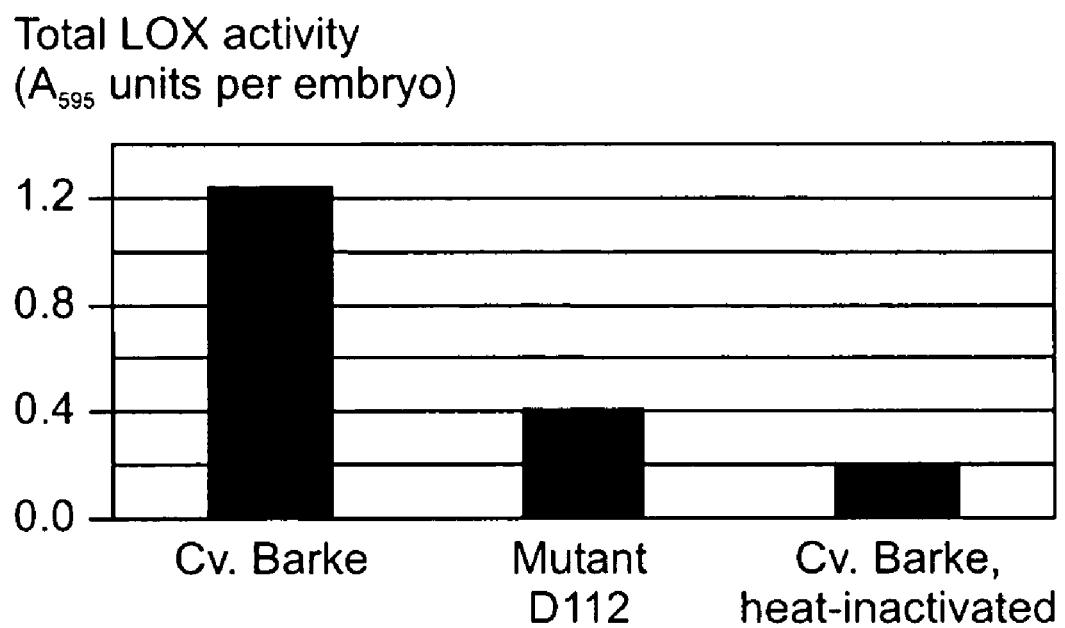

FIG. 2 is a graphic comparison of total LOX activities measured in embryo extracts of cv. Barke, mutant D112, and in a control sample comprising heat-inactivated extract of cv. Barke embryos.

Figure 3:
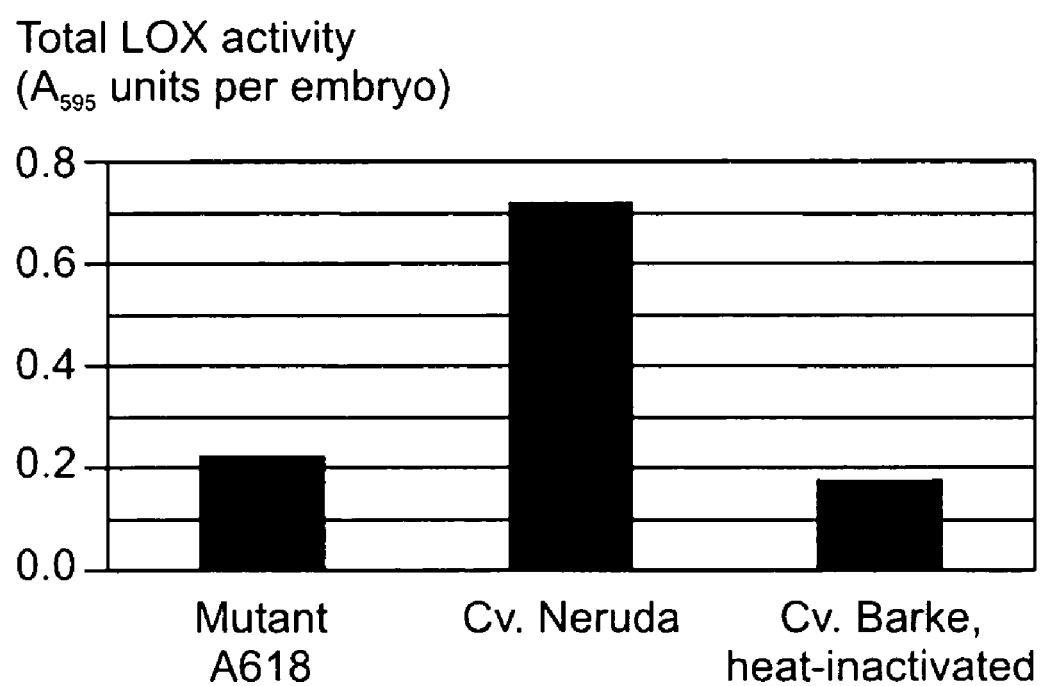

FIG. 3 displays a graphic comparison of total LOX activities measured in embryo extracts of mutant A618, cv. Neruda, and in a control sample comprising heat-inactivated extract of cv. Barke embryos.

Figure 4:
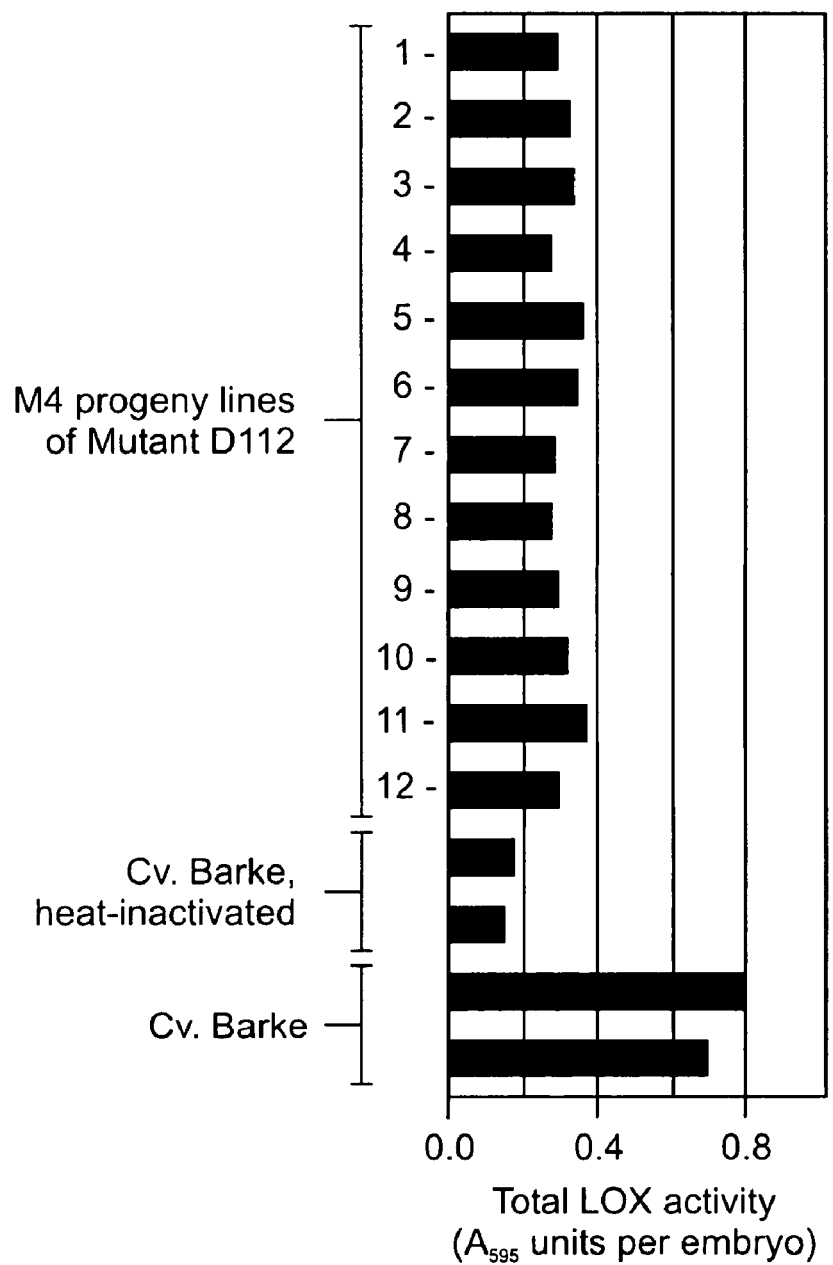

FIG. 4 shows a comparison of total LOX activities measured in kernels of 12 individual M4 progeny lines of mutant D112. The activities of control samples consisting of kernel extracts of cv. Barke, and heat-inactivated kernel extracts of cv. Barke are included in the comparison.

Figure 5:
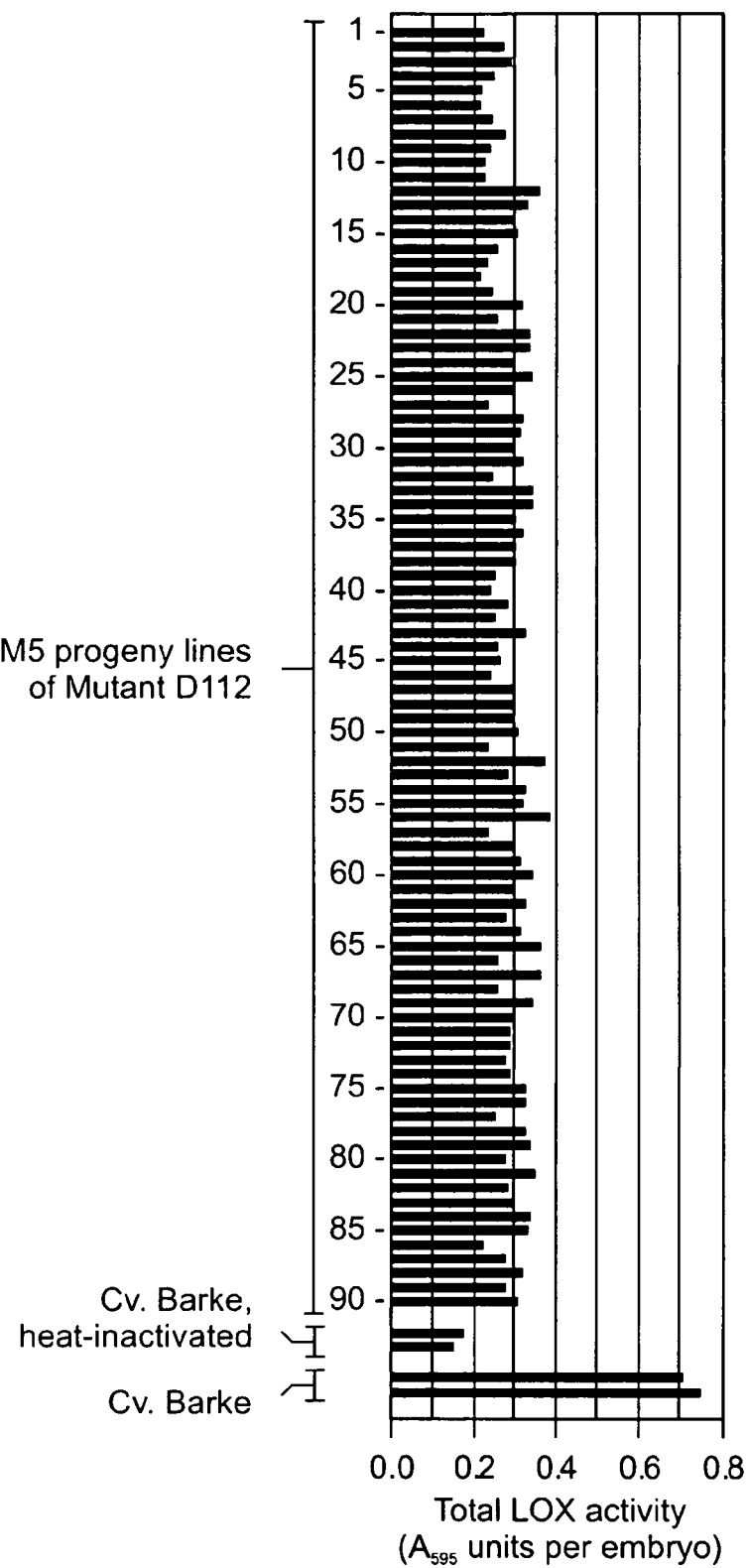

FIG. 5 summarizes the results of analyses for total LOX activity in 90 individual kernel extracts of M5 progeny lines of mutant D112. The activities of control kernel extracts of cv. Barke, and heat-inactivated kernel extracts of cv. Barke are included in the comparison.

Figure 6:
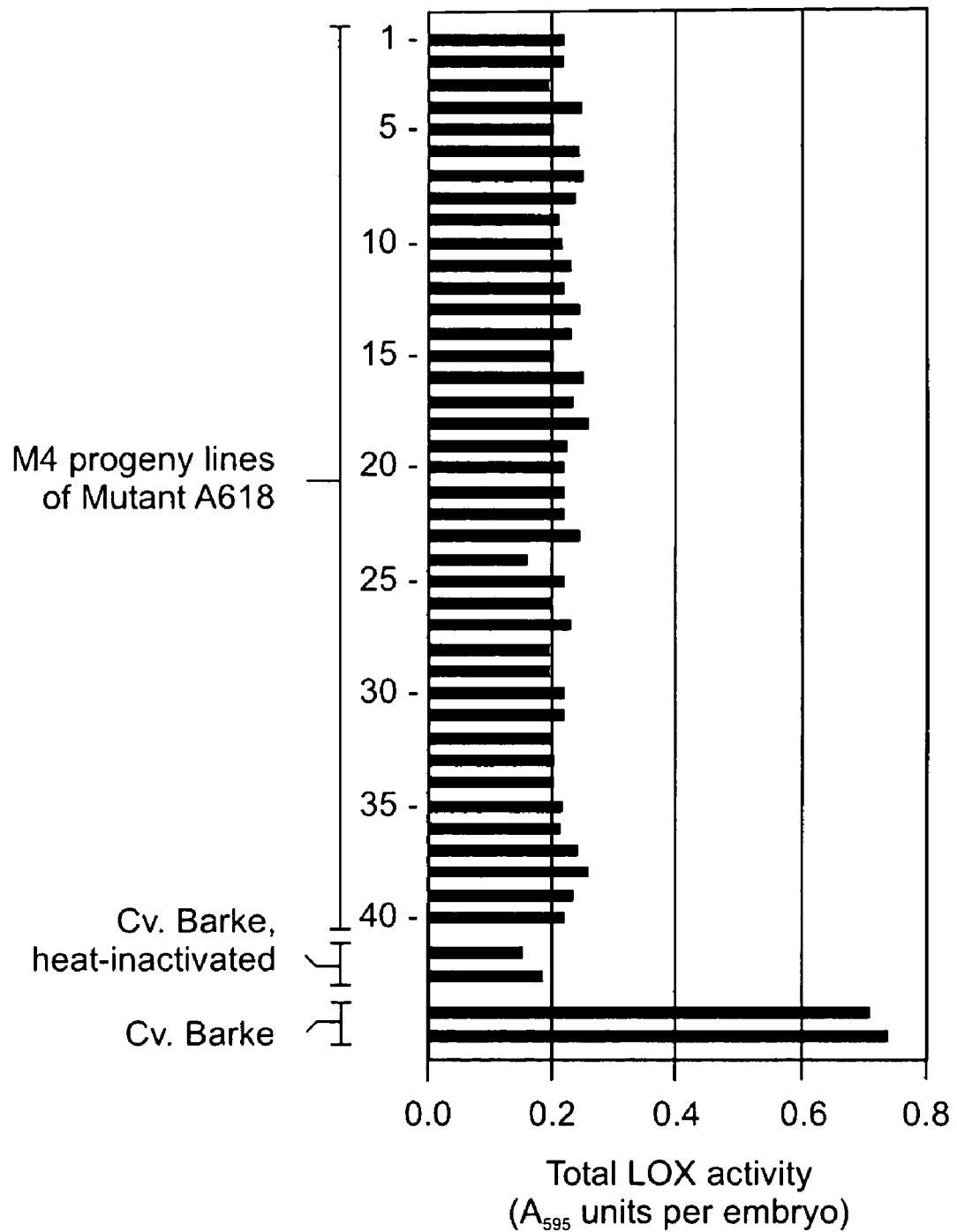

FIG. 6 gives a summary of a comparison of total LOX activities measured in 40 individual kernel extracts of M4 progeny lines of mutant A618. The activities of control samples with kernel extracts of cv. Barke and heat-inactivated kernel extracts of cv. Barke are included in the comparison.

Figure 7:
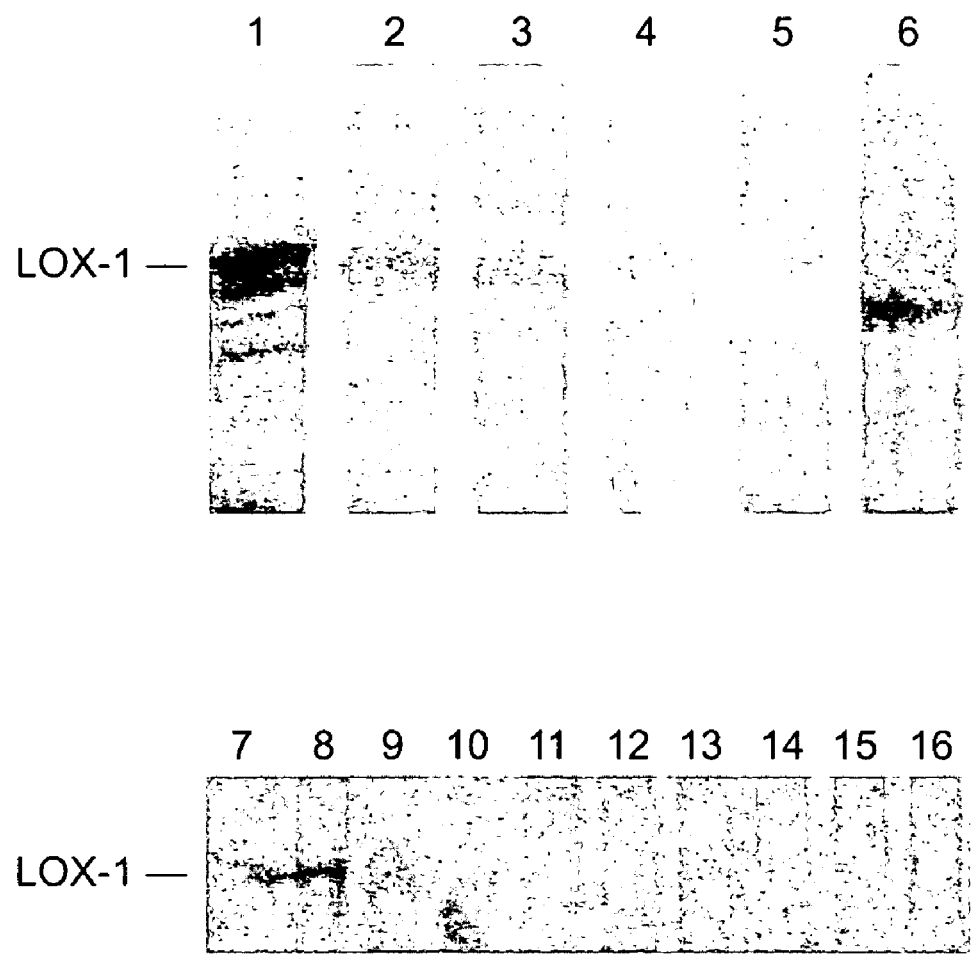

FIG. 7 consists of two separate immunoblots, showing that immunoreactive LOX-1 protein is not detectable in kernel extracts of mutant D112, generation M3. Each immunoblot was probed with an antibody to barley LOX-1, and the samples consisted of extracts of *E. coli* cells expressing recombinant LOX-1 (lane 1), kernel extracts of cv. Vintage (lane 2), mutant line G (lane 3 and lane 7), cv. Barke (lane 6 and lane 8), and separate lines of mutant D112, generation M3 (lanes 4-5 and 9-16). The position of an immunoreactive LOX-1 protein is indicated.

Figure 8:
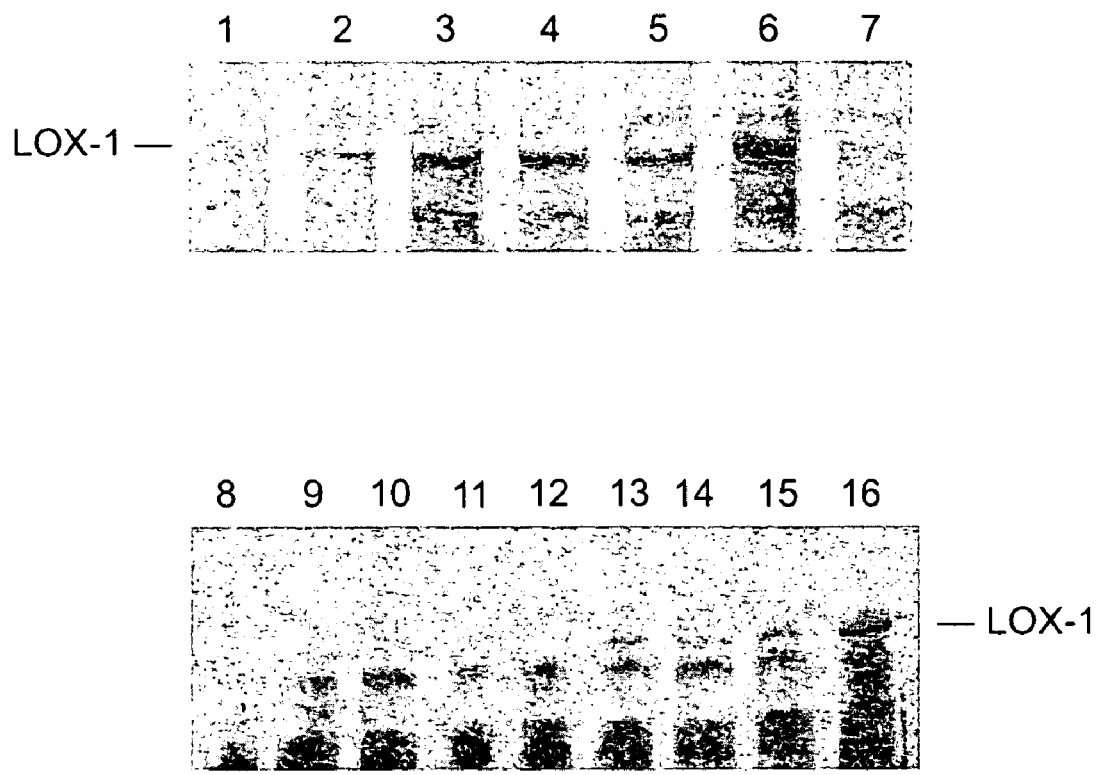

FIG. 8 shows two separate immunoblots, detailing the absence of LOX-1 in kernel extracts of mutant A618, generations M3 and M4. Each immunoblot was probed with an antibody to barley LOX-1, and the samples consisted of kernel extracts of mutant line G (lane 1), cv. Neruda (lane 6 and lane 16). Extracts of randomly chosen M3 and M4 kernels that have not been through the LOX selection procedure were separated in lanes 2-5 and 8-12, respectively; all of these extracts contained a LOX-1 immunoreactive protein. The null-LOX-1 phenotype of a kernel extract of mutant A618, generation M3 (lane 7), was inherited in separate M4-progeny lines of mutant A618-82 (lanes 8-12). The position of an immunoreactive LOX-1 protein is indicated.

Figure 9:
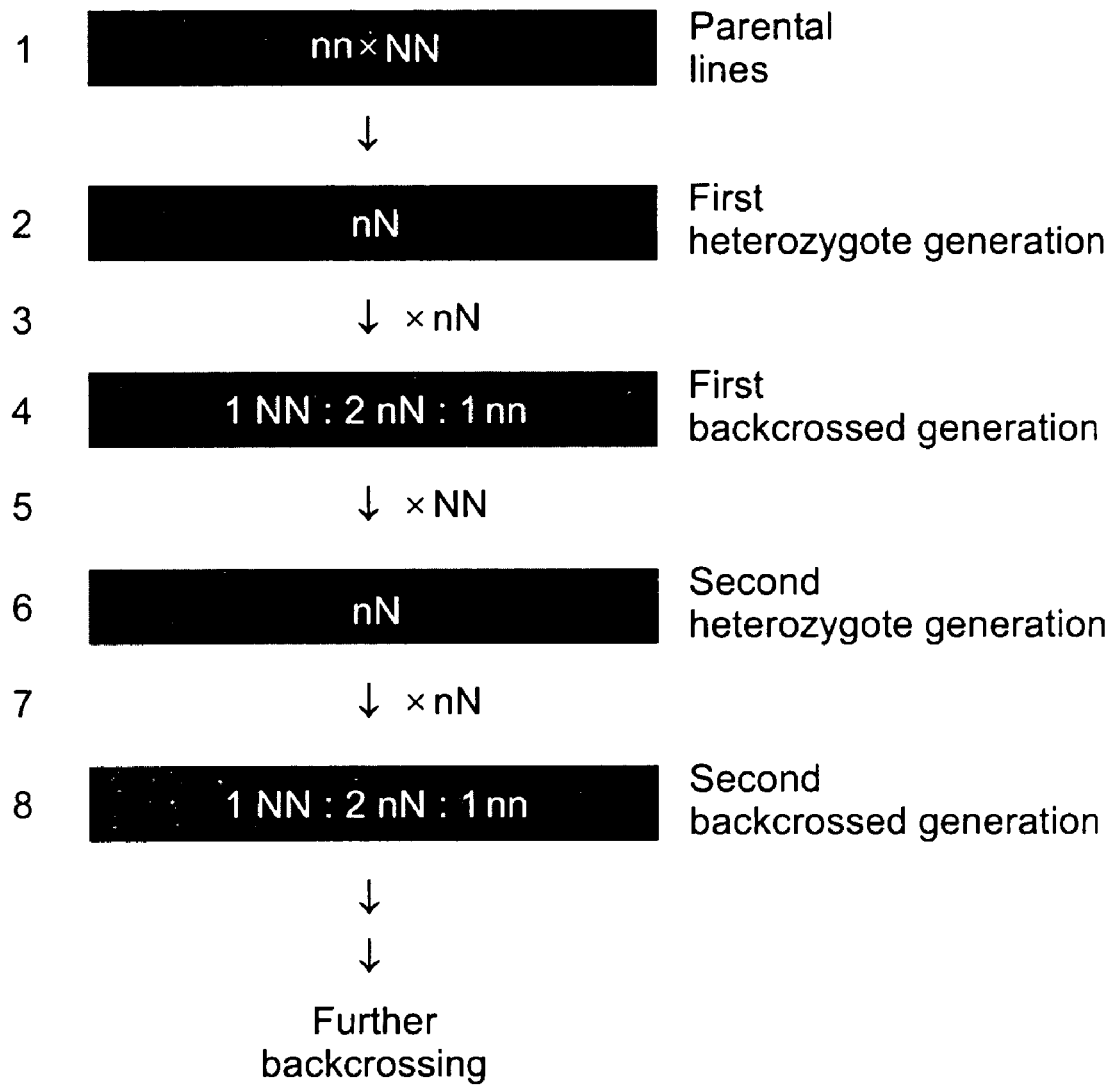

FIG. 9 schematically illustrates the genetics of the backcrossing program for mutant D112 to cv. Prestige. The wild-type LOX-1 trait is assigned NN, while the null-LOX-1 mutant trait is nn.

Figure 10:
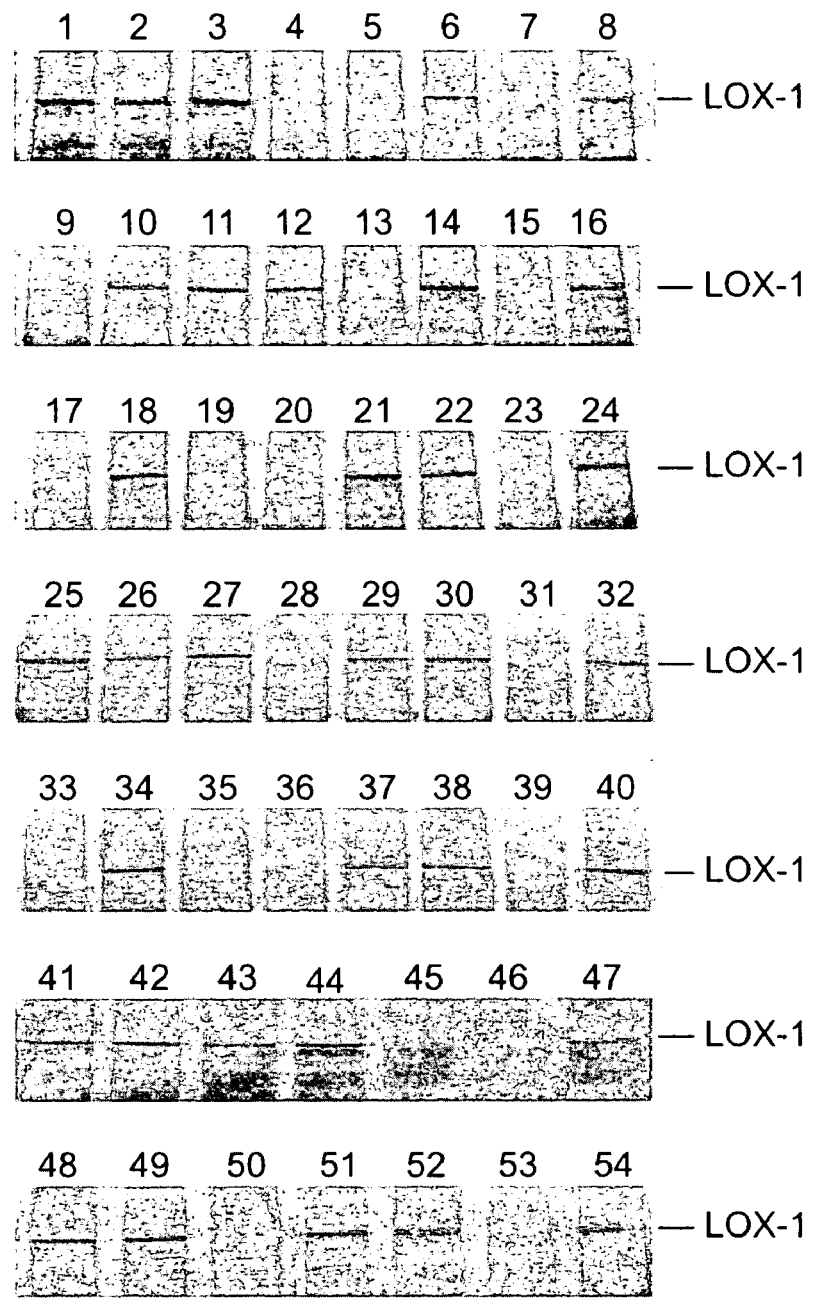

FIG. 10 provides an illustration of seven separate immunoblots, each probed with an antibody to barley LOX-1. The immunoblots show the presence or absence of the immunoreactive LOX-1 protein in kernels of separate plants of the first backcross generation of mutant D112 to cv. Prestige (lanes 1-6 and lanes 9-14), and the presence or absence of the immunoreactive LOX-1 protein in kernels of the second backcross generation of mutant D112 to cv. Prestige (lanes 17-22, lanes 25-30, lanes 33-38, lanes 41-45, and lanes 48-52). Control kernel extracts of mutant D112, lacking immunoreactive LOX-1 (lanes 7, 15, 23, 31, 39, 46, 53), and cv. Prestige, containing immunoreactive LOX-1 (lanes 8, 16, 24, 32, 40, 47, 54), were used as controls. The position of an immunoreactive LOX-1 protein is indicated.

Figure 11:
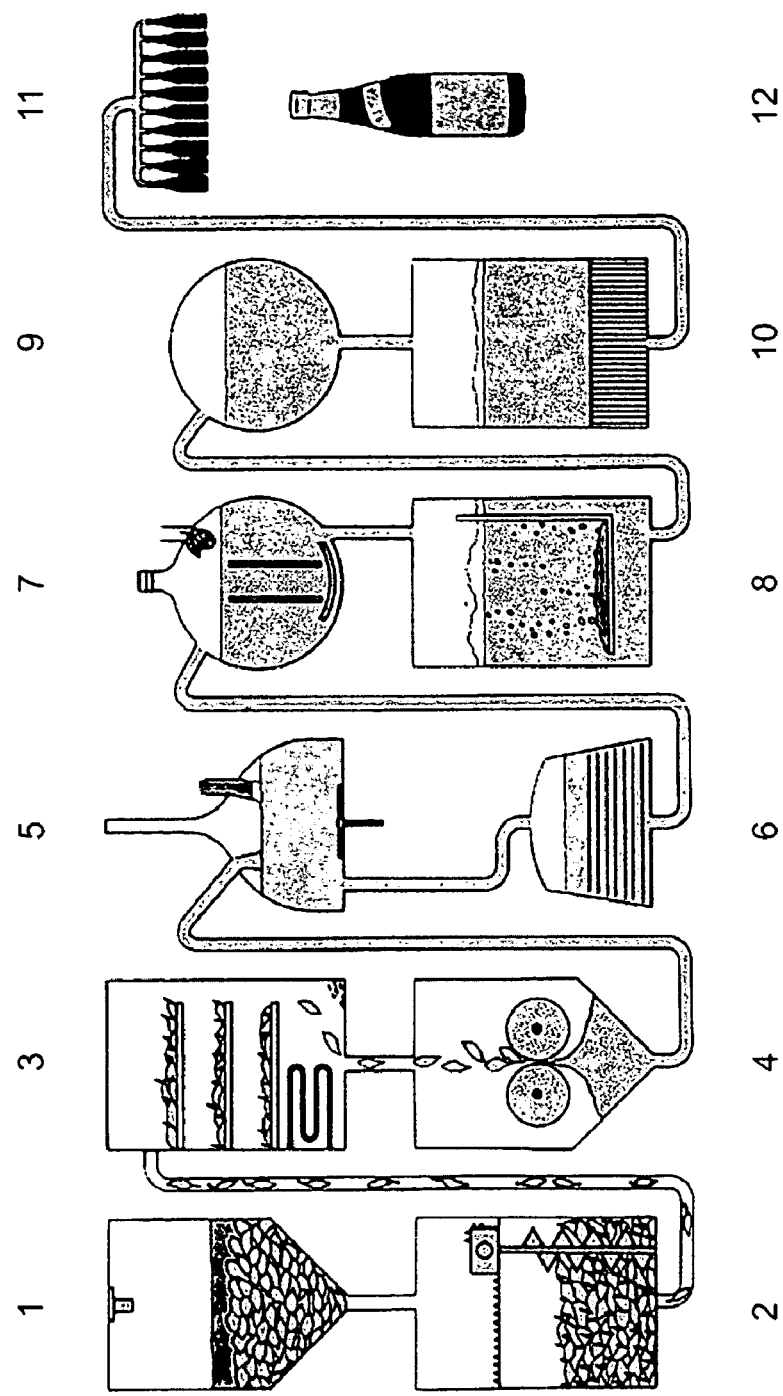

FIG. 11 is a simplified, schematic overview of the beer production process without the use of adjuncts, but including steeping of the barley grain (1), malting (2), kiln drying (3), milling of the dried malt (4), mashing (5), filtration (6), wort boiling in the presence of added hops (7), fermentation in the presence of yeast (8), beer maturation (9), beer filtration (10), bottling (11), and labeling (12). The individual processes can be grouped into sections comprising malt production (1-3), wort production (4-7), fermentation (8-9), and preparation of the finished beer (10-12).

Figure 12:
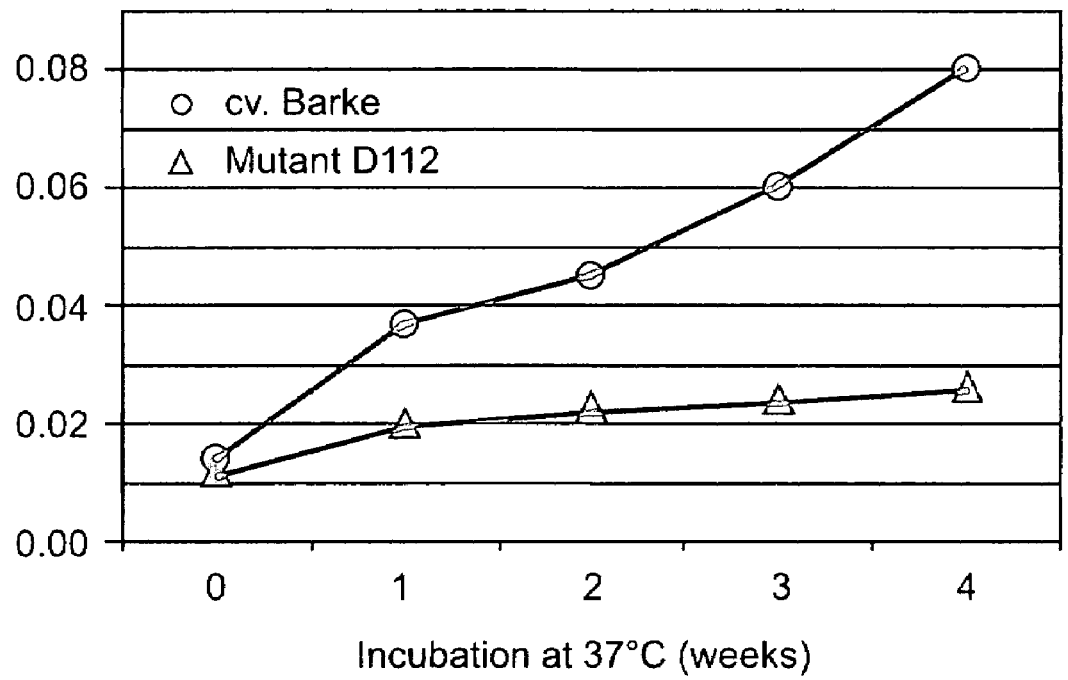

FIG. 12 focuses on graphs showing the accumulation of free T2N during forced aging at 37° C. The aldehyde was measured in beer produced from malt of null-LOX-1 mutant D112 (Δ), and control malt of cv. Barke (o). The taste threshold level for T2N in beer is approximately 0.05 ppb.

FIG. 13 displays the chromatograms of HPLC analyses used to assay for the formation of 9- and 13-HPODEs in barley tissues. The levels of HPODEs were analyzed by measuring the absorbance at 234 nm, with the results given in milli absorbance units (mAU). Peaks of the elution profiles that correspond to 9-HPODE and 13-HPODE are indicated by arrows. FIG. 13A shows the chromatogram of 9-HPODE and 13-HPODE standards. FIG. 13B is a chromatogram of HPODEs formed in extracts prepared from mature embryos of cv. Barke. FIG. 13C is a chromatogram of HPODEs formed in extracts prepared from mature embryos of low-LOX kernels. FIG. 13D is a chromatogram of HPODEs formed in extracts of mature embryos of the null-LOX-1 mutant D112.

FIG. 14 depicts the chromatograms of HPLC analyses used to assay for the formation of 9- and 13-HPODEs in malt. The levels of said HPODEs were analyzed by measuring the absorbance at 234 nm, with the results given in milli absorbance units (mAU). Peaks of the elution profiles that correspond to 9-HPODE and 13-HPODE are indicated by arrows.

Figure 14A:
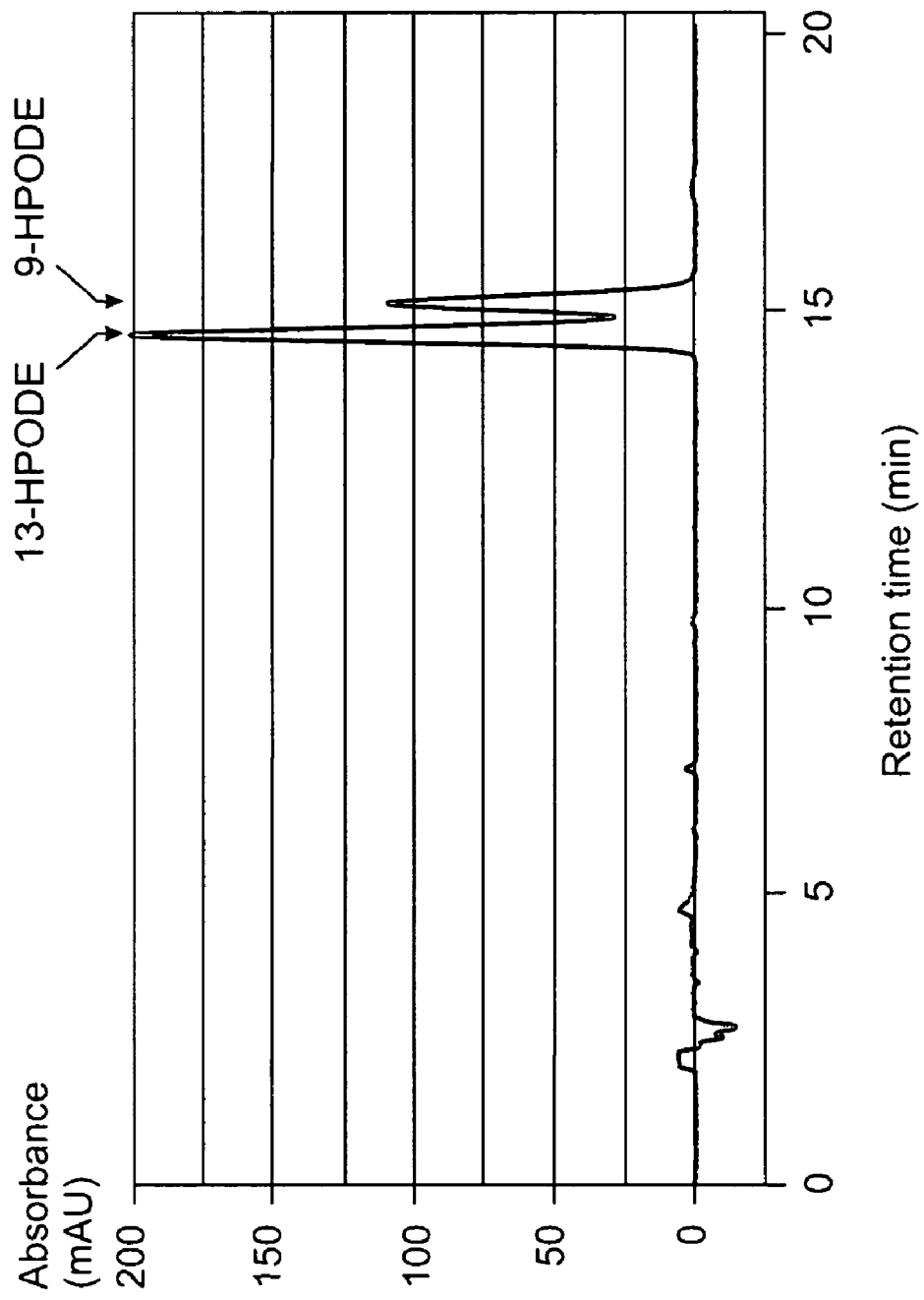
Figure 14B:
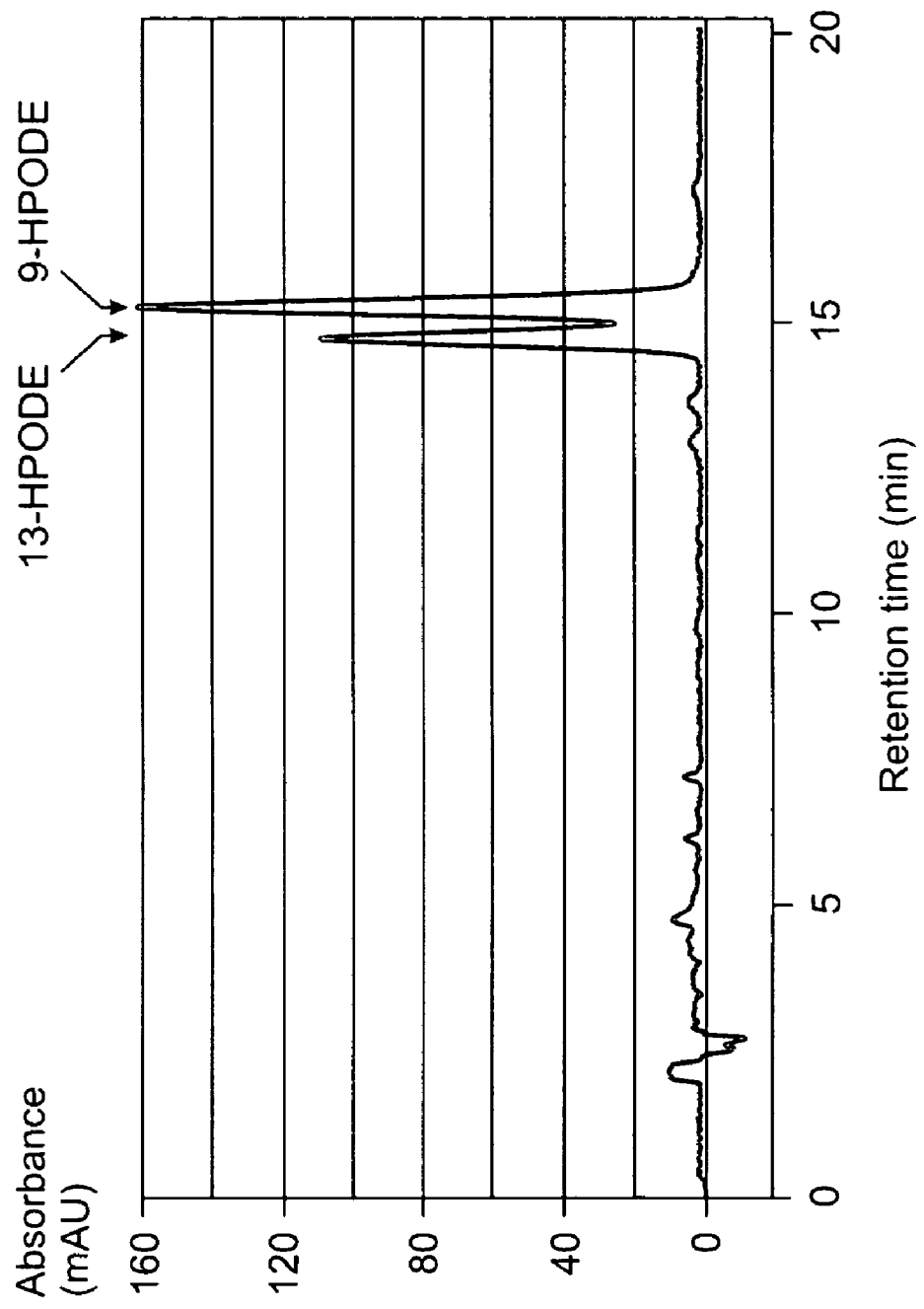
Figure 14C:
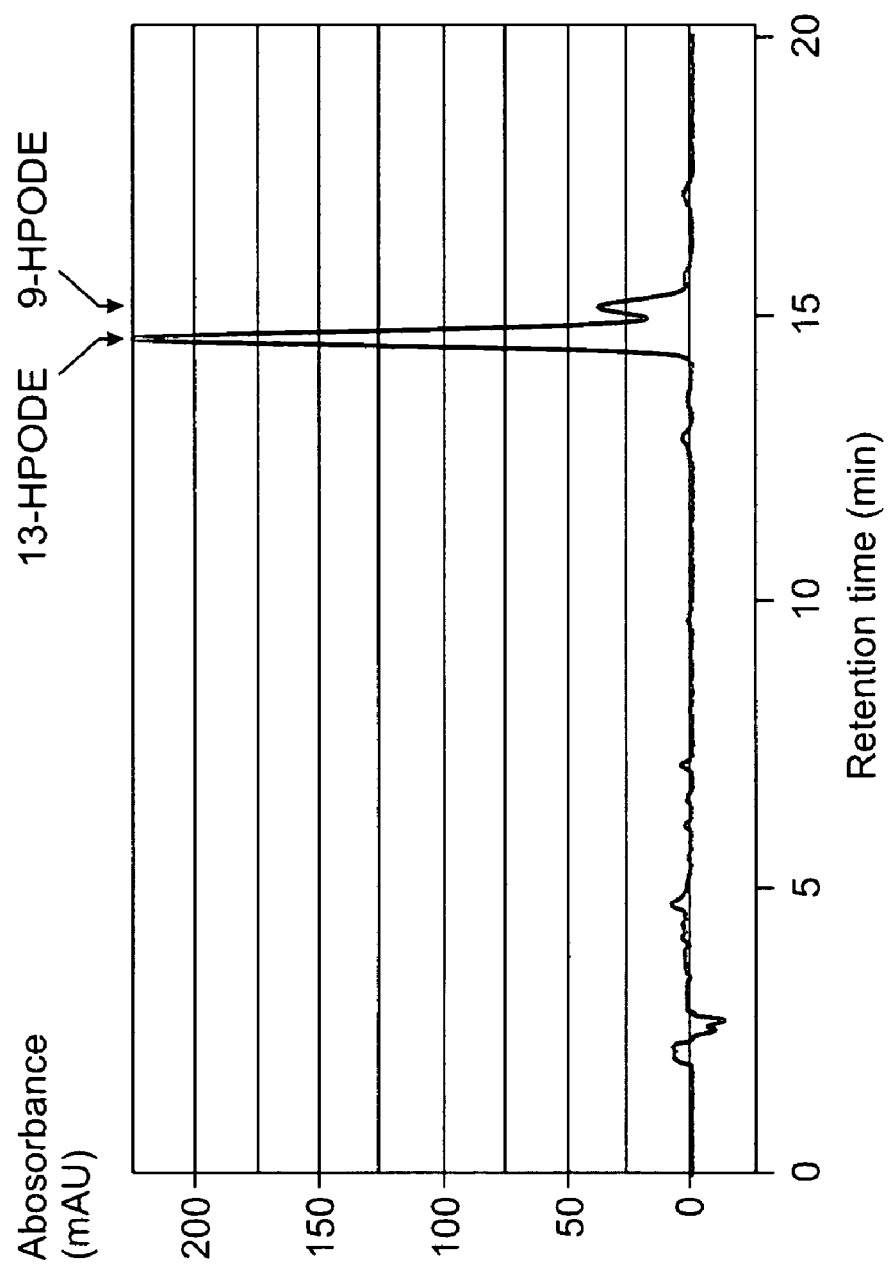
Figure 14D:
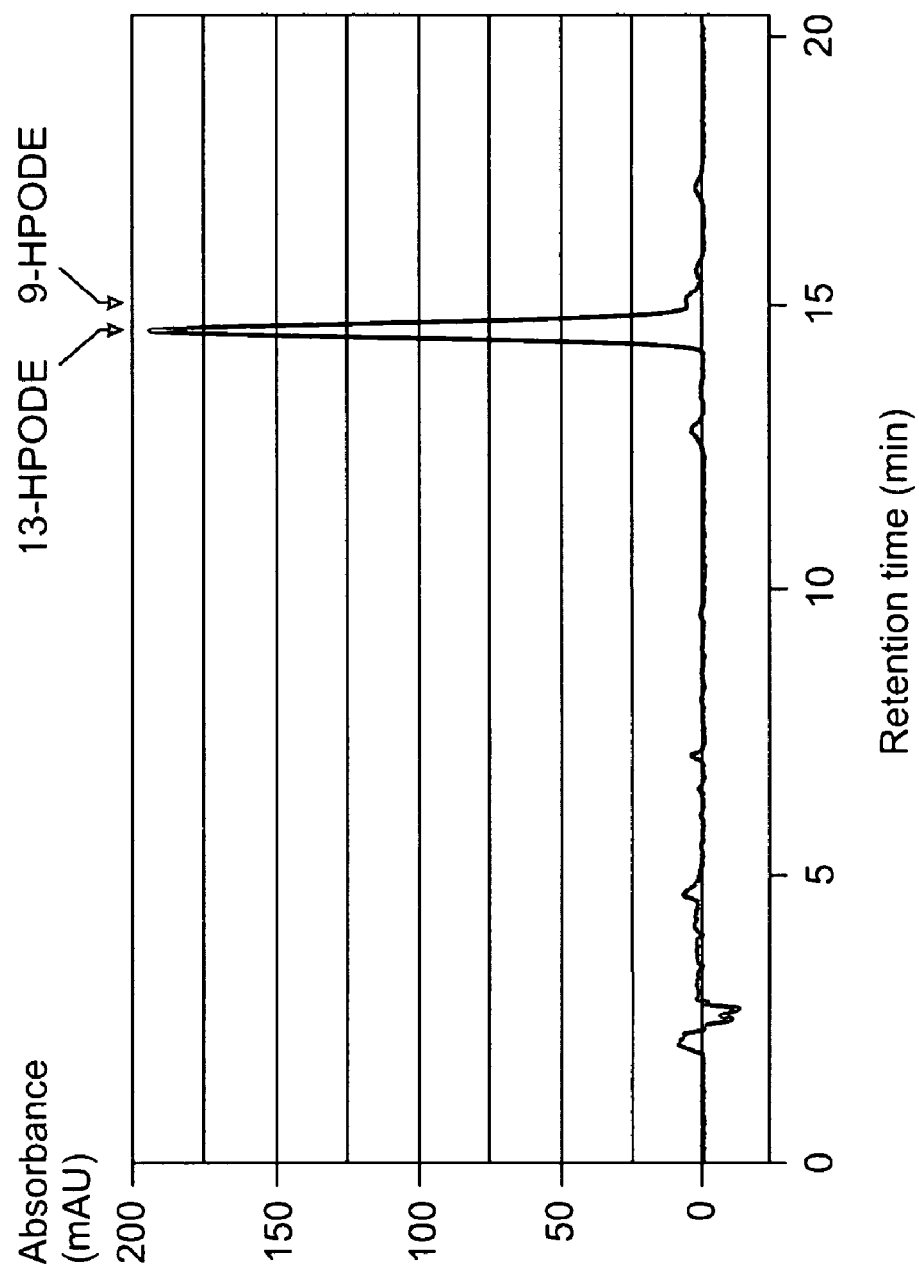

FIG. 14A shows the chromatogram of 9-HPODE and 13-HPODE standards. Chromatogram peaks corresponding to 9-HPODE and 13-HPODE are indicated by arrows. FIG. 14B is a chromatogram of HPODEs formed in extracts of malt from cv. Barke. FIG. 14C is a chromatogram of HPODEs formed in extracts of malt from low-LOX barley. FIG. 14D is a chromatogram of HPODEs formed in extracts of malt from the null-LOX-1 mutant D112.

Figure 15:
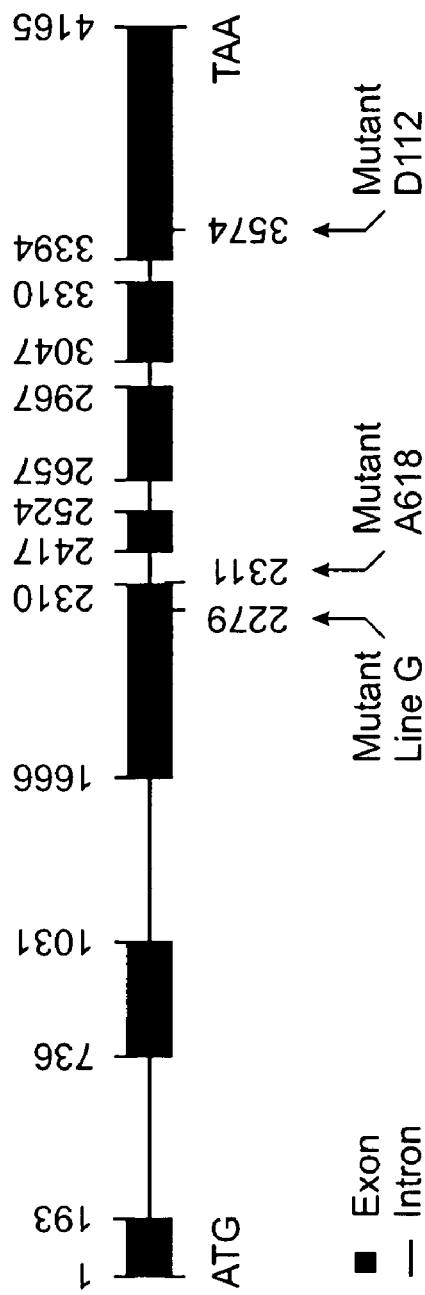

FIG. 15 is a map showing the organization of the gene for barley LOX-1, spanning the start codon (ATG) and stop codon (TM). The schematic drawing of the 4,165-bp-long sequence shows 7 exons (filled boxes) and 6 introns (lines). The position of the mutations identified in the gene for LOX-1—i.e. specific for mutant line G (low-LOX), mutant A618 and mutant D112—are indicated by arrows.

FIG. 16 summarizes the predicted molecular differences related to the gene for LOX-1 of wild-type, mutant A618 and mutant D112 barley plants. The information listed in the columns marked "Result," "Length in amino acids," and "Mass in kDa" is predicted from the DNA sequence.

Figure 17:
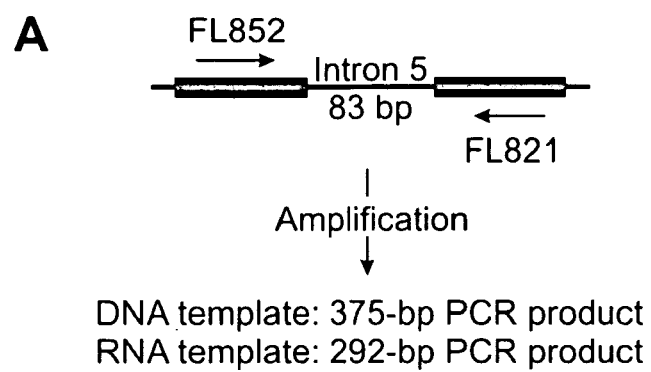
Figure 17:
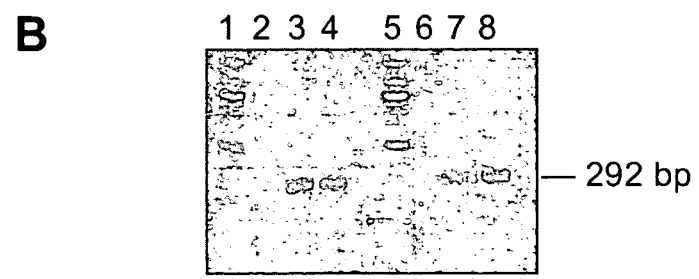
Figure 17:
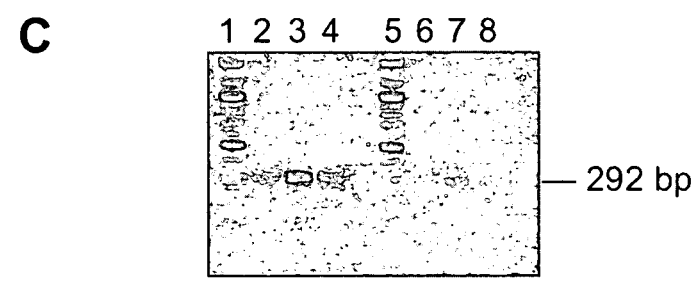
Figure 17:
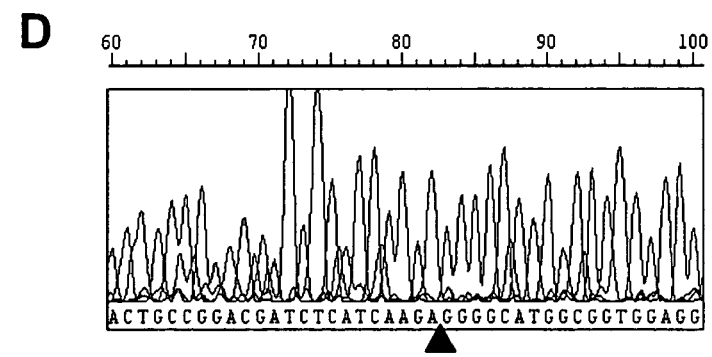

FIG. 17 provides ways used to perform RT-PCR mutant analysis and transcript verification related to the barley gene encoding LOX-1. In A is shematically shown the principle for RT-PCR detection of a specific transcript for the gene encoding LOX-1 in developing embryos of cv. Vintage and low-LOX-1 mutant line G. Primers consisted of FL821 [SEQ ID NO: 11] and FL852 [SEQ ID NO: 12], which anneal in the exons flanking the 83-bp-long intron 5; PCR product differences using either genomic DNA or mRNA templates are indicated. In B is shown the result of a RT-PCR agarose gel analysis, where focus was on the detection of a specific transcript related to the gene encoding LOX-1 in developing embryos of barley, cv. Vintage and mutant line G. Lanes 1 and 5 contained marker fragments, and lanes 2, 3, and 4 contained the PCR products derived from embryo tissues of cv. Vintage after 20, 40, and 60 days after flowering (DAF), respectively. Lanes 6, 7 and 8 contain the products derived from embryo tissues of mutant line G after 20, 40, and 60 DAF, respectively. In C, lanes 1-5 show the result of an experiment similar to that detailed for lanes 1-5 in B, while lanes 6, 7 and 8 contained the products derived from RT-PCR detection of a mutant D112 embryo-specific transcript of the gene for LOX-1 after 20, 40, and 60 DAF, respectively. In D is shown an electropherogram that resulted from a sequencing reaction of a RT-PCR fragment specific for the gene for LOX-1. Sequence analysis revealed that the RT-PCR target RNA was free of DNA. The black triangle points to the splice point, indicating correct splicing of the transcript.

Figure 18:
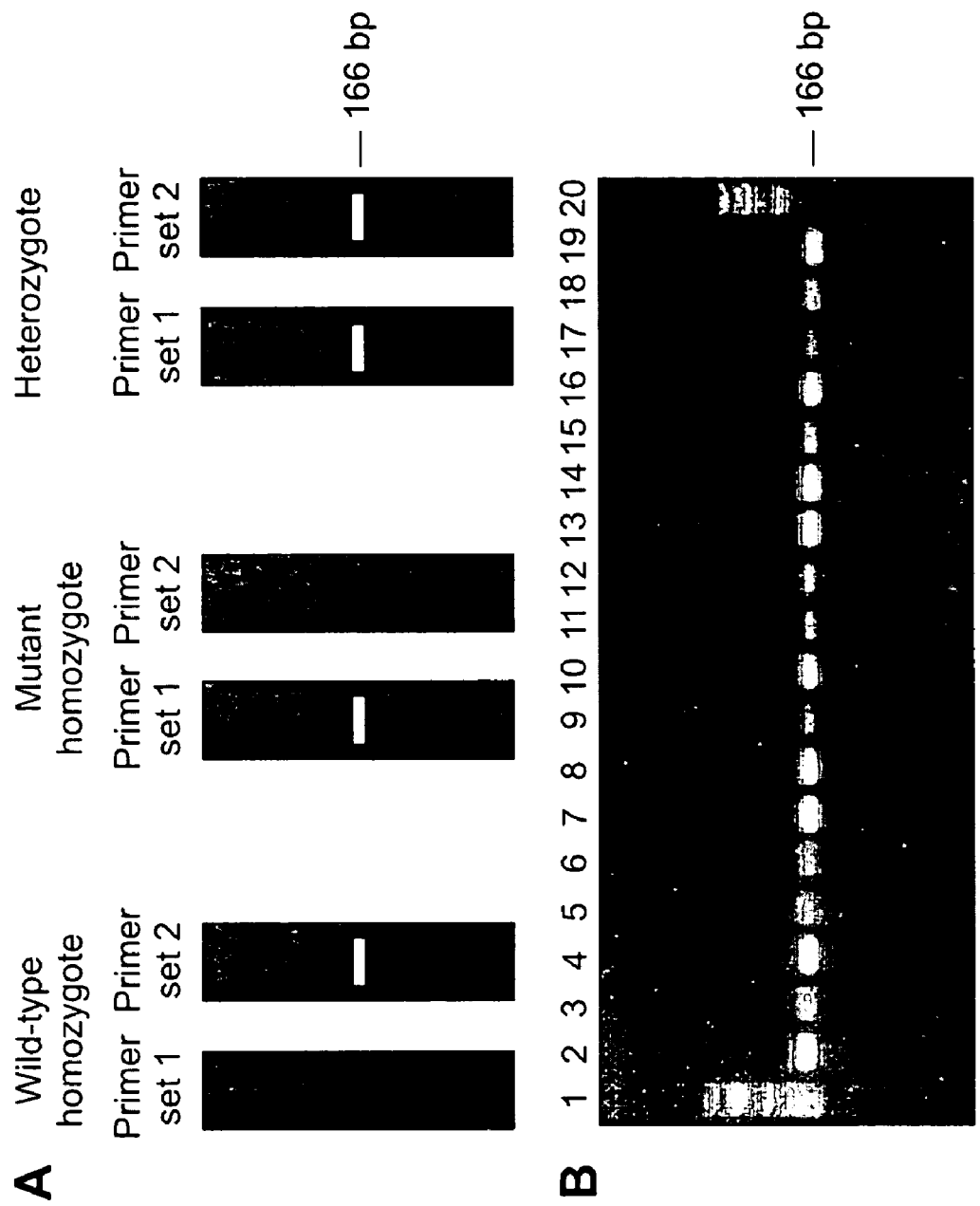

FIG. 18 details the results of a SNP-assisted detection of barley mutant D112. The analysis was based on the generation of a specifc PCR fragment pattern using two sets of PCR reactions per sample, as schematically illustrated in A (primer set 1 consists of FL820 [SEQ ID NO: 13] and primer FL823 [SEQ ID NO: 15], and primer set 2 consists of FL820 [SEQ ID NO: 13] and FL825 [SEQ ID NO: 14]). In B is shown the result of a PCR pattern analysis of elite breeding material. Genomic DNA of plants were subjected to PCR analyses. Results shown in lanes 2-3 (plant 1), 4-5 (plant 2), 6-7, (plant 3), 8-9 (plant 4), 10-11 (plant 5), 12-13 (plant 6), 14-15 (plant 7), 16-17 (plant 8), and 18-19 (plant 9) utilized primer combination 1 (even numbered lanes) or primer combination 2 (odd numbered lanes). Comparison of the banding pattern with that shown in A revealed that plants 1, 2, 4, 5, 7, and 8 were homozygous mutants, while the genotype of plants 3, 6, and 9 could be classified as homozygous wild-type. Marker DNA was separated in lanes 1 and 20.

Figure 19:
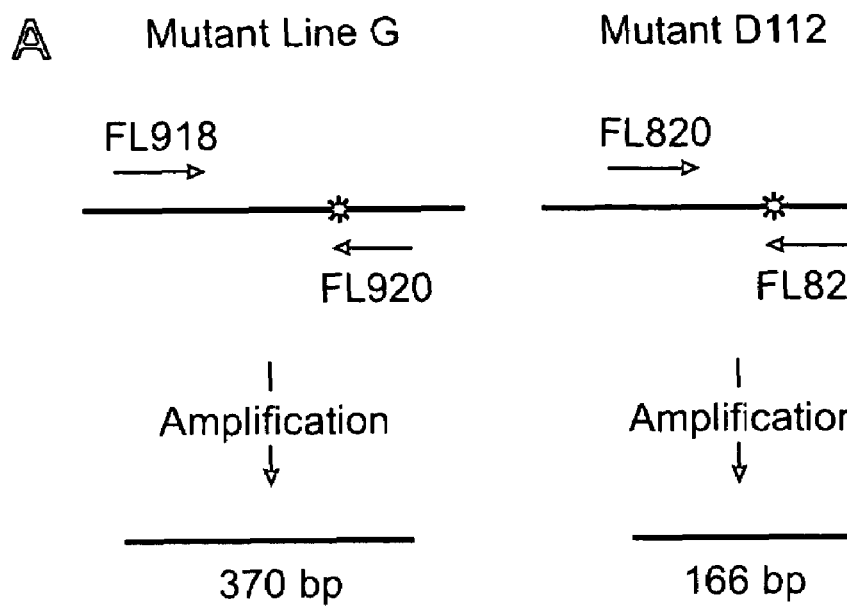
Figure 19:
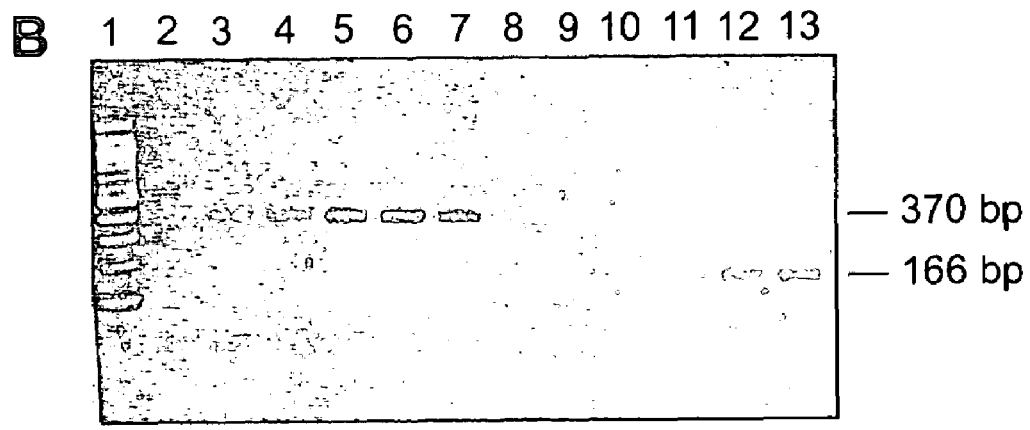

FIG. 19 demonstrates the principle of multiplex SNP analysis of barley samples containing material of mutant G or mutant D112. The analysis utilized multiplex PCR reactions, such that the length of the fragment amplified could be related to the genotype of the material added. Amplification of a 370-bp fragment would indicate that a malt sample contained material derived from mutant line G, while the amplification of a 166-bp fragment would point to the presence of material derived from mutant D112. Panel A is a schematic illustration detailing how specific primer pairs, each with one primer that contains a sequence which is specific for the mutant of interest (asterisk; for mutant line G nucleotide number 2279 in the genomic clone for LOX-1, and for mutant D112 position 3574). The primer combination FL918 [SEQ ID NO: 16] and FL920 [SEQ ID NO: 17] was used for detection of the mutant line G-specific mutation, while FL820 [SEQ ID NO: 13] and FL823 [SEQ ID NO: 15] were utilized for detection of the mutant D112-specific base change. In B is shown how the relative quantities of mutant-specific material (lanes 2-7: mutant line G; lanes 8-13: mutant D112) in samples may enhance the synthesis of a specific PCR fragment (lanes 2 and 8: no mutant material added; lanes 3 and 9: 20% mutant material added; lanes 4 and 10: 40% mutant material added; lanes 5 and 11: 60% mutant material added; lanes 6 and 12: 80% mutant material added; lanes 7 and 13: 100% mutant material). Lane 1 consisted of marker fragments.

Figure 20:
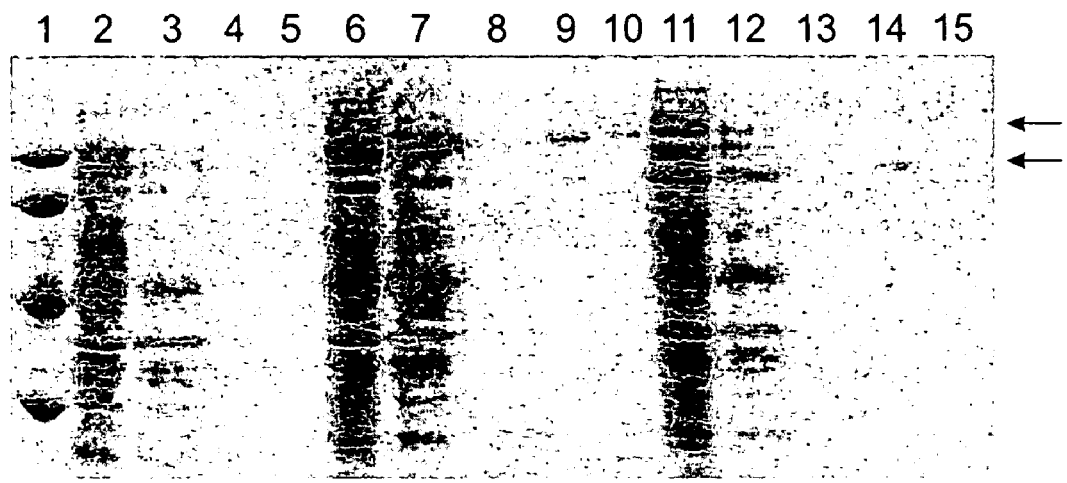

FIG. 20 presents the result of SDS-PAGE of affinity-purified, His-tagged LOX-1 from *E. coli* cells transformed with the vector plasmid pET19b (lanes 2-5), expression plasmid pETL1 (lanes 6-10), and expression plasmid pETL2 (lanes 11-15). Proteins from fractions comprising unbound proteins (lanes 2, 6, 11); first wash (lanes 3, 7, 12); second wash (lanes 4, 8, 13); first eluate (lanes 5, 9, 14); and second eluate (lanes 10 and 15) were analyzed. The upper arrow indicates the position of recombinant LOX-1 (corresponding to wild-type LOX-1), while the lower arrow indicates the postion of truncated, recombinant LOX-1 (corresponding to LOX-1 in barley mutant D112). Lane 1 comprised separated marker proteins.

Figure 21:
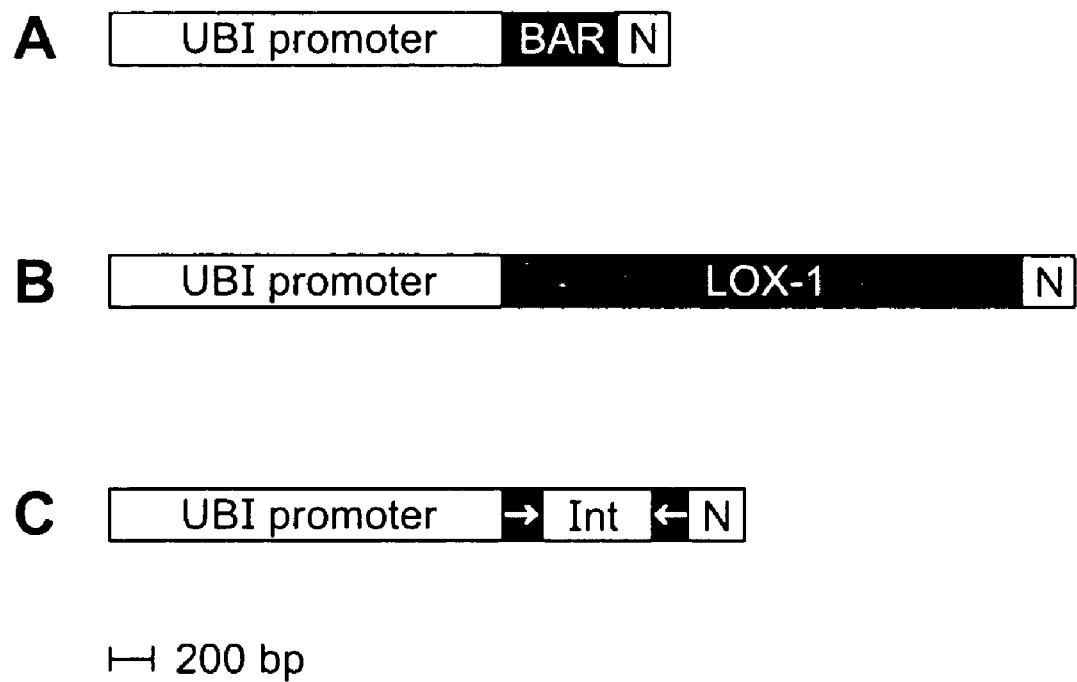

FIG. 21 illustrates plasmid inserts for transformation of barley. In A is illustrated an expression cassette consisting of the maize ubiquitin-1 promoter and intron 1 (collectively denoted the UBI promoter), directing constitutive expression of the bar gene (BAR), which encodes the selectable marker phosphinothricin acetyl transferase. Transcription termination is provided by the NOS terminator sequence (N). In B is illustrated an expression cassette consisting of the aforementioned UBI promoter, here directing constitutive expression of the barley cDNA sequence for LOX-1 in sense or antisense orientation. In C is illustrated an expression cassette consisting of the UBI promoter directing constitutive expression of a intron-containing hairpin construct, where the sequence of intron 1 of the *Arabidopsis* gene for fatty acid desaturase FAD2 intron 1 (Int), flanked by the sense arm (→) and antisense arm (←) of an approximately 200-bp-long fragment of the gene for LOX-1. Transcription termination is provided by the NOS terminator sequence (N). For the generation of barley plants exhibiting co-suppression of the gene for LOX-1, plasmid mixtures are used that comprise equal amounts of expression plasmids comprising the inserts detailed in A and B. For the generation of barley plants exhibiting total silencing of the gene for LOX-1, mixtures are used that comprise equal amounts of expression plasmids comprising the inserts in A and C.

6. DETAILED DESCRIPTION OF THE INVENTION

For purposes of clarity of description, and not by way of limitation, the detailed description of the invention is divided into the following subsections:
(i) Barley plant;
(ii) Preparing null-LOX-1 barley;
(iii) Composition;
(iv) Chemical mutagenesis;
(v) Selection of barley mutants;
(vi) Plant breeding;
(vii) Barley crossings;
(viii) LOX enzymes;
(ix) LOX pathway products;
(x) T2N potential;
(xi) Disease resistance;
(xii) Mycotoxins;
(xiii) Fragrances;
(xiv) Heterologous expression of genes encoding LOX.

6.1 Barley plant

The present invention relates to barley plants and parts thereof comprising less than 1% of the LOX-1 activity of a wild-type barley plant. The barley plants of the invention comprising less than 1% LOX-1 activity are herein also referred to as "null-LOX-1 barley plants."

The barley plant may be in any suitable form. For example, the barley plant according to the invention may be a viable barley plant, a dried plant, a homogenized plant, such as milled barley kernels. The plant may be a mature plant, an embryo, a germinated kernel, a malted kernel or the like.

Parts of barley plants may be any suitable part of the plant, such as kernels, embryos, leaves, stems, roots, flowers or fractions thereof. Fractions may for example be a section of a kernel, embryo, leaves, stem, root or flower. Parts of barley plants may also be a fraction of a homogenate or milled barley plant or kernel.

In one embodiment of the invention, parts of barley plants may be cells of said barley plant, preferably viable cells, that may be propagated in tissue cultures in vitro.

In a preferred embodiment of the invention, null-LOX-1 barley plants comprise less than 5%, preferably less than 3%, more preferably less than 1%, preferably less than 0.5%, even more preferably less than 0.1% of the activity of a wild-type barley plant. The activity may be determined by any suitable method, preferably however, the activity is determined using the method in Example 1 herein below. In a very preferred embodiment of the invention, the null-LOX-1 barley plants have essentially no LOX-1 activity, more preferably no LOX-1 activity at all. "Essentially no LOX-1 activity" means no detectable LOX-1 activity using an assay for LOX-1 activity as described herein below.

The almost absent LOX-1 activity of the null-LOX-1 barley may for example be the result of that said barley comprises a malfunctioning LOX-1 protein, such as a mutant LOX-1 protein. However, the null-LOX-1 barley comprises only very little or, more preferably, no LOX-1 protein, such as less than 5%, preferably less than 3%, more preferably less than 1%, preferably less than 0.5%, more preferably less than 0.1% LOX-1 protein compared to a wild-type barley plant. More preferably, the null-LOX-1 barley comprises essentially no LOX-1 protein, most preferably no LOX-1 protein at all. "Essentially no LOX-1 protein" is meant to cover no detectable LOX-1 protein. The LOX-1 protein may be detected by any suitable means known to the person skilled in the art, however, preferably the protein is detected by techniques wherein LOX-1 protein is detected by specific antibodies to LOX-1. Said techniques may for example be Western blotting or ELISA. Said specific antibodies may be monoclonal or polyclonal, preferably however, said antibodies are polyclonal recognizing several different epitopes within the LOX-1 protein. LOX-1 protein may also be detected indirectly, for example by methods determining LOX-1 activity, by methods detecting mutations in the gene encoding LOX-1 or by methods detecting expression of the LOX-1 gene. Mutations in the gene encoding LOX-1 may for example be detected by sequencing said gene. Expression of the gene for LOX-1 may for example be detected by Nothern blotting or RT-PCR. In one preferred embodiment of the invention, LOX-1 protein is detected using the methods outlined in Example 4 of the instant publication.

The term LOX-1 protein is meant to cover the full length LOX-1 protein of barley as set forth in [SEQ ID NO: 3] or [SEQ ID NO: 7] or a functional homologue thereof. The active site of LOX-1 is situated in the C-terminal part of LOX-1. In particular is the region spanning amino acid residues 520-862 or parts thereof relevant for LOX-1 activity. Accordingly, in one embodiment null-LOX-1 barley preferably comprises a gene encoding a mutant form of LOX-1 lacking some or all of amino acids 520-862 of LOX-1. Said mutant LOX-1 may also lack other amino acid residues which are present in wild-type LOX-1.

Accordingly, null-LOX-1 barley may comprise a truncated form of LOX-1, which is not functional, such as an N-terminal or a C-terminal truncated form. Preferably, said truncated form comprises no more than 800, more preferably no more than 750, even more preferably no more than 700, yet more preferably no more than 690, even more preferably no more than 680, yet more preferably no more than 670 consecutive amino acids of LOX-1, such as no more than 665, for example no more than 650, such as no more than 600, for example no more than 550, such as no more than 500, for example no more than 450, such as no more than 425, for example no more than 399 consecutive amino acids of LOX-1 of [SEQ ID NO: 3]. Preferably, said truncated form comprises only an N-terminal fragment of LOX-1. Hence, preferably said truncated form comprises at the most the 800, more preferably at the most the 750, even more preferably at the most the 700, yet more preferably at the most the 690, even more preferably at the most the 680, yet more preferably at the most the 670, even more preferably at the most the 665 N-terminal amino acids of [SEQ ID NO: 3], such as no more than 665, for example no more than 650, such as no more than 600, for example at the most the 550, such as at the most the 500, for example at the most the 450, such as at the most the 425, for example at the most the 399 N-terminal amino acids of [SEQ ID NO: 3].

In one very preferred embodiment, the truncated form may consist of amino acid 1-665 of [SEQ ID NO: 3].

In a preferred embodiment of the invention, the barley plant comprises a gene transcribed into mRNA encoding LOX-1, wherein said mRNA comprises a nonsense codon or a stop codon upstream of the stop codon of wild-type LOX-1 mRNA. Such a nonsense codon is herein designated a premature nonsense codon. Preferably all genes transcribed into mRNA encoding LOX-1 of said plant comprise a premature non-sense codon or a stop codon. The non-sense codon or stop codon is preferably situated at the most 800, more preferably at the most the 750, even more preferably at the most the 700, yet more preferably at the most the 690, even more preferably at the most the 680, yet more preferably at the most the 670, even more preferably at the most the 665 codons down-stream of the start codon. The sequence of wild-type genomic DNA encoding LOX-1 is given in [SEQ ID NO: 1] or [SEQ ID NO: 5].

In one preferred embodiment the barley plant comprises a gene encoding LOX-1, wherein pre-mRNA transcribed from said gene comprises the ribonucleic acid sequence corresponding to [SEQ ID NO: 2].

In another preferred embodiment of the invention, the barley plant comprises a gene encoding mutant LOX-1 wherein said gene comprises at least one, such as 1, for example 2, such as 3, for example 4, such as 5 mutations in at least one, such as 1, for example 2, such as 3 splice sites. Preferably, said mutation(s) results in that said at least one splice site is non-functional. mRNA transcribed from such a gene will thus be abnormal due to aberrant splicing. Accordingly, it is preferred that mRNA transcribed from the LOX-1 gene of the null-LOX-1 barley plant according to the invention encodes no protein or a protein comprising only the N-terminus of LOX-1. Said protein may comprise other sequences encoded by the abnormal mRNA, which are not derived from the gene for LOX-1. In this context, the N-terminus of LOX-1 comprises amino acid 1 to amino acid N, wherein N is an integer in the range of 2 to 800, more preferably in the range of 2 to 750, yet more preferably in the range of 2 to 700, even more preferably in the range of 2 to 650, yet more preferably in the range of 2 to 600, even more preferably in the range of 2 to 550, yet more preferably in the range of 2 to 500, yet more preferably in the range of 2 to 450, even more preferably in the range of 2 to 400, yet more preferably in the range of 2 to 378.

In one embodiment of the invention the barley plant comprises a gene encoding a mutant LOX-1, wherein said gene has a mutation in a splice site leading to mRNA encoding a protein consisting of amino acids 1 to 378 of [SEQ ID NO: 3] as well as an additional amino acid sequence not derived from LOX-1. Preferably, said mutant LOX-1 consists of the sequence as outlined in [SEQ ID NO: 8].

In a very preferred embodiment of the invention the gene encoding mutant LOX-1 of the null-LOX-1 barley plant comprises a nonsense mutation, said mutation corresponding to a G→A substition at position 3574 of [SEQ ID NO: 1]. More preferably the null-LOX-1 barley plant is a plant designated D112 having American Type Culture Collection (ATCC) deposit accession No. PTA-5487.

In another very preferred embodiment of the invention the gene encoding LOX-1 of the null-LOX-1 barley plant comprises a non-functional intron 3 donor splice site. LOX-1 mRNA of said plant thus encodes a protein containing amino acids 1-378 of LOX-1 and additional amino acids from intron 3, comprised in [SEQ ID NO: 8]. More preferably, the null-LOX-1 barley plant is a plant designated A618 having American Type Culture Collection (ATCC) deposit accession No PTA-5584.

The barley plants according to the invention may also be the progeny of a null-LOX barley plant. Hence, the barley plant may be the progeny of the plant designated D112 having ATCC deposit accession No. PTA-5487 or the plant designated A618 having ATCC deposit accession No. PTA-5584.

The barley plant according to the invention may be prepared by any suitable method known to the person skilled in the art, preferably by one of the methods outlined herein below (see for example Section 6.2 "Preparing null-LOX-1 barley").

In one embodiment of the invention it is preferred that the null-LOX-1 barley plant according to the present invention has plant growth physiology and grain development comparable to wild-type barley. It is hence preferred that the null-LOX-1 barley plant is similar to wild-type barley in respect of plant height, number of tillers per plant, onset of flowering and/or number of grains per spike.

It is also an aspect of the invention to provide a null-LOX-1 barley plant, wherein said plant is characterized by:
(i) having enhanced disease resistance; or
(ii) having reduced potential for the production of mycotoxins; or
(iii) comprising regenerable cells for use in tissue culture; or
(iv) any combination of the traits of (i) to (iii).

6.2 Preparing Null-LOX-1 Barley

The barley plant according to the invention may be prepared by any suitable method known to the person skilled in the art. Preferably, the barley plant of the invention is prepared by a method comprising the steps of mutagenizing barley plants or parts thereof, for example barley kernels, followed by screening and selecting barley plants for plants with less than 5% LOX-1 activity. Interestingly, the present invention in one aspect relates to a new and very efficient screening method, significantly superior to the screening method described in for example WO 02/053721 to Douma et al. The new screening method allows reproducibly to identify barley plants with no or very little LOX-1 activity. This new screening method includes obtaining kernels or parts thereof, such as embryos, from mutagenized barley and determining the LOX-1 activity in said kernels or parts thereof.

Accordingly, it is an objective of the present invention to provide methods of preparing a barley plant comprising less than 5% of the LOX-1 activity of a wild-type barley plant comprising the steps of:
(i) Determining the LOX-1 activity in wild-type barley kernels or parts thereof; and
(ii) Mutagenizing barley plants and/or barley cells and/or barley tissue and/or barley kernels and/or barley embryos thereby obtaining generation M0 barley; and
(iii) Breeding said mutagenized barley plants, kernels and/or embryos for at least 2 generations, thereby obtaining generation Mx barley plants, wherein x is an integer $\geq 2$; and
(iv) Obtaining kernels or parts thereof from said Mx barley plants; and
(v) Determining the LOX-1 activity in said kernels or parts thereof; and
(vi) Selecting plants wherein the LOX-1 activity of the mutagenized kernels or parts thereof is less than 5% than the LOX-1 activity of the wild-type kernels or part thereof;

thereby obtaining a barley plant comprising less than 5% of the LOX-1 activity of a wild-type barley plant.

Step (ii) in the above list may involve mutagenizing living material selected from the group consisting of barley plants, barley cells, barley tissue, barley kernels and barley embryos, preferably selected from the group consisting of barley plants, barley kernels and barley embryos, more preferably barley kernels. It is preferred that the LOX-1 activity of mutagenized kernels is determined using the same kind of material as that used for the determination of the LOX-1 activity of wild-type barley kernels, i.e it is preferred that the barley kernel or parts thereof of step (i) is the same kind of barley kernel or parts thereof as that mentioned in step (iv). By way of example, if the LOX-1 activity of wild-type barley is determined in embryos of wild-type barley, it is preferred that step (iv) comprises determining LOX-1 activity in embryos of mutagenized barley plants.

Mutagenesis may be performed by any suitable method. In one embodiment, mutagenesis is performed by incubating a barley plant or a part thereof, for example barley kernels or individual cells from barley with a mutagenizing agent. Said agent is known to the person skilled in the art, for example, but not limited to sodium azide ($NaN_3$), ethyl methanesulfonate (EMS), azidoglycerol (AG, 3-azido-1,2-propanediol), methyl nitrosourea (MNU), and maleic hydrazide (MH).

In another embodiment, mutagenesis is performed by irradiating, for example by UV, a barley plant or a part thereof, such as the kernel. In preferred embodiments of the invention the mutagenesis is performed according to any of the methods outlined herein below in Section 6.4 "Chemical mutagenesis." A non-limiting example of a suitable mutagenesis protocol is given in Example 1.

It is preferred that the mutagenesis is performed in a manner such that the expected frequency of desired mutants is at least 0.5, such as in the range of 0.5 to 5, for example in the range of 0.9 to 2.3 per 10,000 grains, when screening M3 barley.

In a preferred embodiment, mutagenesis is performed on barley kernels. The mutagenized kernels are designated generation M0 (see also FIG. 1A).

Subsequent to mutagenesis, barley plants, or parts thereof, that comprise less than 5%, preferably less than 1% LOX-1 activity are selected. Selection may be performed according to any suitable method known to the person skilled in the art. Preferably, selection comprises obtaining a sample from a barley plant, such as from a barley kernel, determining the activity of LOX-1 in said sample and selecting plants, wherein said sample has less than 5%, or preferably less than 1% of the LOX-1 activity of a wild-type barley plants.

The sample may be taken from any suitable part of said plant. Preferably, however, the sample is taken from the kernel, more preferably the sample is taken from the embryo tissue of a kernel, yet more preferably the sample consists of embryo tissue of a kernel. In general, the sample must be homogenized using any suitable method prior to determining the LOX-1 activity.

In a preferred embodiment, the sample is taken from generation Mx kernels, wherein x is an integer $\geq 2$, preferably x is an integer in the range of 2 to 10, more preferably in the range of 3 to 8. In a very preferred embodiment LOX-1 activity is determined on M3 kernels or a sample derived from kernels. In that embodiment, it is preferred that mutagenised barley kernels (generation M0) are grown to obtain barley plants which are crossed to obtain kernels M1. The procedure is repeated until M3 kernels are available (see also FIG. 1A).

Determination of LOX-1 activity may be carried out using any suitable assay, preferably by one of the methods outlined herein below. In particular, it is preferred that the assay monitors the dioxygenation of linoleic acid to 9-HPODE by LOX-1. In general, assaying will therefore involve the steps of:
(i) Providing a sample prepared from a barley kernel or part thereof; and
(ii) Providing linoleic acid; and
(iii) Incubating said sample with said linoleic acid; and
(iv) Detecting dioxygenation of linoleic acid to 9-HPODE.

Detection may be performed directly or indirectly. Any suitable detection method may be used with the present invention. In one embodiment of the invention, linoleic acid hydroperoxides are detected. Linoleic acid hydroperoxides may for example be detected by coupling degradation of said linoleic acid hydroperoxides with an oxidative reaction, which develops a detectable compound. For example, this may be done as described in Example 1. In another embodiment 9-HPODE is detected directly, for example by spectrophotometric methods, such as HPLC as described in Example 9. In one embodiment of the invention, LOX-1 activity is determined simply by determining the amount of 9-HPODE in a sample from a barley kernel. This may be done by any suitable method known to the person skilled in the art, for example as outlined in Example 9.

It is important at what pH the determination of LOX-1 activity is performed. Preferably, said determination is performed at a pH which allows high activity of LOX-1, but only low activity of LOX-2. Hence, determination of LOX activity is preferably done at a pH in the range of 3 to 6.5, for example in the range of 3 to 4, such as in the range of 4 to 5, for example in the range of 5 to 6, such as in the range of 6 to 6.5. Preferably, the pH is around 3, such as around 3.5, for example around 4, such as around 4.5, for example around 5, such as around 5.5, for example around 6, such as around 6.5, for example around 7. Preferred methods for selecting barley plants according to the invention are described herein below in the Section 6.5 "Selecting barley mutants."

A preferred example of a method for determination of LOX-1 activity is given in Example 1.

The selection procedure may be adapted for microtitre plate assay procedures, or other known repetitive, high-throughput assay formats that allow the rapid screening of many samples. It is preferred that at least 5,000, such as at least 7,500, for example at least 10,000, such as at least 15,000 mutagenized barley plants are analyzed for LOX-1 activity.

Subsequent to the selection of useful barley plants with less than 5% LOX-1 activity, one or more additional screenings may optionally be performed. For example, selected mutants may be further propagated, and subsequent generations may be screened again for LOX-1 activity.

Subsequent to selection of useful barley plants, these may be subjected to breeding, such as conventional breeding. Methods of breeding are described herein below (Section 6.6 "Plant breeding" and Section 6.7 "Barley crossings").

The barley plant according to the invention may, however, also be prepared by other methods, for example by methods resulting in reduced transcription and/or translation of LOX-1. Hence, the null-LOX-1 barley plant may be prepared by transforming a barley plant with a nucleic acid sequence comprising, as operably linked components, a promoter expressable in barley plants, a DNA sequence, and a transcriptional termination region, wherein expression of said DNA sequence reduces the expression of the gene encoding LOX-1 by:

(i) antisense silencing; or
(ii) co-suppression silencing; or
(iii) RNA interference.

In one embodiment, the barley plant is prepared by a method involving transforming a barley plant with a nucleic acid sequence capable of reducing transcription or translation of a gene encoding LOX-1, for example a nucleic acid sequence comprising antisense LOX-1 sequences. Said antisense sequences may, for example, be the antisense sequence of [SEQ ID NO: 1], or a fragment thereof. The antisense sequence should be operably linked to a promoter sequence from a gene expressed in barley plants. A non-limiting example of such a method is outlined in Example 16 herein below.

The barley plant may be transformed by any useful method, for example *Agrobacterium tumefaciens*-mediated transfer or particle bombardment-mediated DNA uptake.

It is also a scope of the present invention that the null-LOX-1 barley plant is prepared by a method comprising the steps of:

(i) Mutagenizing barley plants and/or barley kernels and/or barley embryos; and
(ii) Determining the presence or absence of a mutation in the gene for LOX-1, wherein said mutation leads to a gene for LOX-1 encoding a polypeptide form of LOX-1 comprising less than 700 contiguous amino acids of the sequence set forth in SEQ ID NO: 3, preferably said polypeptide is an N-terminal fragment of LOX-1 comprising at the most the 700 N-terminal amino acids of [SEQ ID NO: 3],
(iii) Selecting plants carrying said mutation, thereby obtaining a barley plant comprising less than 5% of the LOX-1 activity of a wild-type barley plant.

More preferably, said mutation may lead to a gene for LOX-1 encoding any of the N-terminal LOX-1 fragments described herein above.

Said mutation may be detected using any suitable method, for example sequencing the LOX-1 gene or single nucleotide polymorphism (SNP) analysis. One example of how to perform a SNP analysis is described in Example 13 and Example 14 herein below.

6.3 Composition

The present invention also relates to compositions comprising the barley plants described above, or parts thereof, or compositions prepared from said barley plants, or parts thereof. Because said barley plants have less than 1% LOX-1 activity, compositions comprising, or prepared from, said barley plants, or parts thereof, will in general comprise very low levels of T2N and T2N potential. Examples of useful compositions comprising or prepared from null-LOX-1 barley are described herein below.

It is preferred that said compositions have:

(i) Less than 30%, preferably less than 20%, more preferably less than 10%, even more preferably less than 5%, such as less than 2%, for example less than 1% T2N; and/or
(ii) Less than 30%, preferably less than 20%, more preferably less than 10%, even more preferably less than 5%, such as less than 2%, for example less than 1% T2N potential;

compared to a similar composition comprising or prepared from wild-type barley plants.

The present invention relates in one aspects to barley kernels comprising less than 1% LOX-1 activity compared to wild-type kernels. Preferably, the kernels comprise no LOX-1 activity. The present invention relates as well to compositions comprising said kernels and compositions prepared from said kernels.

In one aspect, the invention relates to malt compositions prepared from null-LOX-1 kernels by malting. By the term "malting" is to be understood germination of steeped barley kernels taking place under controlled environmental conditions (for example as illustrated in FIG. 11, steps 2 and 3).

Malting is a process of controlled steeping and germination followed by drying of the barley grain. This sequence of events is important for the synthesis of numerous enzymes that cause grain modification, a process that principally depolymerizes the dead endosperm cell walls and mobilizes the grain nutrients. In the subsequent drying process, flavor and color are produced due to chemical browning reactions. Although the primary use of malt is for beverage production, it can also be utilized in other industrial processes, for example as an enzyme source in the baking industry, or as a flavoring and coloring agent in the food industry, for example as malt or as a malt flour, or indirectly as a malt syrup, etc.

In one aspect, the present invention relates to methods of producing said malt composition. The methods preferably comprise the steps of:

(i) Providing null-LOX-1 barley kernels (ii) Steeping said kernels (iii) Germinating the steeped kernels under predetermined conditions (iv) Drying said germinated kernels, thereby producing a malt composition with low or no LOX-1 activity. For example, the malt may be produced by any of the methods described in Hoseney (1994). However, any other suitable method for producing malt may also be used with the present invention, such as methods for production of speciality malts, including, but limited to, methods of roasting the malt. One non-limiting example is described in Example 6.

In another aspect, the invention relates to wort compositions prepared from malt compositions prepared from null-LOX-1 kernels. Said malt may be prepared from only null-LOX-1 kernels or mixtures comprises other kernels. The invention also relates to wort compositions prepared using null-LOX-1 barley or parts thereof, alone or mixed with other components. Said wort may be first and/or second and/or further wort. In general a wort composition will have a high content of amino nitrogen and fermentable carbohydrates, mainly maltose. In FIG. 11, steps 4 to 6 illustrate the common method for preparation of wort from malt. In general, wort is prepared by incubating malt with water, i.e. by mashing. During mashing, the malt/water composition may be supplemented with additional carbohydrate-rich compositions, for example barley, maize or rice adjuncts. Unmalted cereal adjuncts usually contain no active enzymes, and therefore rely on malt or exogenous enzymes to provide enzymes necessary for sugar conversion.

In general, the first step in the wort production process is the milling of malt in order that water may gain access to grain particles in the mashing phase, which is fundamentally an extension of the malting process with enzymatic depolymerization of substrates. During mashing, milled malt is incubated with a liquid fraction such as water. The temperature is either kept constant (isothermal mashing) or gradually increased. In either case, soluble substances produced in malting and mashing are extracted into said liquid fraction before it is separated by filtration into wort and residual solid particles denoted spent grains. This wort may also be denoted first wort. After filtration, a second wort is obtained. Further worts may be prepared by repeating the procedure. Non-limiting examples of suitable procedures for preparation of wort is described in Hoseney (supra).

The wort composition may also be prepared by incubating null-LOX-1 barley plants or parts thereof, such as unmalted null-LOX-1 plants or parts thereof with one or more suitable enzyme, such as enzyme compositions or enzyme mixture compositions, for example Ultraflo or Cereflo (Novozymes). The wort composition may also be prepared using a mixture of malt and unmalted barley plants or parts thereof, optionally adding one or more suitable enzymes during said preparation.

The present invention also relates to food compositions, feed compositions, and fragrance raw material compositions that comprises null-LOX-1 barley plants or parts thereof. Food compositions may for example be, but are not limited to malted and unmalted barley kernels, barley meals, bread, porridge, cereal mixes comprising barley, health products, such as beverages comprising barley, barley syrups, and flaked, milled or extruded barley compositions. Feed compositions for example include compositions comprising barley kernels, and/or meals. Fragrance raw material compositions are described herein below.

The invention also relates to mixtures of the compositions of the invention. For example, the invention in one aspect relates to a composition prepared by a mixture of (i) a composition comprising a barley plant or a part thereof, comprising less than 5% of the LOX-1 activity of a wild-type barley plant, and (ii) a malt composition prepared from null-LOX-1 kernels.

In a preferred aspect, the present invention relates to beverages, more preferred malt-derived beverages, even more preferred alcoholic beverages, such as beer having stable organoleptic qualities, wherein said beverage is prepared using null-LOX-1 barley or parts thereof. Hence, in one preferred embodiment of the invention the beverage is preferably prepared by fermentation of null-LOX-1 barley or parts thereof or extracts thereof, for example by fermentation of wort produced using malt produced from null-LOX-1 barley, alone or in combination with other ingredients.

However, in other embodiments of the invention, the beverage is a non-fermented beverage, for example wort. It is also comprised within the present invention that said beverage may be prepared from unmalted barley plants or parts thereof.

Preferably, however, said beverage is prepared from a malt composition prepared from null-LOX-1 barley kernels. More preferably, said beverage is beer. This may be any kind of beer known to the person skilled in the art. In one embodiment the beer is for example a lager beer. The beer is preferably brewed using a malt composition comprising germinated null-LOX-1 barley. The malt composition may, however, also comprise other components, for example other germinated or ungerminated cereals, such as wild-type barley, null-LOX-1 barley, wheat and/or rye, or non-germinated raw materials comprising sugars or compositions derived from malted or unmalted raw materials, for example syrup compositions.

"Organoleptic qualities" means qualities appealing to the olfactory and taste senses. These are analyzed, for example, by a trained taste panel. Preferably, said trained taste panel is trained specifically for recognition of aldehyde off-flavors, such as T2N. In general, the taste panel will consist of in the range of 3 to 30 members, for example in the range of 5 to 15 members. A method of determining the "organoleptic qualities" of a beverage is described in Example 6, herein below. In preferred embodiments, the stable organoleptic qualities are a result of low production of T2N or T2N potential.

Accordingly, it is an object of the present invention to provide beverages manufactured using a barley plant, (such as beer), preferably comprising less than 50%, preferably less than 40%, more preferably less than 35%, such as less than 30%, for example less than 20%, such as less than 10%, for example preferably less than 5%, such as less than 2%, for example less than 1% T2N and/or T2N potential compared to a beverage prepared from wild-type barley after storage for at least 1 week, preferably at least 2 weeks, more preferably at least 3 weeks, even more preferably for at least 4 weeks, such as in the range of 1 to 3 months, for example in the range of 3 to 6 months, such as in the range of 6 to 12 months, for example for more than one year. Storage is performed at a temperature in the range of 15° C. to 40° C., preferably in the range of 30° C. to 37° C., more preferably at 37° C. The beverages of the invention preferably comprise at the most 0.07, preferably at the most 0.06, more preferably at the most 0.05, even more preferably at the most 0.04, such as at the most 0.03 ppb (parts per billion) free T2N after storage for at least 1 week, preferably at least 2 weeks, more preferably at least 3 weeks, even more preferably for at least 4 weeks, such as in the range of 1 to 3 months, for example in the range of 3 to 6 months, such as in the range of 6 to 12 months, for example for more than one year after storage at a temperature in the range of 15° C. to 40° C., preferably in the range of 30° C. to 37° C., more preferably at 37° C. Preferably, the beverage also comprises in the range of 1 to 10 ppm (parts per million) sulfite, more preferably in the range of 2 to 8 ppm, more preferably in the range of 3 to 7 ppm, yet more preferably in the range of 4 to 6 ppm sulfite. In one preferred embodiment, the beverages according to the invention comprise at the most 0.04, more preferably at the most 0.03, for example at the most 0.025 ppb free T2N after storage for 2 weeks at 37° C. In another preferred embodiment of the invention the beverages according to the invention comprise at the most 0.07, preferably at the most 0.06, more preferably at the most 0.05, even more preferably at the most 0.04, such as at the most 0.03 ppb (parts per billion) free T2N after storage for 4 weeks at 37° C. in the presence of in the range of 4 to 6 ppm sulfite.

It is important for the quality of a beverage, such as beer, that the ratio of the various trihydroxyoctadecenoic acids (THAs) is kept within a specific range. Surprisingly, in addition to low levels of T2N, the product of the LOX-1 pathway (see FIG. 1B), beverages prepared from null-LOX-1 barley according to the invention also have a very low ratio of 9,12,13-THA to 9,10,13-THA. Hence, in one aspect the present invention relates to beverages, such as beer, having stable organoleptic qualities, wherein said beverage is manufactured using a barley plant or parts thereof, preferably null-LOX-1 barley and wherein the ratio of 9,12,13-THA to 9,10,13-THA within said beverage is at the most 1.8, preferably at the most 1.7, more preferably at the most 1.6, yet more preferably at the most 1.5, even more preferably at the most 1.4. It is thus very much preferred that said ratio is in the range of 0 to 1.8, preferably in the range of 0 to 1.6, such as in the range of 0 to 1.4. In one embodiment, said ratio is approximately 1.3.

Preferably said THAs are oxylipins of linoleic acid conversion. Interestingly, beverages with such THA ratios may be prepared using the barley plant according the invention. In one preferred embodiment of the invention, the beverage comprises:
  (i) a ratio of 9,12,13-THA to 9,10,13-THA as described above; and
  (ii) a level of free T2N after storage as described above.

The invention also relates to methods of producing said beverage. The methods preferably comprise the steps of:
  (i) Providing a malt composition comprising germinated null-LOX-1 kernels;
  (ii) Processing said malt composition into a beverage;

thereby obtaining a beverage with stable organoleptic qualities.

In one preferred embodiment the beverage is beer. In this case, the processing step preferably comprises preparing wort from said malt composition, for example by any of the methods described herein above and fermenting said wort.

In general terms, alcoholic beverages such as beer may be manufactured from malted and/or unmalted barley grains. Malt, in addition to hops and yeast, contributes to flavor and color of the beer. Furthermore, malt functions as a source of fermentable sugar and enzymes. A schematic representation of a general process of beer production is shown in FIG. 11, while detailed descriptions of examples of suitable methods for malting and brewing can be found, for example, in a recent publication by Hoseney (supra). Numerous, regulary updated methods for analyses of barley, malt and beer products are available [for example, but not limited to American Association of Cereal Chemist (1995); American Society of Brewing Chemists (1992); European Brewery Convention (1998); Institute of Brewing (1997)]. It is recognized that many specific procedures are employed for a given brewery, with the most significant variations relating to local consumer preferences. Any such method of producing beer may be used with the present invention. One non-limiting example is described in Example 6.

The malt composition for said beverage, i.e. beer, may for example be obtained by any of the methods described herein above. Wort may be prepared from said malt composition as described herein above.

The first step of producing beer from wort preferably involves boiling said wort. During boiling other ingredients may be added, for example hops that provide the typical bitter and aromatic beer characteristics. Boiling of wort also causes aggregation between polyphenols and denatured proteins, which mainly precipitate during the subsequent phase of wort cooling. After being cooled, the wort is transferred to fermentation tanks containing yeast. Preferably said yeast is brewer's yeast, *Saccharomyces carlsbergensis*. The wort will be fermented for any suitable time period, in general for in the range of 1 to 100 days. During the several-day-long fermentation, sugar is converted to alcohol and $CO_2$ concomitantly with the development of some flavor substances.

Subsequently, the beer may be further processed. In general it will be chilled. It may also be filtered and/or lagered—a process that develops a pleasant aroma and a flavor less yeasty. Finally the beer may be pasteurized or filtered, before it is bottled or canned.

Despite the advances which have been made in the area of beer production, it would be beneficial to reduce the levels of T2N, its precursors, and the T2N potential in beer. Accordingly, there is still a need for new raw materials, particulary barley and malt, that contribute with less off-flavors to the finished beer. It is therefore an object of the present invention to provide such barley and malt.

6.4 Chemical Mutagenesis

In one aspect, the present invention is based, at least in part, on the use of chemical mutagenesis of barley kernels, a method that is known to introduce mutations at random. Mutagenesis of barley may be performed using any mutagenizing chemical, however preferably it is performed by treating kernels with $NaN_3$, letting the surviving kernels germinate, and then analyzing off-spring plants. The plant generation growing from the mutagenized kernels, referred to as M0, contains heterozygote chimeras for any given mutation. Progeny collected after self-pollination are referred to as the M1 generation, and segregates both heterozygotes and homozygotes for a given mutation (cf. FIG. 1A and FIG. 9).

Treating kernels with $NaN_3$ is not equivalent to treating a single cell, because the kernels after the treatment will contain some nonmutant cells and a variety of cells having DNA mutations. Since mutations in cell lineages that do not lead to the germ line will be lost, the goal is to target the mutagen to the few cells that develop into reproductive tissues which contribute to development of the M1 generation.

To assess the overall mutation efficiency, albino chimeras and albino plants were counted in the M0 and M1 generation, respectively. Scoring mutant number as a function of surviving plants gives an estimate for the mutation efficiency, while scoring mutant number as a function of treated seeds measures the combination of both mutation efficiency and kernel kill.

It should be noted that cells have quality assurance mechanisms at virtually every step of gene expression, possibly to moderate the effects of damaging mutations. One well-studied example in eukaryotes is nonsense-mediated mRNA decay, denoted NMD, which prevents the synthesis of potentially deleterious, prematurely truncated proteins (Maquat and Carmichael, 2001). In NMD, a termination codon is identified as premature by its position relative to downstream destablizing elements. In *Saccharomyces cerevisiae*, these are loosely defined mRNA sequences, and in mammalian cells, they are protein complexes that are deposited at exon-exon junctions during pre-mRNA splicing. How the degradation of nonsense-mRNAs and the proteins they produce are coordinated is an area for future study.

Mutations that generate premature termination (nonsense) codons (PTCs) sometimes increase the levels of alternatively spliced transcripts that skip the offending mutations, thereby potentially saving protein function (Mendell and Dietz, 2001). Because translation and RNA splicing are thought to occur in different cellular compartments, it was paradoxical to find a nonsense codon-specific mRNA up-regulatory mechanism that acts independenly of splicing enhancer disruption in mammalian cells (Wang et al., 2002). However, such mechanisms have neither been observed in barley plants of the instant invention nor in other plants.

NMD, PCT and the like are of particular interest in the context of plant breeding because such phenomena enhance the number of kernels or grains to be screened in order to identify a new trait of interest.

6.5 Selection of Barley Mutants

One aspect of the present invention is to provide screening conditions for LOX-1 activity, wherein the activity from LOX-2 is diminished. The methods are based on the surprising discovery that the nature of barley tissue to be screened and the reaction conditions can enhance LOX activity derived from enzyme LOX-1 and diminish that from enzyme LOX-2. While the screening for low-LOX mutants as detailed in PCT application PCT/IB01/00207 published as WO 02/053721 A1 to Douma et al. utilized a proteinaceous extract of barley leaf tips, with determination of enzymic activity at pH 7.5, the present publication details advantageous screening parameters allowing reproducibly to identify null-LOX barley mutants. First, when screening for LOX-1 activity it is important that specific tissues of the barley plants are used. Preferably, said tissue comprises the barley kernel, more preferably embryos of barley kernels. In general, the screening will be performed on an extract of said tissue, i.e an extract of barley kernels or barley embryos. More preferably, extracts for LOX-1 activity determination comprise or most preferably consist of homogenized embryo tissue of dry barley kernels. In this way, only marginal activity derived from LOX-2 will contribute to the activity determinations. Second, assays for LOX-1 activity are performed at a pH which preferably inactivates allene oxide synthase enzymes, thus affording HPODEs in good yield.

6.6 Plant Breeding

In one embodiment of the invention, the objective is to provide agronomically useful barley plants comprising the null-LOX-1 trait. Crop development can be seen as an extended process that only begins with the introduction of the new trait. From the perspective of a plant breeder, this step almost always results in a plant that has a less desirable overall profile of agronomic traits than do current commercial varieties.

In addition to the null-LOX-1 trait, there are other important factors to be considered in the art of generating a commercial malting barley variety, for example kernel yield, kernel size and other parameters that relate to malting performance. Since many—if not all—of such traits have been shown to be under genetic control, it would be highly desirable to provide modern, homozygous, high-yielding malting cultivars which result from crosses with null-LOX-1 barley plants that are disclosed in the present publication. Kernels of such barley plants provide a new, superior raw material having no or only marginal capacity for the conversion of linoleic acid into 9-HPODE. The barley breeder must therefore select and develop barley plants having traits which result in superior cultivars with LOX-1 loss-of-function. Alternatively, the barley breeders may utilize plants of the present invention for further mutagenesis to generate new cultivars derived from null-LOX-1 barley.

The barley plants according to the present invention may be breed according to any suitable scheme.

6.7 Barley Crossings

Another object of the present invention is to provide agronomically elite barley plants comprising the null-LOX-1 trait. Accordingly, this invention also is directed to methods for producing a new null-LOX-1 barley plant by crossing a first parent barley plant with a second parent barley plant, wherein the first or second plant is a null-LOX-1 barley. Additionally, both first and second parent barley plants can come from a null-LOX-1 barley variety. Thus, any such methods using the null-LOX-1 barley variety are part of this invention: selfing, backcrosses, crosses to populations, and the like. All plants produced using a null-LOX-1 barley variety as a parent are within the scope of this invention, including those developed from varieties derived from a null-LOX-1 barley variety. The null-LOX-1 barley can also be used for genetic transformation in such cases where exogenous DNA is introduced and expressed in the null-LOX-1 plant or plant tissue.

Backcrossing methods can be used with the present invention to introduce a null-LOX characteristic of a mutated barley plant into another variety, for example cv. Scarleft or cv. Jersey, both of which are contemporary, high-yielding malting barley cultivars. In a standard backcross protocol, the original variety of interest (recurrent parent) is crossed to a second variety (non-recurrent parent) that carries the single gene of interest to be transferred. The resulting null-LOX-1 progeny from this cross are then crossed again to the recurrent parent, with the process being repeated until a barley plant is obtained wherein essentially all of the characteristics specified by the recurrent parent are recovered in the converted plant, in addition to the transferred genetic set-up for the null-LOX-1 trait of the nonrecurrent parent. The last backcross generation is then selfed to give pure breeding progeny for the null-LOX-1 trait (cf. FIG. 9).

Having a suitable recurrent parent is important for a successful backcrossing procedure, the goal of which is to introduce the null-LOX-1 trait into the original variety. To accomplish this, the genetic set-up of the recurrent variety is modified with that for the low-LOX-1 trait from the nonrecurrent parent, while retaining essentially all of the rest of that from the original variety. Although backcrossing methods are simplified when the characteristic being transferred is a dominant allele, it was possible to backcross that of the recessive null-LOX-1 trait—but in this case it was necessary to introduce a biochemical analysis to assess whether the desired characteristic was transferred.

A way to accelerate the process of plant breeding comprises initial multiplication of generated mutants by application of tissue culture and regeneration techniques. Thus, another aspect of the present invention is to provide cells, which upon growth and differentiation produce barley plants having the null-LOX-1 trait. For example, breeding may involve traditional crossings, preparing fertile anther-derived plants or using microspore culture.

6.8 LOX Enzymes

An important object of the present invention is to provide barley plants that lack the capacity to synthesize active LOX-1 enzyme. LOXs are large monomeric proteins with a single non-heme iron factor. Inspection of the Protein Data Bank at http://www.rcsb.org/pdb revealed that the structure of several LOX enzymes have been solved by X-ray crystallography. The proteins share an overall fold and domain organization, with each having a smaller N-terminal eight-stranded β-barrel domain and a larger C-terminal domain composed mostly of long α-helices. The iron atom is located at the C-terminal domain where it is coordinated to histidine residues and, uniquely, to the carboxyl terminus of the polypeptide, which happens to be an isoleucine. Several channels lead from the surface of the protein to the vicinity of the iron site, and these presumably afford access for the substrates, polyunsaturated fatty acids, and molecular oxygen, to the active site. Since liposome and lipid body binding of the cucumber lipid body LOX depends on the presence of the N-terminal β-barrel (May et al., 2000), and soybean LOX-1 binds to bilayer membranes in a process that is enhanced by calcium ions (Tatulian and Steczko, 1998), it can be speculated that LOX enzymes bind to lipid bilayer membranes and that this is most likely a function of the N-terminal domain. Methods for determination of LOX activity, as well as for isolation, characterization, and quantitation of direct and downstream products of LOX catalysis are readily available to those ordinarily skilled in the art.

6.9 LOX Pathway Products

In various embodiments, the present invention relates to barley plants, or products thereof, blocked in the capacity to form the alkenal T2N. LOX enzymes catalyze dioxygenation of polyunsaturated fatty acids with a cis-1,cis-4 pentadiene system. In plants, the $C_{18}$ polyunsaturated fatty acids linoleic acid ($18:2^{\Delta 9, 12}$) and α-linolenic acid ($18:3^{\Delta 9, 12, 15}$) are major LOX substrates. The lipoxygenase pathway of fatty acid metabolism is initiated by the addition of molecular oxygen at the C-9 or C-13 position of the acyl chain yielding the corresponding 9- and 13-linoleic or linolenic acid hydroperoxides. With linoleic acid as substrate, either 9- or 13-hydroperoxy octadecadienoic acids (HPODS) may be formed, while 9- or 13-hydroperoxy octadecatrienoic acids (HPOTS) are products when the substrate is α-linolenic acid. In the hydroperoxide lyase branch of the LOX pathway, both 9- and 13-hydroperoxides can be subsequently cleaved to short-chain oxoacids and aldehydes (cf. FIG. 1B).

It is recognized that the present invention encompasses influencing production of downstream metabolites of LOX-1 catalysis, which are produced not as a direct product of a LOX-1-catalyzed reaction, but as a result of a subsequent reaction of a series of reactions, involving a product of LOX-1 catalysis. These reactions include spontaneous, factor-induced or enzyme-catalyzed isomerization. Thus, the production of these downstream metabolites could be influenced by modulating the expression of hydroperoxide lyase (HPL).

On the assumption that autooxidation of linoleic acid may generate precursor molecules related to formation of T2N, it may be possible to further reduce the level of the alkenal. Specifically, down-regulation of the genes encoding Δ9-desaturase (converts stearic acid into oleic acid) or Δ12-desaturase (converts oleic acid into linoleic acid) is expected to alter the relative proportions of the $C_{18}$ fatty acids (stearic, oleic and linoleic acid) by decreasing the levels of the fatty acids downstream of the relevant enzyme and increasing the levels of the intermediate fatty acid substrate. Examples where selective breeding utilizing natural variants or induced mutations were used to develop a range of improved oils in oilseed crops include—but are not limited to—high-stearic (HS) soybean (Graef et al., 1985), high-oleic (HO) rapeseed (Auld et al., 1992), as well as HS and HO sunflower by Osorio et al. (1995) and Soldatov (1976), respectively.

Especially of interest is that the invention encompasses production of aldehydes which are not direct products of LOX-1 action, but are produced by the action of enzymes of the LOX pathway, or by the isomerization of aldehydes, for example, isomerization of (3Z)-nonenal to (2E)-nonenal as provided in FIG. 1B. It is also recognized that the invention encompasses production of such alcohols which correspond to the aldehydes produced by enzymes of the LOX pathway, and/or which correspond to aldehydes produced as a result of said isomerization. Said alcohols are typically produced by the action of enzyme members of the aldo-keto reductase superfamily (Srivastava et al., 1999), for example through enzymatic conversion of (2E)-nonenal to (2E)-nonenol.

6.10 T2N Potential

A further object of the present invention is to reduce or eliminate molecules related to the formation of T2N, including the formation of T2N precursors and aldehyde adducts. Although several chemical reactions related to beer staling remain elusive, oxidation processes are recognized as the major causes of the development of stale flavor in beer products (Narziss, 1986; Ohtsu et al., 1986). As described in detail in Section 2 ("Background of the invention"), it is well known that the major molecular contributor to the stale flavor is T2N. When this aldehyde is generated in the process of making beer at a production stage before fermentation, it can participate in the formation of adducts through binding to for example amino acids and proteins (Noel and Collin, 1995)—but possibly also nucleic acids, glutathione or the like—and subsequently be protected from reduction or oxidation by fermenting yeast (Lermusieau et al., 1999). However, T2N adducts can also be formed with sulfite during fermentation, rendering the aldehyde flavor-inactive (Nyborg et al., supra).

Most of the T2N adducts are transferred to the finished beer, in which free T2N is liberated (Liegéois et al., 2002), the conditions of acidity and temperature being important factors in this process. T2N adducts comprise part of the T2N potential, a measure for the degradation of T2N adducts to free T2N under defined reaction conditions, e.g. incubation at 100° C., pH 4.0, for 2 h. The skilled artisan knows how to relate the T2N potential as an indicator of how beer will release T2N during storage, for example as described by Drost et al. (supra).

Barley kernels of the instant invention are restricted in the LOX-1-catalyzed formation of 9-HPODE, a molecule that normally functions as a precursor in the LOX pathway branch that yields T2N. Beers produced using null-LOX barley kernels will therefore not only possess a very low level of T2N, but also a very low level of T2N potential. Within the scope of the present invention are null-LOX-1 barley kernels yielding beer products that totally lack T2N, or contain insignificant levels of T2N potential, including T2N adducts. Consequently, there is no, or only insignificant, development of T2N-specific off-flavors during storage of beer produced using null-LOX-1 barley.

6.11 Disease Resistance

The present invention further relates to disease resistant barley. Plant LOXs are considered to be involved in the development of active disease resistance mechanisms, collectivley known as the hypersensitive response (HR), a form of programmed cell death (Rusterucci et al., 1999). In the HR, an infection event is followed by rapid cell death of plant cells localized around the infection site, and this leads to the formation of a necrotic lesion. In this way, pathogen spread is limited and prevents further damage to the remainder of the plant organ. In several plant-pathogen systems, HR is linked to expression of LOXs having specificity for the generation of 9-HPODE and 9-HPOTE (Rusterucci et al., supra; Jalloul et al., 2002), possibly because the massive production of hydroperoxy fatty acids confers tissue necrosis.

The gene encoding LOX-1 is primarily expressed in barley kernels, while numerous additional LOX enzymes are expressed in the leaves of the plants. Accordingly, the LOX pathway branches leading to the formation of 9-HPODE, 13-HPODE, 9-HPOTE, and 13-HPODE are functional in barley leaves, and different sets of oxylipins reflect separate infection and wounding events. A similar molecular scenario has been described for potato leaves (Weber et al., 1999).

Naturally occurring volatile aldehydes inhibit growth of certain pathogens on plants, and natural resistance of some plants to a particular pathogen can be attributed to generation of volatile aldehydes (Croft et al., 1993; Blée and Joyard, 1996; Vancanneyt et al., 2001). Thus, relative to wild-type plants, the altered oxylipin profile of null-LOX-1 barley plants of the invention may prevent, reduce, ameliorate or eliminate the presence of a pathogen, a product of a pathogen, or a product of a plant-pathogen interaction. One non-limiting example of a pathogen is *Aspergillus* (see herein below).

Hence, in one embodiment the invention relates to a null-LOX-1 barley plant exhibiting enhanced disease resistance.

6.12 Mycotoxins

The present invention also discloses the use of barley plants with reduced susceptibility to *Aspergillus* colonization. *Aspergillus* is a troublesome colonizer of barley kernels, often causing contamination with the carcinogenic mycotoxins aflatoxin and sterigmatocystin. Since the production of aflatoxin by the fungus is influenced by high levels of 9-HPODE, 9-HPOTE, 13-HPODE, and 13-HPOTE, U.S. Pat. No. 5,942,661 to Keller claims transgenic crop plants that produce said hydroperoxy fatty acids in amounts sufficient to inhibit the production of fungal mycotoxins. In addition, said U.S. patent as well as data by Burow et al. (2000) specify that 13-HPODE inhibits aflatoxin production, while 9-HPODE boost aflatoxin production.

Since null-LOX-1 kernels lack active LOX-1 enzyme, said kernels contain slightly higher levels of 13-HPODE than wild-type plants, but also lower levels of 9-HPODE relative to the tissue of its non-genetically modified parent plant. Relative to wild-type kernels, null-LOX-1 kernels can therefore ward off colonizing *Aspergillus,* or exhibit reduced mycotoxin levels following contamination with *Aspergillus.*

Hence, the present invention relates to barley plants with reduced levels of mycotoxins compared to wild-type barley plants.

6.13 Fragrances

It is also an aspect of the present invention to use null-LOX-1 barley for production of fragrances and green note compounds. To date, most research efforts related to the various branches of the LOX pathway in barley have focused on aspects of jasmonic acid generation from 13-HPOTE (Turner et al., 2002), and on disease resistance as described above. Less attention has been paid to barley hydroperoxy fatty acids for alternative, commercial purposes. However, it is notable that the total absence of active LOX-1 in null-LOX-1 barley kernels is anticipated to enrich 13-HPODE and 13-HPOTE in said kernels. Based on this novel property, new applications are likely with respect to industrial usage of the barley crop, for example in the production of short-chain aliphatic aldehydes and alcohols (e.g. the green note compounds hexanal/hexenal and hexanol/hexenol).

Several aspects related to the production of green notes are disclosed in patents, including—but not limited to—U.S. Pat. Nos. 6,008,034, 6,150,145 and 6,274,358 which are discussed. While U.S. Pat. No. 6,008,034 to Hatusler et al. discloses the use of a specific hydroperoxide lyase for the production green note compounds, U.S. Pat. No. 6,150,145 to Häuser et al. and U.S. Pat. No. 6,274,358 to Holtz et al. describe the use of standard plant material for such a process. Using null-LOX-1 kernels for the production of green note compounds comprises the use of a novel raw material for said production. The novel raw material derived from null-LOX-1 barley kernels of the present invention cannot be considered a standard plant material, since it is derived from kernels that have been selected following a mutagenesis protocol as detailed in Sections 6.4-6.7 of the instant publication. Industrial usage of null-LOX-1 barley kernels is considered outside the scope of the claims recited in the patents described in the previous paragraph, primarily because the novel raw material produced from null-LOX-1 kernels of the instant invention will greatly improve the normal limitations imposed by LOX-1-catalyzed generation of 9-HPODE and 9-HPOTE—two hydroperoxy fatty acids that cannot function as precursor molecules for the enzymatic generation of the green notes cis-3-hexenal and cis-3-hexenol.

6.14 Heterologous Expression of Genes Encoding LOX

In various embodiments, the present invention relates to transgenic barley plants having the null-LOX-1 trait. It is envisioned that future advances in the genetic engineering of plants will lead to generation of barley plants with suppressed synthesis of LOX-1. The concept has been proposed as a means to control off-flavor formation, but results of such an approach are not reported (McElroy and Jacobsen, 1995). The invention described herein may be used in conjunction with such future improvements to generate antisense LOX-1 plants having antisense constructions complementary to at least a portion of the messenger RNA (mRNA) for the LOX-1 sequences can be constructed. Antisense nucleotides are constructed to hybridize with the corresponding mRNA, for example, similar to that described for expression of antisense SnRK1 protein kinase sequence in transgenic barley (Zhang et al., 2001). Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the applicability of this invention is not limited only to those plants generated by conventional mutagenesis methods.

Although targeted gene replacement via homologous recombination is extremely facile in yeast, its efficiency in most multicellular eukaryotes is still limited, and does not yet allow for the generation of such barley plants, as well as the generation of a set of genome-wide gene disruptions (Parinov and Sundaresan, 2000). Gene silencing has recently been used to study the role of ~86% of the predicted genes of the Caenorhabditis elegans genome in several developmental processes (Ashrafi et al., 2003; Kamath et al., 2003). For the generation of barley plants with complete loss-of-function of a specific gene, such as the LOX-1-encoding gene, use of the RNA interference (RNAi) method has several drawbacks. These include the lack of stable heritability of a phenotype, variable levels of residual gene activity (Hannon, 2002; Bargman, 2001; Wesley et al., 2001), and the inability to simultaneously silence several unrelated genes (Kamath et al., 2000).

The nucleotide sequences of the present invention may also be used in the sense orientation to suppress the expression of endogenous genes encoding LOX enzymes in plants. Methods for suppressing gene expression in plants using nucleotide sequences in the sense orientation are known in the art (see, for example, U.S. Pat. No. 5,283,184 to Jorgensen and Napoli). The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity.

It is notable that various aspects related to heterologous expression of genes encoding LOX enzymes are described and disclosed in U.S. Pat. Application Publication No. 2003/0074693 A1 to Cahoon et al. Although said patent application recites prior art with respect to barley LOX enzymes, and disclose numerous LOX-encoding gene sequences, neither of the barley genes encoding LOX-1, LOX-2 and LOX-3 exhibit sufficient degree of identity to be encompassed within the claims recited in U.S. Pat. Application Publication No. 2003/0074693 A1 to Cahoon et al.

While the invention has been detailed in the foregoing description, the same is considered as illustrative and not restrictive in character, it being understood that all changes and modifications that come wihtin the spirit of the invention are desired to be protected. Accordingly, it will be obvious that certain changes and modifications, such as single gene modifications and mutations, somaclonal variants, variant individuals selected form large populations of the plants of the instant cultivar and the like may be practiced within the scope of the invention, as limited only by the scope of the appended claims. The invention will be further described with reference to the following specific examples; these are offered to further illustrate the present invention, but are not construed as limiting the scope thereof.

7. EXAMPLES

The examples herein illustrate preferred embodiments of the invention and should not be considered as limiting for the invention.

Unless otherwise indicated, basic molecular biological techniques were performed for manipulating nucleic acids and bacteria as described in Sambrook et al. (1989) and Sambrook and Russell (2001).

Example 1

Screening and Mutant Selection

Barley mutagenesis. Kernels collected from barley plants of cv.s Barke, Celeste, Lux, Prestige, Saloon, and Neruda were incubated separately with the mutagen $NaN_3$ according to the details provided by Kleinhofs et al. (1978). This procedure was chosen since it is known to induce point mutations in the barley genomic DNA, and confers amino acid substitutions or truncations in those proteins encoded by the mutagenized DNA.

In the mutagenesis experiments of the instant publication, it was chosen to propagate mutated grains of generation M1 in field plots through two subsequent generations, eventually yielding a high proportion of homozygous plants for screening purposes (FIG. 1). Mutant grains of the resulting M3 generation were expected to occur at a frequency of 0.9-2.3 per 10,000 grains (Kleinhofs et al., supra). It is notable that M2 grains were not screened, primarily because these contain a relatively high proportion of heterozygous point mutations.

Screening. It was the aim to develop a rapid high-throughput screening procedure for detection of M3 mutant barley grains lacking LOX-1 activity, to avoid the troublesome screening procedure using leaf tips known to contain several LOX activities (disclosed in PCT application PCT/IB01/00207 published as WO 02/053721A1 to Douma et al.). Focus was on the determination of LOX activity in the embryo, including scutellum tissue, of mature barley kernels. In general, the assay conditions were similar to those described by Anthon and Barrett (2001). The assay was based on the LOX-catalyzed generation of linoleic acid hydroperoxides, which—in a haemogolobin-catalyzed reaction—oxidatively couple 3-methyl-2-benzothiazolinone with 3-(dimethylamino)benzoic acid, resulting in the formation of a blue color that can be measured spectrophotometrically.

In practical terms, one assay series was initiated by the separate homogenization of 96 barley embryo tissues, including the scutellum, into compositions of fine powder. These were transferred to ice-cold storage plates (ABgene), in which each of the 96 wells of 1.2 ml contained a circular 5-mm glass bead and 200 μl of $H_2O$. The plate was then incubated for 35 sec in an MM 300 laboratory mill (Retsch), electronically adjusted to shake at a frequency of 27 $sec^{-1}$. Subsequently, the plate was centrifuged at 4,000 rpm in an Allegra 6R Centrifuge (Beckman-Coulter) for 15 min at 4° C. to precipitate insoluble material, and thereafter kept on ice for max. 120 min until further processing.

The 96-well plate was transferred to a Biomek 2000 Laboratory Automation Workstation (Beckman-Coulter), which was programmed for pipetting according to the LOX assay as described by Anthon and Barrett (supra). Eventually, 96×26 μl embryo extracts were transferred to a standard 96-well microtitre plate (Nunc), followed by addition of 90 μl of Reagent A [12.5 mM 3-(dimethylamino)benzoic acid, 0.625 mM linoleic acid (prepared as detailed in Example 9)] and 90 μl of Reagent B (0.25 mM 3-methyl-2-benzothiazolinehydrazone, 0.125 mg/ml haemoglobin); Reagent A was made by first mixing 155 μl of linoleic acid, corresponding to 134 mg free acid (Sigma, L-1376) and 257 μl Tween-20, then $H_2O$ was added to give a volume of 5 ml, followed by addition of 600 μl of 1 M NaOH, and when the solution turned clear it was adjusted to 20 ml with additional $H_2O$. $A_{595}$ was measured in each of the 96 wells of the plate using a Flourostar Galaxy spectrophotometer (BMG Labtechnologies), with the color formation of hydroperoxide products being a measure of the total LOX activity present [activities are accordingly given in $A_{595}$ units ($A_{595}$ U)].

Identification of potential mutants. Grains of barley cv. Barke (derived from a total of 2,160 lines), cv. Celeste (2,867 lines), cv. Lux (2,625 lines), cv. Prestige (1,379 lines), cv. Saloon (1,743 lines), and cv. Neruda (3,780 lines) were screened for LOX activities, with the aim to identify grains highly reduced in said activity when compared with wild-type grains. A total of 90 potential raw mutants were identified in the M3 generation [cv. Barke (12 lines), cv. Celeste (38 lines), cv. Lux (9 lines), cv. Prestige (16 lines), cv. Saloon (12 lines), and cv. Neruda (3 lines)]. Grains from each of these mutants were propagated to the M4 generation, harvested, and then re-screened for the trait related to very low LOX activity. Eventually, only one line of cv. Barke, denoted mutant D112, and for one line of cv. Neruda, denoted mutant A618, were shown to exhibit said very low, total LOX activity.

Detailed measurements of LOX activities were performed with extracts of mature, quiescent grains, in which the LOX activity was conferred almost exclusively by LOX-1 (Schmitt and van Mechelen, 1997). For embryos of dry, mature M3 grains of mutant D112, the total LOX activity—as determined by the colorimetric LOX assay as described above (cf. FIG. 2; Table 1)—was 0.407±5.8% $A_{595}$ U/embryo, while that for cv. Barke was 1.245±7.6% $A_{595}$ U/embryo. In a second set of experiments, the LOX activity in embryo extracts of mature, dry grains of generation M3 of mutant A618 was found to be 0.221×2.6% $A_{595}$ U/embryo, while 0.721±3.6% $A_{595}$ U/embryo was found in extracts of wild-type cv. Neruda (FIG. 3; Table 1).

Example 2

Barley Mutants D112 and A618

Analyses were conducted to establish whether null-LOX-1 plants of the M4 and M5 generations were homozygous for the corresponding mutant phenotype. This type of analysis was useful for the determination of the recessive or dominant nature of the mutation of interest in the M3 generation. In other words, if plants of generation M3 generation were heterozygous for a dominant mutation, then subsequent generations would segregate for that phenotype.

Total LOX activity was measured in embryos of generations M3, M4 and M5 of barley mutants D112 and A618, and the activities were compared with those of embryos from cv. Barke and cv. Neruda, respectively. Determination of LOX activity was as descibed in Example 1 of the instant publication. In all of the experiments, standard extracts from embryos of cv. Barke, as well as heat-inactivated, standard extracts from embryos of cv. Barke, were used as control samples.

For embryos of generation M4 grains of mutant D112, the average total LOX activity was 0.334±1.5% $A_{595}$ U (n=12), and that for embryos of generation M5 of mutant D112 was 0.294±4.1% $A_{595}$ U (n=90). For comparison, wild-type cv. Barke embryos of generation M4 and generation M5 yielded 0.738±3.2% $A_{595}$ U (n=2) and 0.963±7.5% $A_{595}$ U (n=90), respectively (cf. FIG. 4; FIG. 5; Table 1, Experiment 1).

Embryos of generation M4 of barley mutant A618 yielded an average LOX activity of 0.222±2.1% $A_{595}$ U (n=4). Other results of this experiment revealed that the LOX activity in embryos of cv. Neruda was 0.684±5.8 % $A_{595}$ U (n=90). The results are summarized in FIG. 6 and Table 1, Experiment 2.

In summary, experimental data confirmed that grains of the generations M4 and M5 of mutant D112 were homozygous for the genetic trait specific for a very low, total LOX activity. The same property was shown for grains of the M4 generation of mutant A618.

Example 3

Physiological Properties of Barley Mutants D112 and A618

Plant propagation in the greenhouse. Grains of cv. Barke and mutant of D112 (generations M4 and M5) were germinated and grown in a greenhouse under 20 h light at 12° C. at a relative humidity of 65%. The growth characteristics of mutant D112 and wild-type cv. Barke plants were similar with respect to plant height, number of tillers per plant, the onset of flowering and the number of grains per spike. Therefore, it can not only be concluded that mutant D112 has a wild-type plant growth physiology, but also a normal grain development.

Mutant A618 grains of generation M4 and grains of cv. Neruda were germinated and grown in a greenhouse under light/dark conditions of 20 h/4 h at 12° C. and a relative humidity of 65%. By comparison of mutant A618 and cv. Neruda, no differences were observed with respect to plant height, number of tillers per plant, the onset of flowering and number of grains per spike. However, the dorsal side grains of mutant A618 differed from the mother cv. Neruda by an abnormal hole-like structure. In summary, it can be concluded that mutant A618 exhibits a wild-type-like plant growth physiology, but an abnormal grain development.

Agronomic performance of mutant D112 under field conditions. Mutant D112 and cv. Barke plants were compared in field trials to identify possible differences with respect to plant height, heading date, disease resistance, lodging, ear-breakage, maturation time and yield (see Table 2).

The trials were performed according to standard procedures for field trials. Accordingly, equal amounts of kernels of mutant D112 and cv. Barke were sown in 7.88-m$^2$ plots on 2 locations, each comprising 3 replications. Agronomic data characteristics, with emphasis on the properties described above, were carefully observed throughout the entire growth season. No differences with respect to agronomic traits were observed for neihter mutant D112 nor cv. Barke.

Example 4

Mutants D112 and A618 are Null-LOX-1 Plants

Protein analyses. The following analyses were performed to characterize the mutant phenotype of mutants D112 and A618. Western blot analyses were performed of extracts of embryos removed from quiescent barley grains. One embryo was extracted in 300 µl ice cold water in a motar, the extracts were transferred to a microcentrifuge tube and centrifuged 10,000×g. Sample aliquots comprising 10 µl of crude extracts were separated by sodium dodecyl sulphate-polyacrylamide gel electrophoresis (SDS-PAGE) according to descriptions provided by Laemmli (1970). Separated proteins were thereafter transferred to nitrocellulose membranes by semi-dry blotting as detailed by Towbin et al. (1979). The blot was probed with a 1:500 dilution of the LOX-1 -specific monoclonal antibody 5D2 (Holtman et al., 1996), followed by incubation with goat anti-mouse antibody coupled to alkaline phosphatase, and detected with the alkaline phosphatase substrates nitro blue tetrazolium and 5-bromo-4-chloro-3-indolyl-phosphate as described by Holtman et al. (supra). LOX-1 was recognized by the 5D2 antibodies in extracts of cv. Barke embryos, and the protein migrated in SDS-PAGE similarly to that of LOX-1 from cv. Vintage.

Immuno-detectable LOX-1 was absent in samples of mutant D112, but the protein could be identified in extracts of cv. Barke, mutant line G, and cv. Vintage. The Western analyses of cv. Barke and mutant D112 progeny lines of generation M4 revealed that the LOX-1 protein was present in grains from cv. Barke embryos, but not in any of the progeny grains of mutant D112 (FIG. 7), thus confirming that the null-LOX-1 trait is genetically stable. The data were statistically significant, as determined by a chi-square test (p<3.84).

Mutant A618 and cv. Neruda were analysed for LOX-1 protein in embryos of the M3 and M4 generations as described above. LOX-1 protein could be detected in embryo extracts of cv. Neruda of both generations. However, a very faint LOX-1 protein band was observed in raw mutant A618 and also embryos of the progeny lines (FIG. 8), possibbly because of cross reaction with other LOX enzymes.

Backcrossing. Repeated back-crossing was used to transfer the null-LOX-1 phenotype from mutant D112 into a recurrent parent (cf. FIG. 9), in the present publication cv. Prestige. The backcrossing program was planned as illustrated in FIG. 9, combined with selection for the trait of interest. The aim was to substitute progressively the genome of mutant D112 with that of the recurrent parent. In this way, other potential, disadvantageous mutations introduced into the genome of mutant D112 during the $NaN_3$ mutagenesis treatment may be eliminated.

In the first backcross of the homozygous null-LOX-1 mutant D112 (denoted genotype nn) to cv. Prestige (denoted genotype NN), the progeny lines were expected to comprise a heterozygous genotype (denoted genotype Nn). It is notable that a low-LOX phenotype, due to its recessive nature, would escape detection in those lines that are heterozygous for the mutation. Self-pollinated progeny plants were expected to yield a population of plants that would segregate in a normal Mendelian pattern, namely in the ratio 1 NN :2 Nn: 1 nn. The homozygous nn genotype comprising the null-LOX-1 genotype and resulting from the first backcross was expected comprise 50% of the genetic background of cv. Prestige. After 10 rounds of back-crossing, the recurrent parent background was expected to amount to ~99.9%.

Barley plants of cv. Prestige and null-LOX-1 mutant D112 were propagated in a greenhouse throughout the back-crossing program. Backcrossed progeny grains were analyzed for presence of LOX-1 protein in extracts of embryos, as described in Example 1. The expected frequency of the null-LOX-1 phenotype in the segregating progeny of the first and second backcross generations was 25% for a recessive mutation (FIG. 10). Using the western blot analysis as basis for detection of barley mutant lines lacking the LOX-1 protein band, the frequency in the first backcross generation corresponded to 3 lines out of a total of 12 backcrossed lines. In the second backcross generation, 9 lines out of a total of 28 backcrossed lines lacked the LOX-1 protein band in the western blot analysis (FIG. 10). Since the recurrent parent background amounts to around 75% in the second backcross progeny, the co-inheritance of the mutated gene for LOX-1 and thecorresponding null-LOX-1 phenotype provided confirmation for their genetic linkage. A chi-square test revealed that the observed data could be catagorized as being statistically significant. The p value was low (<3.84), a property that showed significance for both the first and the second backcross generation.

The backcrossing program demonstrated that the mutant allele conferring the null-LOX-1 phenotype can be transferred to an alternative genetic background, and that it was inherited in a recessive monofactorial manner following Mendelian segregation.

Example 5

Mashing

Preparation of wort. To test the properties of new barley cultivars, malt samples of 25-225 g were produced thereof (cf. FIG. 11). Using a laboratory mashing system that comprised an external stirrer and a water bath equipped with a thermostat capable of ramping the temperature in a well-defined gradient, mashing was performed in small-scale. The final mash was filtered using a paper filter. Wort boiling was performed in laboratory-scale using a heating mantel and a round bottomed flask connected to a reflux cooler.

Example 6

Malt and Beer Production Using Malt of Wild-Type and Mutant Barley

Barley of cv. Barke and mutant D112 were propagated in the field for several seasons in order to obtain sufficient grain material for malting and brewing. Analysis of the finished beer for T2N as well as organoleptical analysis demonstrated the improved flavour stability of beer brewed with malt of mutant D112.

Malting of kernels derived from mutant D112 and cv. Barke. Malting was performed on a 20-kg-scale in a malthouse as follows: Mutant D112 barley grain (harvested in 2003), cv. Barke grains (harvested in 2002). Steeping conditions were: 8 h wet; 14 h dry; 8 h wet; 10 h dry; 4 h wet in steeping water at 16° C. Malting conditions were: 12 h at 18° C.; 24 h at 16° C.; 24 h at 14° C.; 60 h at 12° C. Drying conditions were: 12 h at 60° C.; 3 h at 68° C.; 4 h at 74° C.; 3 h at 80° C.

Data of malting analyses using malt samples derived from mutant D112 and cv. Barke malt are compared in Table 3. The results demonstrated that malt of mutant D112 and cv. Barke fulfilled the malt specifications, and confirmed that the malts were suitable for brewing. A significant reduction in T2N levels was observed in malt from mutant D112 when compared to cv. Barke malt, corresponding to a reduction of ~64% (Table 4).

Brewings with malt of mutant D112 and cv. Barke. Brewings were performed on a 50-l scale, and involved the following steps: (i) wort preparation; (ii) wort separation; (iii) wort boiling; (iv) fermentation; (v) lagering; (vi) bright beer filtration; and (v) bottling. Wort was prepared using malt of mutant D112, or malt of cv. Barke, the latter used as the reference sample. For each brew, a total of 13.5 kg malt was used. Mashing-in was at 47° C for 20 min, followed by 18 min of heating in which the temperature was raised from 48° C. to 67° C.; 30 min pause at 67° C.; then heating up to 72° C. for 5 min; 15 min pause at 72° C., heating up to 78° C. for 6 min; 5 min pause at 78° C. The brewing steps of wort filtration and boiling, whirlpool separation, fermentation, lagering and packaging in green glass bottles were according to specifications for standard brewing practice. A total of 33 l beer was bottled.

Flavor stability and T2N analyses. Beer was produced using malt of mutant D112 and cv. Barke as described above. Freshly bottled beer was stored at 5° C. and analyzed within 2 months of production. The flavor stability of the fresh and stored beers were evaluated following two different types of beer storage conditions. In one experimental series, the beer was subjected to a forced-aging process at 37° C. for a period of 1 to 4 weeks.

T2N levels of beer samples were determined by gas chromatography with mass spectrometric detection following derivatisation of carbonyls with O-(2,3,4,5,6-pentafluorobenzyl)-hydroxylamine, essentially as described by Gronqvist et al. (1993).

A trained beer taste panel evaluated the overall flavor score of the beer. The examinations included detection of a cardboard flavor, indicative of free T2N in the beer. It is notable that both types of fresh beer contained similar levels of sulfite, namely 4 ppm and 5 ppm sulfite for the beer derived from malt of mutant D112 and cv. Barke, respectively.

Forced-aging. Bottled beer produced from malt of cv. Barke and bottled beer produced of malt derived from mutant D112 were examined and compared, with resepect to specific data on the development of free T2N during forced-aging as shown in FIG. 12 and Table 5. It is seen that the beers may be distinguished by the pronounced differences in the kinetics of T2N development. While the reference beer performed as expected, an unexpected and remarkably low development of T2N was observed in the beer derived from mutant D112, corresponding to 0.01 ppb over 4 weeks at 37° C.

The forced-aging experiment emphasized the difference among the two beers. Already after 2½ weeks exceeded the T2N level of the reference beer the taste threshold level, while that produced using malt of mutant D112 leveled-off at a T2N concentration of 0.025 ppb after 2-3 weeks of incubation.

Regarding the taste and flavor stability, a panel of flavor specialists evaluated beer produced using the malt of null-LOX-1 barley mutant D112. Focus was on beer samples that had undergone forced-aging at 37° C. The taste panel found satisfactory flavor profiles for both types of the fresh and the forced-aged beers (1 week at 37° C.). However, the scores for the papery taste were higher for the reference beer than that produced using malt of null-LOX mutant D112 (Table 5), i.e. the reference beer had a more intense taste of the mentioned off-flavor. In general, the taste panel preferred the beer produced from the malt of null-LOX-1 mutant D112 (flavor acceptance score, Table 5).

In summary, the improved flavor stability of beer brewed from malt of barley mutant D112 is remarkable, primarily due to the low levels of T2N in beer following storage at 37° C. The brewing trial which focused on the use of null-LOX-1 barley malt provided evidence that barley LOX-1 action during the malting and brewing process constitutes a key determinant for the appearance of T2N, a principal off-flavor compound in aged beer.

Example 7

Trihydroxyoctadecenoic Acids in Beer of Null-LOX-1 Malt

Beer-specific trihydroxyoctadecenoic acids (THAs) derived from linoleic acid were described 30 years ago (Drost et al., 1974). Since then, various reports have verified that the total content of THAs in beer ranges from 5.7 to 11.4 µg/ml (Hamberg, 1991; and references therein). While 9,12,13-THA normally constitutes 75-85% of the THAs in beer, that of 9,10,13-THA is normally only 15-25%. Other isomers are found in trace amounts.

In beer produced from D112 (null-LOX-1 malt), the concentration of 9,12,13-THA is reduced almost 5 fold compared to the reference beer made from malt of cv. Barke (Table 6), i.e. the isomers 9,12,13-THA and 9,10,13-THA are present in almost equal quantities in beer produced using malt of null-LOX mutant D112.

Example 8

Trihydroxyoctadecenoic Acids in Beer

The concentration of THAs in a wide range of commercially available beer samples is shown in Table 7. Close inspection of the result on THAs in beer samples, as shown in Table 7, revealed that the ratio of 9,12,13-THA: 9,10,13-THA always exceeded 3.5. In constrast, in beer produced from D112 the ratio of 9,12,13-THA: 9,10,13-THA is 1.3. Hence, beer produced from null-LOX-1 barley comprises a signifi- cantly lower ratio, and determination of the 9,12,13-THA: 9,10,13-THA ratio provides a tool to determine whether a beer is produced using malt of null-LOX barley mutants, e.g. that of barley mutant D112.

Example 9

Biochemical Characterization of Enzymatic Products from LOX Action in Barley

Mature wild-type barley grains contain two major LOX activities derived from the enzymes LOX-1 and LOX-2. The enzymes catalyze the dioxygenation of linoleic acid into hydroperoxy octadecadienoic acids (HPODEs), with enzyme LOX-1 catalyzing the formation of 9-HPODE and enzyme LOX-2 catalyzing the formation of 13-HPODE. In the mature grain, LOX-derived activity is confined to the embryo. To examine how mutations in the gene for LOX-1 affect HPODE formation, embryo extracts from cv. Barke and similar extracts from barley line G (low-LOX kernels, PCT application PCT/IB01/00207 published as WO 02/053721A1 to Douma et al.), as well as embryo extracts of null-LOX mutant D112 were studied by high pressure liquid chromatography (HPLC) analysis.

Barley embryos. The preparations of crude protein extracts from embryos were made by first dissecting the organs from mature barley grains using a scalpel to cut between the scutellum and the endosperm. Each sample, consisting of 4 embryos, was then placed between two pieces of weighing paper, and hammered gently to produce a homogenous flour. This was transferred to a 1.5-ml microcentrifuge tube, 600 µl of a 200-mM lactic acid buffer, pH 4.5, was added, and the tube was placed on ice for 10 min before further homogenization using a plastic pestle (Kontes). Subsequently, 600 µl water was added to each tube and the samples were centrifuged for 2 min at 20.000×g. A 100-µl aliquot of the resulting supernatant was transferred to a 15-ml centrifuge tube [Cellstar (Cat. No. 188271) purchased from Greiner Bio-One] to prepare for analysis of the reaction products following LOX action. 2 ml of a 100-mM sodium phosphate buffer, pH 6.5, containing 260 µM linoleic acid [the substrate was prepared by mixing 10 ml of a 100-mM sodium phosphate buffer, pH 6.5, with 100 µl of a 24-mM linoleic acid stock solution. The latter was made by first mixing 155 µl of linoleic acid (corresponding to 134 mg free acid; L-1376, Sigma) and 257 µl Tween-20, then adding $H_2O$ to a volume of 5 ml, followed by addition of 600 µl 1 M NaOH, and when the solution turned clear, the final volume was adjusted to 20 ml with $H_2O$]. After a 15-min incubation on a rotary shaker, 2 ml ethyl acetate was added and the sample content mixed by vigorous shaking for 5 sec in order to extract 9-HPODE and 13-HPODE. The sample was then centrifuged for 10 min at 800×g and 1 ml ethyl acetate was transferred to a 1.5-ml microcentrifuge tube in which the ethyl acetate was evaporated under a stream of nitrogen gas. Subsequently, the HPODEs were resuspended in 300 µl of methanol, and filtered through a 0.45-µm membrane (Millex-HN filter, Millipore).

Analysis of the HPODE content was performed by HPLC. A total of 15 µl from each sample was injected into a HPLC apparatus (HP 1100 Series, Hewlett Packard), equipped with a 4.6×250 mm Symmetry C18 column (Waters). The mobile phase used was a 16:12:12:10:0.5 (v:v:v:v:v) mixture of water:methanol:acetonitrile:tetrahydrofuran:trifluoroacetic acid. The flow of the mobile phase was 1 ml per min and the pressure measured in front of the column was 140 bar. The separation was performed at 30° C. Detection of hydroperoxides with conjugated double bonds was performed at 234 nm. A standard sample comprised a mixture of 9(S)-hydroperoxy-10(E),12(Z)-octadecadienoic acid [(9(S)-HPODE] and 13(S)-hydroperoxy-9(Z),11(E)-octadecadienoic acid [(13(S)-HPODE], as detailed in FIG. 13A.

Figure 13A:
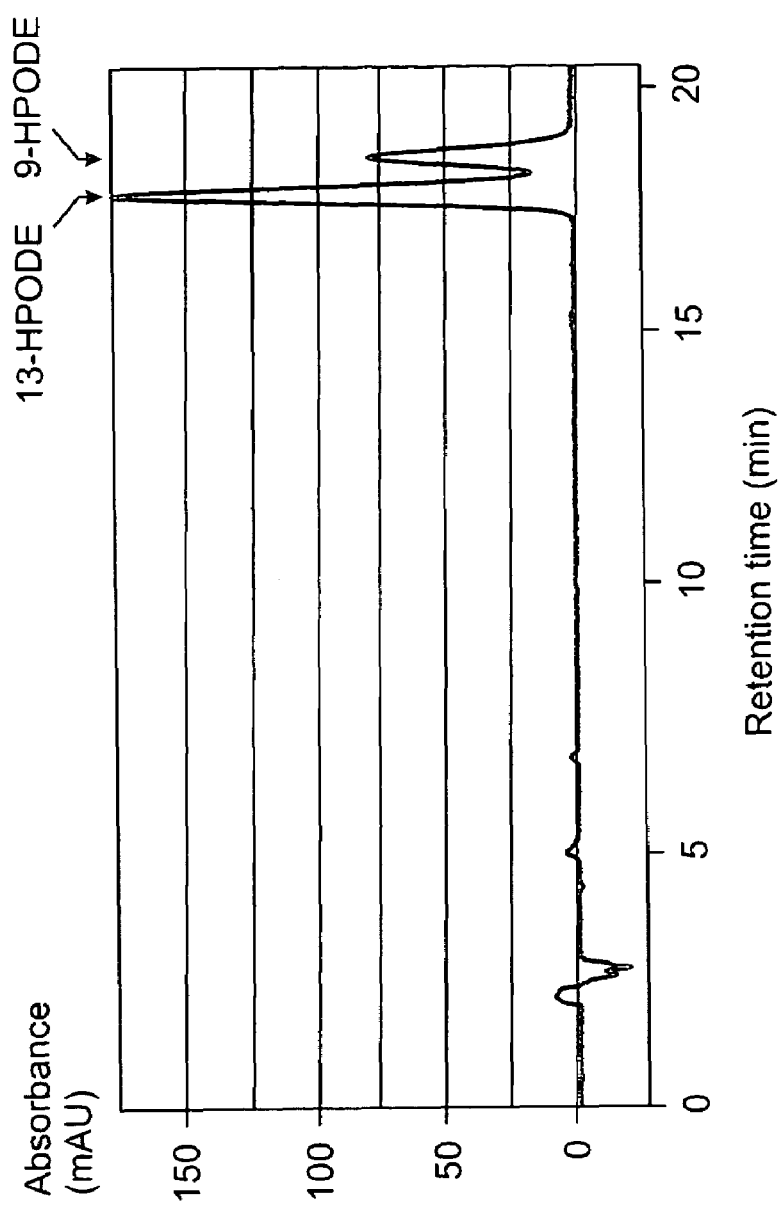
Figure 13B:
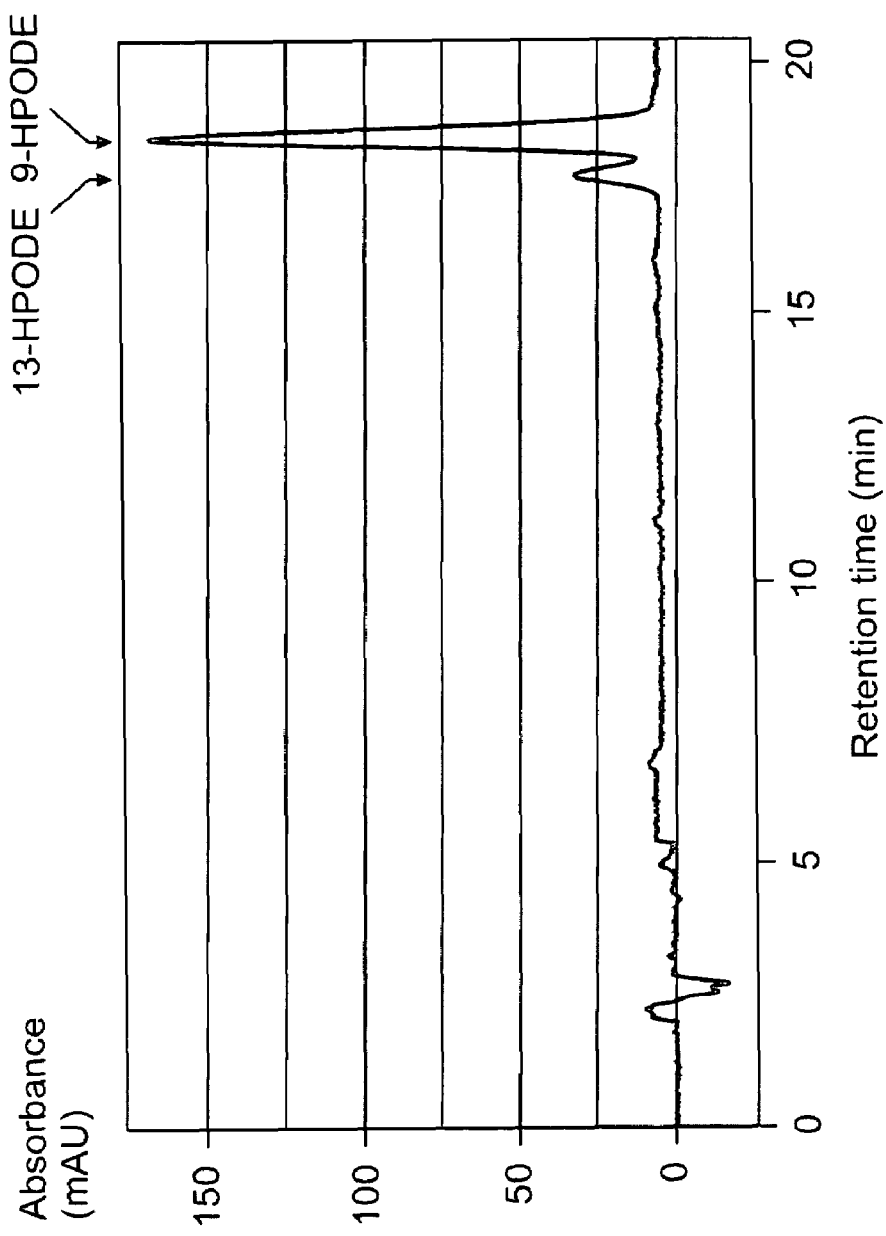
Figure 13C:
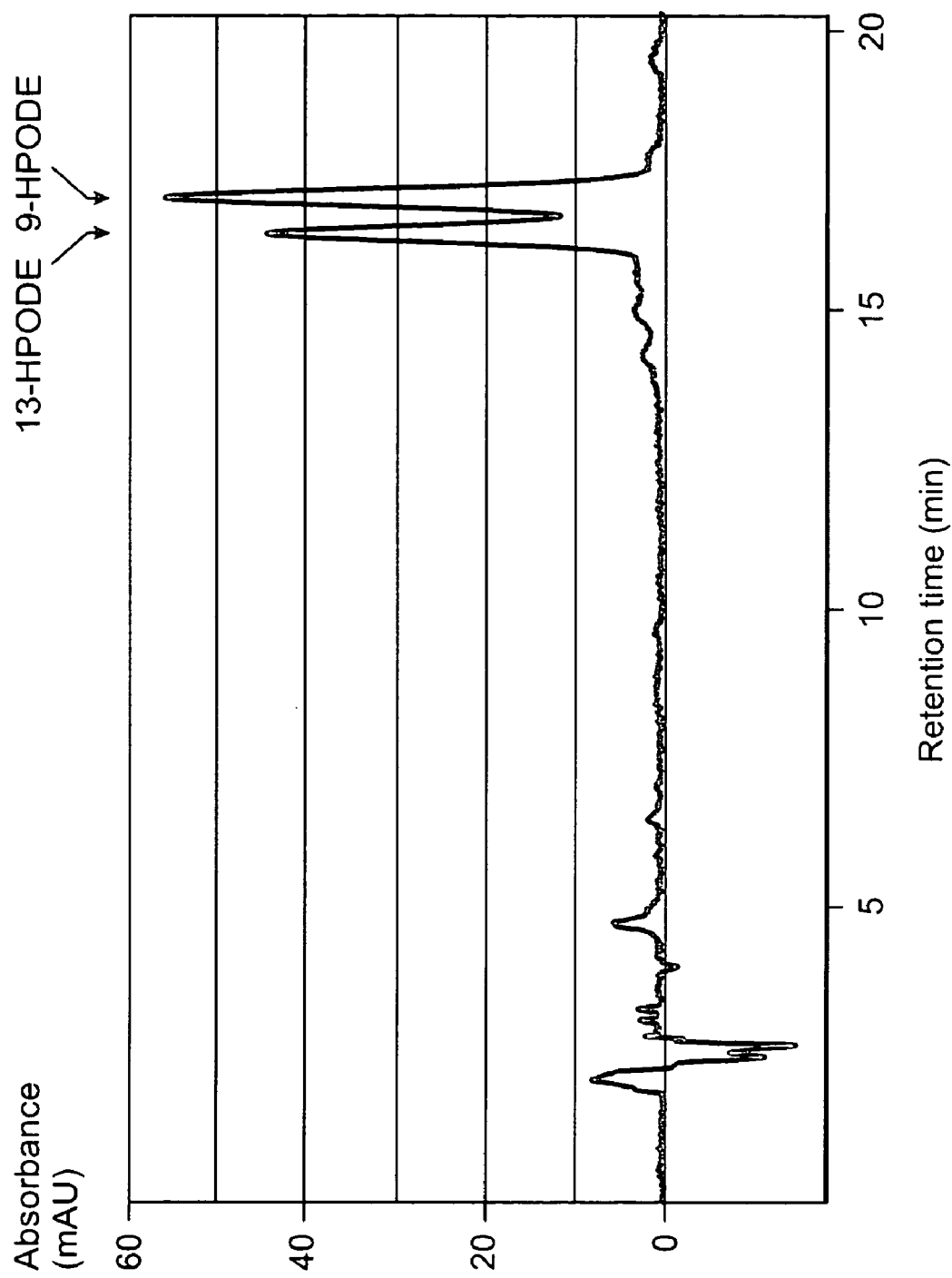
Figure 13D:
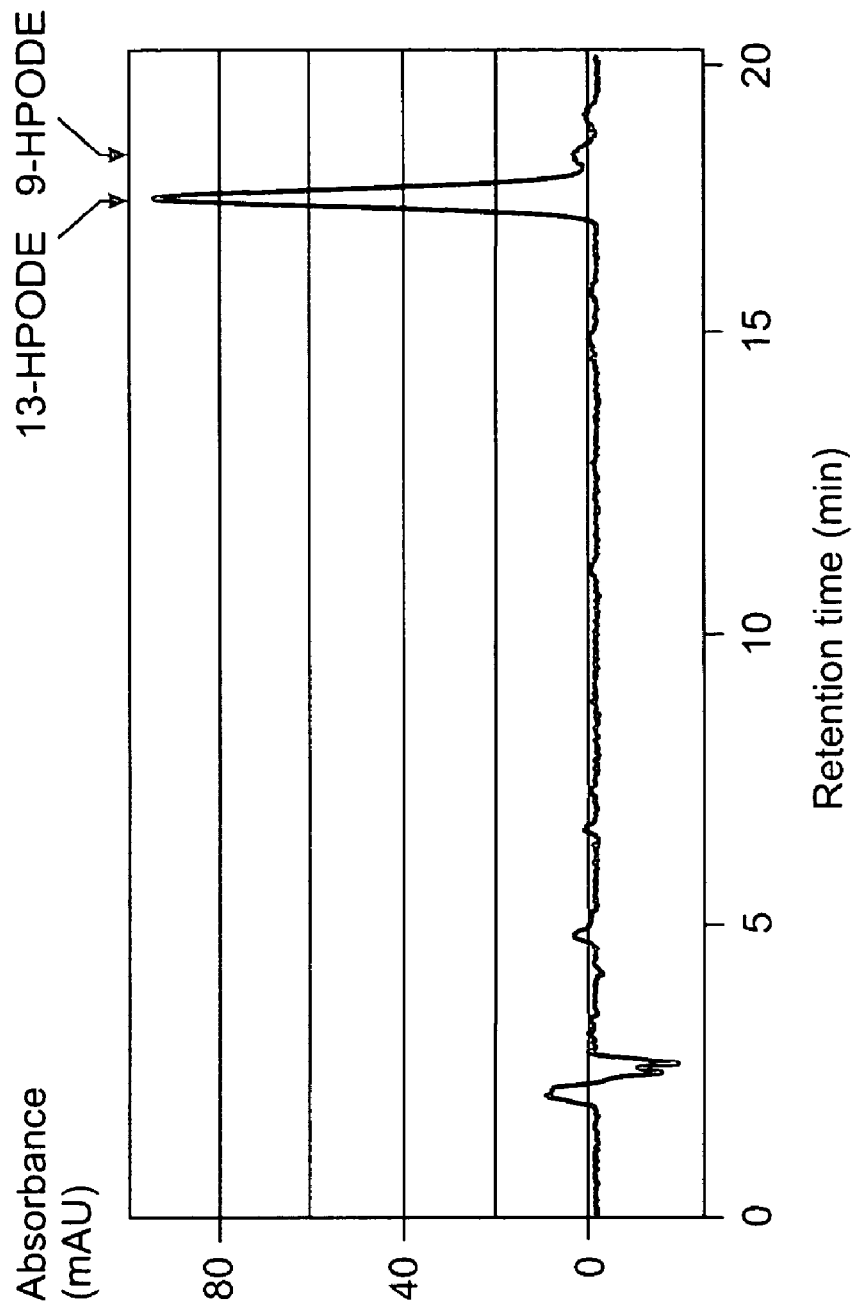

Analyses of the chromatograms revealed that mainly 9-HPODE was formed by LOX enzymes extracted from mature barley embryos of cv. Barke (FIG. 13B), whereas both 9- and 13-HPODE were formed in extracts of mature embryos of the low-LOX line G (FIG. 13C). Extracts of mutant D112 embryos formed very low amounts of 9-HPODE, but high amounts of 13-HPODE, thus verifying the absence of LOX-1 activity (FIG. 13D). Accordingly, embryo extracts of mutant D112 formed much less 9-HPODE than those of wild-type barley lines.

Barley malt. Barley malt contains two major LOX activities, derived from LOX-1 and LOX-2. Where LOX-1 catalyzes the formation of 9-HPODE, LOX-2 action generates 13-HPODE. To examine the effect of mutations in LOX-encoding genes on the formation of HPODE in malt extracts, HPLC analyses were performed with extracts prepared from malt derived from cv. Barke, barley low-LOX line G and mutant D112.

Samples of crude protein extract from malt were made in the following way. One malted barley grain was placed between two pieces of weighing paper, and hammered gently to produce a homogenous flour. All of the subsequent handlings, incubation mixtures and HPLC analysis methods were identical to those described the previous section of the instant Example relating to measurement of LOX products in embryo extracts.

For HPLC analysis was used a standard mixture of 9(S)-hydroperoxy-10(E),12(Z)-octadecadienoic acid [(9(S)-HPODE] and 13(S)-hydroperoxy-9(Z), 11(E)-octadecadienoic acid [(13(S)-HPODE], as illustrated in FIG. 14A. Analysis of the HPODE forming activity in extracts of malted Barke, low-LOX and D112 demonstrated a 60:40 distribution of the 9- and 13-HPODE-forming activities in malt of cv. Barke (FIG. 14B), some 9-HPODE-forming activity in malt derived form low-LOX barley (FIG. 14C), and very low levels of 9-HPODE formation in malt of mutant D112 (FIG. 14D). These data demonstrate a pronounced lower formation of 9-HPODE in malt extracts of mutant D112 than in malt extracts derived from other barley lines.

Example 10

The Gene for LOX-1 in Barley Mutant D112 is Mutated

The nucleotide sequence of the gene for LOX-1 in mutant D112 [SEQ ID NO: 2] and in cv. Barke [SEQ ID NO: 1] were obtained and compared in order to determine the molecular basis for the null-LOX-1 phenotype of mutant D112, which has been found to be characterised by the absence of the corresponding LOX-1 enzyme in the grain.

Genomic barley DNA from mutant D112 and wild-type cv. Barke were isolated from leaf tissues of seedlings using the Plant DNA Isolation Kit (Roche Applied Science), according to the manufacturer's recommendations. A 4,224-bp sequence flanking the protein coding region for LOX-1 in the genomic DNA of mutant D112 and cv. Barke was amplified by PCR using the primers 5'>GAAAGCGAGGAGAGGAG-GCCAAGAACAA<3' [SEQ ID NO: 9] and 5'>TTAT-TCATCCATGGTTGCCGATGGCTTAGA<3' [SEQ ID NO: 10]. Basis for the primer sequences was the genomic sequence of the gene for LOX-1 (van Mechelen et al., 1995; Rouster et al., 1997; a schematic drawing of the genomic sequence spanning the start and stop codons of the region encoding LOX-1 is shown in FIG. 15). The PCR reactions consisted of 100 ng genomic DNA in a 20-µl volume containing 5 pmol of each primer and 3.5 U Expand High Fidelity polymerase (Roche Applied Science). The PCR amplifications were carried out in an MJ cycler, using the following cycling parameters: 2 min at 96° C. for 1 cycle; 1 min at 95° C., 1 min at 69° C., and 5 min at 72° C. for 30 cycles; 10 min at 72° C. for 1 cycle. The PCR products were separated on 1.0% agarose gels. DNA fragments, corresponding in length to the amplified region, were purified using Qiaex II gel extraction kit (Qiagen), and inserted into the plasmid vector pCR2.1-TOPO (Invitrogen). The nucleotide sequence of both strands of the coding regions was determined using the dideoxynucleotide chain termination reaction with specific oligonucleotide primers and analysed on a MegaBACE 1000 DNA sequencer (Amersham). Sequence comparisons were performed using the Lasergene sequence analysis software package ver. 5 (DNASTAR).

In a direct comparison between the sequence for LOX-1 of wild-type cv. Barke [SEQ ID NO: 1] and mutant D112 [SEQ ID NO: 2], the nucleotide sequence of the mutant revealed one point mutation in the form of a G→A substitution at position 3574 in exon 7 (FIG. 15; FIG. 16). The wild-type sequence for LOX-1 encodes a 862-residue-long protein [SEQ ID NO: 3], with a predicted mass of 96.4 kDa. In contrast, the mutation at position 3574 in the corresponding sequence of mutant D112 causes the introduction of a premature stop codon.

The stop-codon in the LOX-1 encoding gene of mutant D112 is predicted to result in a C-terminal truncation of 197 amino acids of the correspondig protein, thus encoding a 74.2-kDa protein, the sequence of which is listed in [SEQ ID NO: 4].

Example 11

The Gene for LOX-1 in Barley Mutant A618 is Mutated

Preparation of genomic DNA, PCR reactions and DNA sequence determination and analyses of genomic DNA of barley mutant A618 and wild-type cv. Neruda were identical to those described for mutant D112 and cv. Barke in Example 10.

Comparison of the nucleotide for LOX-1 of barley mutant A618 [SEQ ID NO: 6] with that of the parental cv. Neruda [SEQ ID NO: 5] showed that the mutant sequence has one point mutation, corresponding to a G→A substitution at position 2311 in the genomic sequence (FIG. 15; FIG. 16).

The wild-type sequence for LOX-1 of cv. Neruda encodes a 862-residue-long protein [SEQ ID NO: 7], with a predicted mass of 96.4 kDa. In contrast, the mutation at position 2311 in the corresponding sequence of mutant A618 mutates the intron 3 donor site. This causes a splice error in intron 3, theoretically leading to a premature stop codon in the intron 3 after translation of 399 amino acids.

The inframe stop-codon in the gene for LOX-1 of mutant A618 will result in a truncated translated protein of 44.5 kDa [SEQ ID NO: 8].

Example 12

RT-PCR Detection of Transcripts for LOX-1

Barley plants of cv. Vintage, mutant line G (low-LOX, PCT application PCT/IB01/00207 published as WO 02/053721A1 to Douma et al.), cv. Barke, and mutant D112 were grown in a greenhouse during springtime 2002 in Copenhagen, Denmark. The ears were tagged at the day of flowering, and spikes were harvested at 20, 40 and 60 days after flowering (DAF). The spikes were kept at –80° C. until all of the samples could be processed simultaneously. A total of 10 embryos per time point were dissected from the developing caryopsis, and RNA was extracted using the FastRNA, Green RNA isolation kit (Qbiogene), using the manufacturer's recommendations.

Template for the RT-PCR reactions consisted of 100 ng RNA of the embryos described above. 20-μl RT-PCR reactions contained 50 pmol of each primer and 5 U RT-PCR enzyme mix (Promega). The RT-PCR amplifications were carried out in an MJ cycler: 45 min at 48° C. for 1 cycle; 1 min at 95° C. for 1 cycle; 1 min at 94° C., 1 min at 65° C. and 1 min at 72° C. for 30 cycles; and finally 10 min at 72° C. for 1 cycle. A forward primer, 5'>AGGGACTGCCGGAC-GATCTCA<3' [SEQ ID NO: 11], and a reverse primer, 5'>GCCAGCTCCGGCACACTT<3' [SEQ ID NO: 12], were used to generate a RT-PCR fragment of 292 bp. The RT-PCR products were separated on a 1.0% agarose gel. DNA fragments, corresponding in length to the amplified region, were purified using the Qiaex II gel extraction kit (Qiagen), and inserted into the plasmid vector pCR2.1-TOPO (Invitrogen). The nucleotide sequence of the plasmid insert was sequenced using an ABI Prism 310 Genetic Analyzer (ABI). DNA sequence comparisons were performed using the Lasergene sequence analysis software package ver. 5 (DNASTAR).

The resulting PCR product spanned the region corresponding to nucleotide positions 3283 to 3659 in the genomic clone [SEQ ID NO: 1]. This region comprised intron 5 with a length of 83 bp, which was absent from the RT-PCR template in a DNA-free RNA preparation (FIG. 17A). Since DNA sequence analysis confirmed that the isolated fragment was an integral part of the gene for LOX-1 and verified the absence of the intron 5 sequence, it could be excluded that false amplification yielded fragments from the barley gene for enzyme LOX-2 (FIG. 17D). Accordingly, the amplified fragment represented the product of an RNA transcript amplification.

Comparative RT-PCR analysis of RNA purified from barley embryos 20, 40 and 60 DAF of cv. Vintage and mutant line G revealed that the levels of transcripts for LOX-1 are similar for the two varieties at similar developmental stage. The transcript level for LOX-1 is gradually increasing in the time period from 20 DAF to 60 DAF (FIG. 17B).

In contrast, however, a marked difference was observed when a similar data set was examined for cv. Barke and mutant D112. Here, the RT-PCR experiments revealed that the LOX-1 transcripts in mutant D112 were substantially lower in abundance when compared with those of cv. Barke (FIG. 17C).

To summarize, the observations may bee explained by a potential mutation in the promoter region of the gene for LOX-1 in mutant D112. Other yet unknown factors may be involved in the transcriptional regulation of the gene for LOX-1 in mutant D112. In this respect, it cannot be exluded that the stop codon in the transcript for LOX-1 of mutant D112 confers nonsense-mediated mRNA decay (Isshiki et al., 2001).

Example 13

Genetic Detection of Barley Mutants Carrying the D112 Mutation

Modern barley breeding strategies comprise often biotechnological technologies to accelerate the process from mutagenesis to commercialization. Therefore, it may be useful to implement an early screening of plant material with respect to detection of single nucleotide polymorphisms in genes of interest. Using this technique with genomic DNA and combined with a high-throghput system, it may be possible to narrow down the number of breeding lines with 50% at the seedling stage.

CAPS assays. Cloning and sequencing of the gene for LOX-1 of mutant D112 progeny lines have shown that the mutation is transmitted to the following generation. This technique is laborious and not useful for practical barley breeding.

The mutation specific for the low-LOX line G could be identified in breeding material using a cleaved amplified polymorphic sequence assay (CAPS assay), as disclosed in Example 4 of PCT application PCT/IB01/00207 published as WO 02/053721A1 to Douma et al. However, the nature of the mutation in the gene for LOX-1 of mutant D112 cannot be used to generate an altered restriction map in a 60-bp region comprising the mutation.

SNP assays. An alternative solution to this is to perform an analysis comprising single nucleotide polymorphism (SNP). The SNP is a mutation point with at least two different nucleotide represented at one locus. The analysis is based on a combination of two sets of genomic PCR reactions. Both reactions contain a locus-specific primer, and one of the two SNP primers (one for each allele of the sequence). Two sets of PCR reactions are performed per plant line and the result of a PCR reaction is either that the SNP primer binds to sequences of the mutant or the wild-type allele (FIG. 18A). In one of several methods, the SNP analysis can be based on the identification of mutant lines by evaluating the banding pattern following electrophoresis of PCR products.

Genomic barley DNA from 17 breeding lines and from the wild-type cv Barke were isolated from leaf tissues of seedlings, using the Plant DNA isolation kit (Roche Applied Science) according to the manufacturer's recommendations.

The oligonucleotide primers used to amplify the SNP of the gene for wild-type LOX-1 were 5'>CAAGGTGCGGT-TGCTGGTGTC<3' [SEQ ID NO: 13] and 5'>CTCGCGCGTCTCCTTCCAC<3' [SEQ ID NO: 14]. For the corresponding gene of mutant D112 the primers were 5'>CAAGGTGCGGTTGCTGGTGTC<3' [SEQ ID NO: 13] and 5'>CTCGCGCGTCTCCTTCCAT<3' [SEQ ID NO: 15].

These primer combinations were used in PCR reactions to amplify DNA fragments of 166 bp comprising parts of the coding regions for LOX-1 of mutant D112 or cv. Barke (FIG. 18A).

The PCR reactions consisted of 100 ng genomic DNA in a 20-μl volume containing 25 pmol primer and 2.5 U FastStart Taq DNA polymerase (Roche), used according to the manufacturer's instructions. The PCR amplifications were carried out in an MJ cycler: 5 min at 96° C. for 1 cycle; 1 min at 95° C., 1 min at 70° C., 1 min at 72° C. for 20 cycles; and finally 10 min at 72° C. for 1 cycle.

The PCR products were separated on 1.0% agarose gels. DNA fragments, corresponding in length to the amplified region, were purified using Qiaex II gel extraction kit (Qiagen). The PCR products were sequenced directly using the dideoxynucleotide chain termination reaction on an ABI Prism 310 Genetic Analyzer. Sequence comparisons were performed using the Lasergene sequence analysis software package ver. 5 (DNASTAR).

Compiling the data from screening a total of 17 breeding lines by SNP analysis, as well as the experimental data from direct sequencing of the PCR products, yielded identical results. Based on these experiments, it can be concluded that the SNP technology can be used to confirm that a raw material comprises a gene sequence identical to that of the gene for LOX-1 of barley mutant D112 (FIG. 18B).

Example 14

Detection of Mutants in Sample Mixtures

The brewing industry may use mixtures of barley and malt for production of beer, a property that may mask unwanted, chemical characteristics of a specific malt variety. A simple confirmation for use of a specific seed material may comprise the amplification of the mutant gene by PCR analysis.

SNP analysis of mixed malt samples was performed using a sample mixture of mutant D112 and cv. Barke, and a sample mixture of mutant line G (PCT application PCT/IB01/00207 published as WO 02/053721A1 to Douma et al.), and cv. Barke. Six barley samples containing 0, 20, 40, 60, 80 and 100% grains of mutant D112 were analyzed. In another series, six barley samples containing 0, 20, 40, 60, 80 and 100% of mutant line G grains were analyzed. DNA was isolated from milled grains using the Nucleon Phytopure DNA isolation kit (Amersham), according to the manufacturer's recommendations.

The oligonucleotide primers used to amplify a 166-bp SNP of the gene for LOX-1 of mutant D112 were 5'>CAAGGT-GCGGTTGCTGGTGTC<3' [SEQ ID NO: 13] and 5'>CTCGCGCGTCTCCTTCCAT<3' [SEQ ID NO: 15]. The primers used to amplify a 370-bp SNP of the gene for LOX-1 of mutant line G were 5'>TACGTGCCGCGGGAC-GAGAAG<3' [SEQ ID NO: 16] and 5'>TGATCATGAC-CGGGTTGACGT<3' [SEQ ID NO: 17]. The PCRs were performed as a multiplex reactions using the four primers simultaneously (FIG. 19A). Each reaction comprised 100 ng genomic DNA in a 20-µl volume containing 50 pmol of each of the primer and 10 µl RedTaq polymerase solution (Sigma) according to the instruction provided by the supplier of the enzyme. The PCR amplifications were carried out in an MJ cycler: 1 min at 95° C. for 1 cycle; 1 min at 94° C., 1 min at 66° C., 30 sec at 72° C. for 25 cycles; and finally 10 min at 72° C. for 1 cycle. The PCR products were separated on 1.0% agarose gels. DNA fragments, corresponding in length to the amplified region, were purified using Qiaex II gel extraction kit (Qiagen), and inserted into the plasmid vector pCR2.1-TOPO (Invitrogen). The nucleotide sequence of both strands of plasmid inserts were determined using the dideoxynucleotide chain termination reaction with specific oligonucleotide primers and analysed on a MegaBACE 1000 DNA sequencer (Amersham). Sequence comparisons were performed using the Lasergene sequence analysis software package ver. 5 (DNASTAR).

The gel analysis presented in FIG. 19B revealed a positive SNP analysis for all of the samples dervied from mixtures containing grains of mutant D112. Similarly, it was possible to identify samples containing material from mutant line G. To summarize, genetic analyses can easily verify the use of barley mixtures comprising mutant LOX-plants of either mutant line G or mutant D112.

Example 15

Recombinant LOX-1 of Mutant D112 is Inactive

The gene for LOX-1 of mutant D112 was shown to contain a premature stop codon (cf. Example 10). Expression in planta of the gene was therefore expected to result in the synthesis of a truncated version of the corresponding LOX enzyme, containing only the first 665 amino acid residues found in wild-type LOX-1. The nucleotide sequence specifying the truncated version of LOX-1 was expressed in *E. Coli* cells to verify that it is enzymatically inactive, and cannot catalyze the formation of HPODEs in cells of barley mutant D112.

Plamids for expression of wild-type and mutant LOX-1 in *E. coli*. The entire open reading frame encoding LOX-1 was amplified by using a standard PCR protocol. The template was barley cDNA (van Mechelen, 1999), and the primers used were 5'>CATATGCTGCTGGGAGGGCTG<3' (SEQ ID NO: 18; the start codon marked in bold letters; the NdeI site underlined) and 5'>GAATTCTTAGATGGAGATGCTGTTGGG<3' (SEQ ID NO: 19; the complementary, wild-type stop codon shown in bold letters; the EcoRI site underlined). An amplified DNA fragment of 2,597 bp was obtained and purified. The PCR fragment was digested with NdeI-EcoRI and ligated to the large NdeI-EcoRI fragment of vector pET19b (Novagen), yielding the expression plasmid pETL1 in which the gene for LOX-1 is cloned downstream, in frame of a sequence for a 10-residue-long His-tail. DNA sequencing analyses verified that the plasmid insert contained a correct sequence.

The next experiment comprised construction of a plasmid for expression of the truncated version of LOX-1. The aim was to change codon no. 666 of the open reading frame for LOX-1 of pETL1 to a stop codon, such that protein synthesis in *E. coli* cells would generate a truncated version of LOX-1. To completely prevent read through of the stop-codon by ribosomes in *E. coli*, an expression plasmid was constructed in which all codons downstream of that for no. 665 of LOX-1 in pETL1 were removed and replaced by the stop codon TGA. The following protocol was used. A 129-bp fragment was amplified from pETL1 using PCR in the presence of the primers 5'>CTACCCGTACGCGGCGGACGGGCT<3' ([SEQ ID NO: 20]; annealing upstream of the mutation in the gene for LOX-1 of mutant D112; BsiWI site underlined) and 5'>TCCTGAATTCACGCCTGCACCTCCGTATCGC<3' ([SEQ ID NO: 21]; EcoRI site underlined; bold letters indicate the complementary sequence of the introduced stop codon). The amplification introduced a stop codon and an EcoRI site to the fragment. This was subsequently digested with BsiWI-EcoRI and ligated to the large BsiWI-EcoRI fragment of plasmid pETL1. The resulting expression plasmid was named pETL2, and the correct sequence of the insert was verified by DNA sequencing.

Transformed *E. coli* cells synthesize recombinant LOX proteins. *E. coli* BL21 cells, purchased from Novagen, were seperately transformed with vector pET19b and the expression plasmids pETL1 and pETL2 (described above). Bacterial cells harboring the plasmids were inoculated in standard Luria Broth (LB) medium and grown for 2 h at 37° C. Thereafter, 1 mM IPTG was added to induce expression of the heterologous genes, and the cultures were grown overnight at 20° C. The cells were harvested by centrifugation for 1 min at 14,000×g, followed by resuspension of the cell pellets in a denaturation solution consisting of a 50-mM Na-phosphate buffer supplemented with 6 M guanidine hydrocloride, 0.3 M NaCl and 10 mM imidazole. Following sonication on ice, the lysed cells were centrifuged for 1 min at 14,000×g and the supernatant was mixed with Ni-resins (Novagen), followed by a 30-min incubation at 4° C. The Ni-resins were precipitated by centrifugation and washed twice with the denaturation solution described above. Finally, His-tagged proteins were eluted twice from the resins using a 50-mM Na-phosphate buffer supplemented with 0.3 M NaCl and 0.5 M imidazole. Aliquots of fractionated, eluted samples were separated by SDS-PAGE (FIG. 20). Distinct bands of ~100 kDa, corresponding to LOX-1, and ~66 kDa, corresponding to the calculated mass of truncated LOX-1, were obtained from cells carrying pETL1 and pETL2, respectively. Cells carrying pET19b yielded no bands in the eluted fractions.

The truncated version of LOX-1 is inactive. *E. coli* BL21 carrying pET19b, pETL1, and pETL2 were inoculated in standard LB medium and grown for 2 h at 37° C. Thereafter, 1 mM IPTG was added to induce expression of the heterologous genes, and the cultures were grown overnight at 20° C. The cells were harvested by centrifugation for 1 min at 14,000×g. Cell lysates were obtained by resuspending the cell pellets in a mixture of BugBuster and Benzonase (Novagen). LOX activity was measured in the lysates using a lipoxygenase assay reagent containing 6.25 mM 3-dimethylaminobenzoic acid, 0.3125 mM linoleic acid, 0.1 mM 3-methyl-2-benzothiazolinehydrazone, and 0.05 mg/ml hemoglobin. 180 µl of the reagent was mixed with 10 µl of the respective cell lysate and incubated 10 min at room temperature. The amount of indamine produced during the incubation, determined spectrophotometrically as the absorbance at 595 nm, corresponds to the lipoxygenase activity of the cell lysate. While cells transformed with pETL1 (producing His-tagged LOX-1) showed large LOX-1 activity, cells producing mutant D112-specific, truncated LOX-1 had the same LOX activity as control cells transformed with the vector only (Table 8). This demonstrates that the truncated LOX-1 of barley mutant D112 is inactive.

Example 16

Transgenic Barley Plants

Plasmid constructs. Gene sequences are inserted into the polylinker region of standard plasmid vectors, such as pUC18. The inserts are listed in FIG. 21. In one construct (FIG. 21A), the maize ubiquitin-1 promoter (Christensen et al., 1992; Jensen et al., 1996)—including intron 1 of the same gene—directs transcription of the bar gene (White et al., 1990), which encodes the selectable marker phoshinothricin acetyl transferase (PAT). In a second construct, designed for sense suppression of the gene for LOX-1 (Dougherty and Parks, 1995), the open reading frame for barley LOX-1 is inserted immediately downstream of the maize ubiquitin-1 promoter and intron 1 (FIG. 21B). A construct for silencing the expression of the barley gene for LOX-1 is shown in FIG. 21C. Expression of this construct in barley cells confers total silencing of said gene by formation of intron-spliced hairpin RNA, and is designed according to the data detailed in FIG. 1*a* of the publication by Smith et al. (2000). Specifically, the sequence denoted "Intron 1" of the construct in FIG. 21C is identical to the intron sequence shown in FIG. 1*a* of the publication by Smith et al. (supra). The sense and antisense arms of the construct in FIG. 21C represent opposite directions of the same ~200-bp-long fragment comprising a segment of the open reading frame encoding barley LOX-1, said segment of the reading frame located anywhere in the open reading frame for LOX-1. Alternatively, the 200-bp-long sequence is selected from the sequence downstream of the stop codon of the barley gene encoding LOX-1.

Transformation and regeneration of transgenic plants. Immature barley embryos from greenhouse-grown donor barley plants of cv. Golden Promise are bombarded with a mixture of plasmids containing the inserts shown in FIG. 21A, B for co-suppression of the barley gene encoding LOX-1, and a mixture of plasmids shwon in FIG. 21A, C for silencing of said gene. Transformation, selection of transformed cells, and propagation of transgenic plants is performed as detailed by Wan and Lemaux (1994) and Jensen et al. (supra).

The transgenic plants are grown for several generations, or pollinated with a different barley cv., followed by identification of off-spring plants with the desired phenotype. Two or more generations may be grown to ensure that expression of the desired phenotypic characteristic is stably maintained and inherited. Seeds are harvested to examine that the desired phenotypic characteristic has been achieved.

To examine the effects of co-suppression or silencing of the barley gene encoding LOX-1, transgenic kernels are first analyzed for enzymic activity derived from LOX-1, as detailed in Example 1 of the instant publication. Transgenic kernels having no or very little LOX-1 activity are subsequently examined in malting and brewing experiments as detailed for null-LOX-1 kernels in Example 5 and Example 6 of the instant publication. In addition, extracts of the transgenic kernels are analyzed to identify those having a negative effects on the growth of *Aspergillus* fungi, using methods as described in U.S. Pat. No. 5,942,661 to Keller.

Example 17

Green Note Compounds

The process for production of green note compounds comprises:

(i) Converting null-LOX-1 barley kernels into finely ground flour;

(ii) Suspending the flour into water or a specified buffer;

(iii) Incubating the suspension. Alternatively, reacting the flour suspension with (a) a fatty acid (linoleic acid or linolenic acid or a mixture thereof); or (b) a hydroperoxide lyase enzyme having specificity for 13-HPODE or 13-HPOTE or both; or (c) a mixture comprising said fatty acids and said enzyme;

(iv) Reacting the resulting aldehydes with alcohol dehydrogenase;

(v) Purification of aldehydes or alcohols and preparation of a useful prepartion of the fragance or flavor composition.

TABLE 1

Total LOX activity in embryo extracts of raw mutants (generation M3) and progeny (generations M4 and M5)

| Embryo extracts | Total LOX activity $A_{595}$ units | Lines tested number | Standard deviation % |
|---|---|---|---|
| EXPERIMENT 1 | | | |
| Generation M3 | | | |
| mutant D112 | 0.407 | 4 | 5.8 |
| cv. Barke | 1.245 | 4 | 7.6 |
| cv. Barke (heat inactivated) | 0.213 | 2 | 1.5 |
| Generation M4 | | | |
| mutant D112 | 0.335 | 12 | 1.5 |
| cv. Barke | 0.738 | 2 | 3.2 |
| cv. Barke (heat inactivated) | 0.168 | 4 | 6.5 |
| Generation M5 | | | |
| mutant D112 | 0.294 | 90 | 4.1 |
| cv. Barke | 0.963 | 90 | 7.5 |
| cv. Barke (heat inactivated) | 0.165 | 4 | 1.2 |

TABLE 1-continued

Total LOX activity in embryo extracts of raw mutants (generation M3) and progeny (generations M4 and M5)

| Embryo extracts | Total LOX activity $A_{595}$ units | Lines tested number | Standard deviation % |
|---|---|---|---|
| EXPERIMENT 2 | | | |
| Generation M3 | | | |
| mutant A618 | 0.221 | 4 | 2.6 |
| cv. Neruda | 0.721 | 7 | 3.6 |
| cv. Barke (heat inactivated) | 0.175 | 2 | 0.6 |
| Generation M4 | | | |
| mutant A618 | 0.222 | 40 | 2.1 |
| cv. Neruda | 0.684 | 90 | 5.8 |
| cv. Barke (heat inactivated) | 0.168 | 4 | 1.3 |

TABLE 2

Comparison of agronomic performance

| Property | Mutant D112 | Wild-type, cv. Barke |
|---|---|---|
| Date of sowing (year 2003) | 21 March | 21 March |
| Length at maturity (cm) | 76 | 76 |
| Heading date (year 2003) | 14 June | 14 June |
| Powdery mildew | 0 | 0 |
| Spot blotch[a] | 2 | 1 |
| Scald[a] | 2 | 3 |
| Leaf rust[a] | 1 | 1 |
| Lodging[a] | 1 | 1 |
| Date of maturity (year 2003) | 31 July | 31 July |
| Yield[b] | 100 | 100 |

[a] On a scale from 0 to 9, where 0 represents no infection or lodging and 9 represents extremely infection or lodging.
[b] Relative, average yield of three replication at two different locations.

TABLE 3

Analyses following pilot malting trials

| Property | Cv. Barke, harvest 2002, Denmark | Mutant D112, harvest 2002/2003 New Zealand |
|---|---|---|
| BARLEY | | |
| Moisture content (%) | 11.2 | 12.1 |
| Nitrogen (%) | 10.7 | 12.6 |
| Starch (%) | 63.7 | 62.3 |
| β-Glucan, dry (%) | 3.8 | 4.2 |
| Germination after 72 h (%) | 98 | 96 |
| Germination index (scale 1 to 10) | 7.3 | 5.6 |
| Water sensitivity (%) | 59 | 66 |
| β-Amylase activity (U/g) | 1032 | 1505 |
| Predicted diastatic power | 382 | 555 |
| Grading, >2.5 mm (%) | 95.9 | 96.6 |
| 1000-kernel weight (g) | 46.8 | 54.4 |
| MALT | | |
| Moisture content (%) | 4.3 | 4.6 |
| Dry extract, fine (%) | 82.31 | 80.22 |
| Saccharification (min) | 10 | 10 |
| Clarity of wort, visuel | clear | clear |
| Clarity of wort (EBC units) | 1.24 | 3.48 |
| Wort color (EBC units) | 2.5 | 2.3 |
| Nitrogen, dry (%) | 1.61 | 2.09 |
| Nitrogen, soluble (%) | 0.64 | 0.65 |
| Kolbach index (%) | 39 | 31 |
| β-Glucan in wort (mg/l) | 192 | 220 |
| Friability (%) | 94.8 | 82.8 |
| Modification (%) | 95 | 95 |
| Homogenity (%) | 83 | 84 |
| pH | 6.0 | 6.1 |
| β-Amylase activity (U/g) | 937 | 1336 |
| Predicted diastatic power (WK) | 379 | 512 |
| α-Amylase activity (U/g) | 179 | 238 |

TABLE 4

Reduced levels of T2N in products of mutant D112.

| | Raw material | |
|---|---|---|
| Free T2N | Mutant D112 ppb | cv. Barke |
| Malt | 530 | 1488 |

TABLE 5

Effects of beer storage on flavor

| Experiment | Free T2N ppb | Papery[a] | Oxidized[a] rating | Aged[a] | Flavor[b] |
|---|---|---|---|---|---|
| BEER OF MUTANT D112 Storage at 37° C. | | | | | |
| 0 week (fresh beer) | 0.01 | 0.3 | 0.0 | 0.0 | 3.0 |
| 1 week | 0.02 | 0.9 | 0.7 | 1.0 | 2.3 |
| 2 weeks | 0.02 | nd | nd | nd | nd |
| 3 weeks | 0.02 | nd | nd | nd | nd |
| 4 weeks | 0.03 | nd | nd | nd | nd |
| CONTROL BEER OF cv. BARKE Storage at 37° C. | | | | | |
| 0 week (fresh beer) | 0.01 | 0.4 | 0.1 | 0.1 | 3.1 |
| 1 week | 0.04 | 1.9 | 0.5 | 1.5 | 1.6 |
| 2 weeks | 0.05 | nd | nd | nd | nd |
| 3 weeks | 0.06 | nd | nd | nd | nd |
| 4 weeks | 0.08 | nd | nd | nd | nd |

[a] Scale of rating—0: not present; 1: weak; 2: notably; 3: middle; 4: strong; 5: extreme. Low values are preferred
[b] Scale of rating is from 1 to 5; high values are preferred
nd = not determined

TABLE 6

THAs in beers produced from malt of normal barley and mutant D112.

| Malt type | 9,12,13-THA ppm | 9,10,13-THA | 9,12,13-THA:9,10,13-THA ratio |
|---|---|---|---|
| Control | 3.7 | 0.6 | 6.2 |
| Mutant D112 | 0.8 | 0.6 | 1.3 |

TABLE 7

THAs in commercially available beers

| Brand | Label description | 9,12,13-THA ppm | 9,10,13-THA ppm | 9,12,13-THA:9,10,13 THA ratio |
|---|---|---|---|---|
| Stella Artois (Belgium) | 12/12/03 4512:11 | 7.5 | 1.5 | 5.0 |
| Kirin Beer (UK) | 30/11/03 B L2315 23:34 | 4.8 | 1.1 | 4.4 |
| Pilsner Urquell | 06.02.04 LC2 037 | 7.9 | 0.9 | 8.8 |
| Faxe Fad | 040204 E09:33 | 5.1 | 1.0 | 5.1 |
| Carlsberg Light | | 2.7 | 0.4 | 6.2 |
| Carls Special | | 5.8 | 1.0 | 5.7 |
| Classic Hvede | | 6.7 | 0.8 | 8.6 |
| Carls Lager | | 5.6 | 1.1 | 5.4 |
| Blanche des Honnelles Brasserie de L'abbaye des Rocs. | best before 2007 | 7.3 | 0.7 | 10.9 |
| San Miguel | 280704 L11 16:39 | 7.7 | 1.4 | 5.5 |
| Peroni Gran Reserva Birra (Italy) | 06/04 L3 163 1 22 | 7.2 | 1.0 | 7.2 |
| Heineken (Denmark) | 08042004 | 3.4 | 0.7 | 4.8 |
| Labatt Blue | aug03 L27BN | 2.8 | 0.7 | 3.9 |
| Kronenbourg 1664 | 05/04 1400301 | 5.6 | 1.2 | 4.6 |
| Newcastle Brown Ale | 310504 L1475 | 3.1 | 0.7 | 4.5 |
| Anchor Liberty Ale | Feb 05 | 3.1 | 0.7 | 4.3 |
| Leffe | 29/12/04 22:08 | 6.0 | 1.2 | 4.9 |
| De Koninck B. | 14/02/04 | 4.8 | 1.1 | 4.3 |
| Anchor Steam Beer (USA) | Aug 04 | 3.4 | 0.7 | 4.7 |
| Foster's (Edingburgh, UK) | 31/7/04 24 L211 21:58 | 3.9 | 0.9 | 4.1 |
| Pilsner Urquell (The Czech Republic) | L22.07.04 | 12.7 | 2.0 | 6.2 |
| Bombardier English Premium Bitter (UK) | 30/11/03 A L3034 04:49 | 3.0 | 0.5 | 5.6 |
| Curim Gold Celtic Wheat Beer (Ireland) | L2689 BBEDEC03 | 12.9 | 0.9 | 14.4 |
| O'hara's Celtic Stout (Ireland) | L2701 BBDEC03 | 7.8 | 0.8 | 9.6 |
| Erdinger Pikantus (Germany) | 01-2004 L105101 | 15.9 | 1.2 | 12.9 |
| Michelob Lager (UK) | 12JUN03 A39 10 DEC03 | 6.2 | 0.9 | 7.1 |
| Spaten München (Germany) | 04.04 L11833 | 4.2 | 1.0 | 4.2 |
| Kilkenny Draught (Ireland) | 28/03/04 G310:00 | 1.4 | 0.3 | 4.0 |
| Guinness Draught (Ireland) | 300504 G3 PD310803 07:01 | 2.2 | 0.6 | 3.5 |
| Oktoberfestbier Spaten München (Germany) | 08.04 L21433 | 3.6 | 0.6 | 5.9 |
| Sol (Mexico) | 210204 DI □1023A2102*3 | 3.2 | 0.9 | 3.5 |
| Badger Golden Champion Ale (UK) | Jun04 13:35 L3150H | 3.5 | 0.5 | 7.3 |
| Rolling Rock (Interbrew Belgium) | 04/2004 1 03153 | 5.9 | 0.9 | 6.8 |
| Bush Beer (Belgium) | Not readable | 7.7 | 1.1 | 7.2 |
| Corona Extra (Eorocermex. Belgium) | DK 240404 03103:33 | 4.1 | 0.5 | 7.7 |
| Staropramen Premium Prague Beer | 05.06.04I 18:15 | 6.1 | 0.9 | 6.8 |
| Miller Genuine Draft (EU) | 16-06-2004 3F16 12:42 | 2.9 | 0.6 | 4.8 |
| Old Foghorn Barley wine style Ale | Mar04 | 4.7 | 0.7 | 6.9 |

TABLE 8

Lipoxygenase activity from crude cell extracts from cells carrying the indicated vectors, grown over night in LB and IPTG

| Plasmid | Activity[a] |
|---------|-------------|
| pET19b  | 0.0723 ± 0.0002 |
| pETL1   | 1.0612 ± 0.004 |
| pETL2   | 0.0690 ± 0.0002 |

[a]The results are given as the mean value of four individual measurements with variation indicated.

TABLE 9

Sequence listing

| SEQ ID | Sequence type | Description |
|--------|---------------|-------------|
| NO: 1  | Nucleic acid | Barley genomic sequence of cv. Barke spanning the start and stop codons of the gene encoding LOX-1 |
| NO: 2  | Nucleic acid | Barley genomic sequence of mutant D112 spanning the segment corresponding to the region between the start and stop codons of the gene encoding LOX-1 of cv. Barke |
| NO: 3  | Protein | Protein sequence of full-length LOX-1 protein of cv. Barke |
| NO: 4  | Protein | Protein sequence of inactive, truncated LOX-1 of mutant D112 |
| NO: 5  | Nucleic acid | Barley genomic sequence of cv. Neruda spanning the start and stop codons of the gene encoding LOX-1 |
| NO: 6  | Nucleic acid | Barley genomic sequence of mutant A618 spanning the segment corresponding to the region between the start and stop codons of the gene encoding LOX-1 of cv. Neruda |
| NO: 7  | Protein | Protein sequence of full-length LOX-1 protein of cv. Neruda |
| NO: 8  | Protein | Protein sequence of inactive, truncated LOX-1 of mutant A618 |
| NO: 9  | Nucleic acid | Oligonucleotide primer used for PCR amplification (sense primer; cf. Example 10) |
| NO: 10 | Nucleic acid | Oligonucleotide primer used for PCR amplification (antisense primer; cf. Example 10) |
| NO: 11 | Nucleic acid | Oligonucleotide primer used for PCR amplification (sense primer; cf. Example 11, FIG. 17) |
| NO: 12 | Nucleic acid | Oligonucleotide primer used for PCR amplification (antisense primer; cf. Example 11, FIG. 17) |
| NO: 13 | Nucleic acid | Oligonucleotide primer used for PCR amplification (sense primer; cf. Example 12, 15 and FIG. 18, 20) |
| NO: 14 | Nucleic acid | Oligonucleotide primer used for PCR amplification (antisense primer; cf. Example 12, FIG. 18) |
| NO: 15 | Nucleic acid | Oligonucleotide primer used for PCR amplification (antisense primer; cf. Example 12, 15 and FIG. 18, 20) |
| NO: 16 | Nucleic acid | Oligonucleotide primer used for PCR amplification (sense primer; cf. Example 14, FIG. 19) |
| NO: 17 | Nucleic acid | Oligonucleotide primer used for PCR amplification (antisense primer; cf. Example 14, FIG. 19) |
| NO: 18 | Nucleic acid | Oligonucleotide primer used for PCR amplification (sense primer; cf. Example 15) |
| NO: 19 | Nucleic acid | Oligonucleotide primer used for PCR amplification (antisense primer; cf. Example 15) |
| NO: 20 | Nucleic acid | Oligonucleotide primer used for PCR amplification (sense primer; cf. Example 15) |
| NO: 21 | Nucleic acid | Oligonucleotide primer used for PCR amplification (antisense primer; cf. Example 15) |

```
Organization Applicant
  Street: Gamle Carlsberg Vej 10
  City: Copenhagen-Valby
  State:
  Country: Denmark
  PostalCode: DK-2500
  PhoneNumber: +45 3327 5241
  FaxNumber: +45 3327 4764
  EmailAddress: lok@crc.dk
<110> OrganizationName: Carlsberg Research Laboratory
Application Project
<120> Title: Barley for production of flavor-stable beer
<130> AppFileReference: 1
<140> CurrentAppNumber:
```

-continued

```
<141> CurrentFilingDate:    __-__-__
Sequence
<213> OrganismName: Hordeum vulgare cv. Barke
<400> PreSequenceString:
atgctgctgg gagggctgat cgacaccctc acggggcga acaagagcgc ccggctcaag        60
ggcacggtgg tgctcatgcg caagaacgtg ctggacctca cgacttcgg cgccaccatc       120 atcgacggca tcggcgagtt cctcggcaag ggcgtcacct gccagcttat cagctccacc      180
gccgtcgacc aaggtaatca ctaccctcct ccggccttct cctctgttta ceagatatag      240 tatttctttc gtgtgggccg gcggccatgg atggatggat gtgtctggat cggctaaaga      300
agataggata gctagccctg gccggtcgtc tttacctgag catgggcata tgccatcgaa      360
aaaagagaca acagcatgca tgcatggtgc gcgcaccaga ccacgcagag caccggatgc      420
tcgagacaaa gcaacacaac aagcaaggac gacacgtcaa agcaacaca acaagcaagg      480 acggcacgtc aaaagcaaca caaacctaaa ctaaagcaca agacgtaag agcaagcaca      540 caatcagcag gctataaaca gttgtcatca aaaacaacgc tggaagagag agageaggaa      600 ggaagtagta gccatgaaaa attaaatcac cgggcgttgc tctttgccca acaattaatc      660
aagcaggata cgtggcatgt atagttcttg taagtaaact aagcatgtga tatgagaagg      720
tacgtggtgg tgcagacaac ggcggtcgcg ggaaggtggg cgcggaggcg gagctggagc      780
agtgggtgac gagcctgccg tcgctgacga cgggggagtc caagttcggc ctcaccttcg      840
actgggaggt ggagaagctc ggggtgccgg cgccatcgt cgtcaacaac taccacagct      900
ccgagttcct gcttaaaacc atcaccctcc acgacgtccc cggccgcagc ggcaacctca     960
ccttcgtcgc caactcatgg atctaccccg ccgccaacta ccgatacagc cgcgtcttct    1020
tcgccaacga cgtgcgtgga ttttcctcta ctttcctctc ctttcatttt caccgccttc    1080
gtcattcatg gtcgatcatt aagtcttgcc aggacastag atgatgagct aggagtggtt    1140
accacttagc agtacgtaca ttatttattc cgtgttggta gaaaaggata tggtttggtg    1200
cagatcgaca caagattgaa tgaaagttgc accgtggcac cgtggcagcg tggtaggtga    1260
aaataactgt tgcacggatc cacccacatg attgttttca tgaataaact ttttaaggat    1320
gtgtctagcc acatctagat gcatgtcaca taattattgc ataccassac gattaaatta    1380
agcataaaaa gaaaggaaa aaaatactca catatctcga cgtaagatca atgatatagt     1440
atttagatat gcaatattta tcttacatct aaacctttct tcattcctaa atataagaca    1500
tttgtaagat ttcactatgg acaacatacg aaacaaaatc agtggatctc tctatgcatt    1560
cattatgtag tctataataa aatctttaaa agatcgtata ttttgcaacg gagggagtaa    1620
aacataactt tttaatagta atgttgcacg gctccacact cgcagacgta cctgccgagc    1680
cagatgccgc cggcgctgaa gccgtaccgc gacgacgagc tccggaacct gcgtggcgac    1740
gaccagcagg gcccgtacca ggagcacgac cgcatctacc gctacgacgt ctacaacgac    1800
ctcggcgagg gccgccccat cctcggcggc aactccgacc cccttaccc cgccgcggc    1860 cgcacggagc gcaagcccaa cgccagcgac ccgagcctgg agagccggct gtcgctgctg    1920
gagcagatct acgtgccgcg ggacgagaag ttcggccacc tcaagacgtc cgacttcctg    1980
ggctactcca tcaaggccat cacgcagggc atcctgccgg ccgtgcgcac ctacgtggac    2040 accaccccg gcgagttcga ctccttccag gacatcatca acctctatga gggcggcatc    2100
aagctgccca aggtggccgc cctggaggag ctccgtaagc agttcccgct ccagctcatc    2160
aaggacctcc tccccgtcgg cggcgactcc ctgcttaagc tccccgtgcc ccacatcatc    2220
caggagasca agcaggcgtg gaggaccgac gaggagttcg cacgggaggt gctcgccggc    2280
```

| | |
|---|---|
| gtcaacccgg tcatgatcac gcgtctcacg gtgagtcagc gattatttgt tcattgtgtg | 2340 |
| tgtatggtgt ccatggtgag aaagtgcaga tcttgatttg cgttgggtcg catgcacgca | 2400 |
| tgctgcatgc atgcaggagt tcccgccaaa aagtagtctg gaccctagca agtttggtga | 2460 |
| ccacaccagc accatcacgg cggagcacat agagaagaac ctcgagggcc tcacggtgca | 2520 |
| gcaggtaatt ggtccaagcc atcgacatca actatgattt acctaggagt aattggtagc | 2580 |
| tgtagataat ttggcttcgt tgcaattaat ttgatgctgg ccgatcaagt gatcgtattg | 2640 |
| ggtttgaaat ttgcaggcgc tggaaagcaa caggctgtac atccttgatc accatgaccg | 2700 |
| gttcatgccg ttcctgatcg acgtcaacaa cctgcccggc aacttcatct acgccacgag | 2760 |
| gaccctcttc ttcctgcgcg cgacggcag gctcacgccg ctcgccatcg agctgagcga | 2820 |
| gcccatcatc cagggcggcc ttaccacggc caagagcaag gtttacacgc cggtgcccag | 2880 |
| cggctccgtc gaaggctggg tgtgggagct cgccaaggcc tacgtcgccg tcaatgactc | 2940 |
| cgggtggcac cagctcgtca gccactggta cgttctccac ggtcgatgtg attcagtcag | 3000 |
| tcgatgcaca caactgatc gaaatatgat tgattgaaac gcgcaggctg aacactcacg | 3060 |
| cggtgatgga gccgttcgtg atctcgacga accggcacct tagcgtgacg cacccggtgc | 3120 |
| acaagctgct gagcccgcac taccgcgaca ccatgaccat caacgcgctg gcgcggcaga | 3180 |
| cgctcatcaa cgccggcggc atcttcgaga tgacggtgtt cccgggcaag ttcgcgttgg | 3240 |
| ggatgtcggc cgtggtgtac aaggactgga agttcaccga gcaggactg ccggacgatc | 3300 |
| tcatcaagag gtacgtacct ggtaaatgtt atgaatgtgt aaaacaaatt gggcgtctcg | 3360 |
| ctcactgaca ggaacgtggt aaaaaaaatg caggggcatg gcggtggagg acccgtcgag | 3420 |
| cccgtacaag gtgcggttgc tggtgtcgga ctacccgtac gcggcggacg ggctggcgat | 3480 |
| ctggcacgcc attgagcagt acgtgagcga gcacccggcc atctactacc gaacgacgg | 3540 |
| cgtgctgcag ggcgatacgg aggtgcaggc gtggtggaag gagacgcgcg aggtcgggca | 3600 |
| cggcgacctc aaggacgccc catggtggcc caagatgcaa agtgtgccgg agctggccaa | 3660 |
| ggcgcgcacc accatcatct ggatcgggtc ggcgctgcat gcggcagtca acttcgggca | 3720 |
| gtacccctac gcggggttcc tcccgaaccg gccgacggtg agccggcgcc gcatgccgga | 3780 |
| gcccggcacg gaggagtacg cggagctgga gcgcgacccg gagcgggcct tcatccacac | 3840 |
| catcacgagc cagatccaga ccatcatcgg cgtgtcgctg ctggaggtgc tgtcgaagca | 3900 |
| ctcctccgac gagctgtacc tcgggcagcg ggacacgccg gagtggacct cggacccaaa | 3960 |
| ggccctggag gtgttcaagc ggttcagcga ccggctggtg gagatcgaga gcaaggtggt | 4020 |
| gggcatgaac catgacccgg agctcaagaa ccgcaacggc ccggctaagt ttccctacat | 4080 |
| gctgctctac cccaacacct ccgaccacaa gggcgccgct gccgggctta ccgccaaggg | 4140 |
| catccccaac agcatctcca tctaa | 4165 |

<212> Type: DNA
<211> Length: 4165
  SequenceName: SEQ ID NO: 1
  SequenceDescription: Barley genomic sequence of cv. Barke, spanning
the start and stop codons of the gene encoding LOX-1
Sequence
<213> OrganismName: Hordeum vulgare mutant D112
<400> PreSequenceString:

| | |
|---|---|
| atgctgctgg gagggctgat cgacaccctc acggggcga acaagagcgc ccggctcaag | 60 |
| ggcacggtgg tgctcatgcg caagaacgtg ctggacctca cgacttcgg cgccaccatc | 120 |
| atcgacggca tcggcgagtt cctcggcaag ggcgtcacct gccagcttat cagctccacc | 180 |

-continued

```
gccgtcgacc aagtaatca ctaccctcct ccggccttct cctctgttta caagatatag    240
tatttctttc gtgtgggccg gcggccatgg atggatggat gtgtctggat cggctaaaga    300
agataggata gctagccctg ccggtcgtc tttacctgag catgggcata tgccatcgaa     360
aaaagagaca acagcatgca tgcatggtgc gcgcaccaga ccacgcagag caccggatgc    420
tcgagacasa gcaacacaac aagcaaggac gacacgtcaa aagcaacaca acaagcaagg    480
acggcacgtc aaaagcaaca caaacctaaa ctaaagcaca aagscgtaag agcaagcaca    540
caatcagcag gctataaaca gttgtcatca aaaacaacgc tggaagagag agagaaggaa    600
ggaagtagta gccatgaaaa attaaatcac cgggcgttgc tctttgccca acaattaatc    660
aagcaggata cgtggcatgt atagttcttg taagtaasct aagcatgtga tatgagaagg    720
tacgcggtgg tgcagacaac ggcggtcgcg ggaaggtggg cgcggaggcg gagctggagc    780
agtgggtgac gagcctgccg tcgctgacga cgggggagtc caagttcggc ctcsccttcg    840
actgggaggt ggagaagctc ggggtgccgg gcgccatcgt cgtcaacaac taccacagct    900
ccgagttcct gcttaaaacc accaccctcc acgacgtccc cggccgcagc ggcaacctca    960
ccttcgtcgc caactcatgg atctaccccg ccgccaacta ccgatacagc cgcgtcttct   1020
tcgccaacga cgtgcgtgga ttttcctcta ctttcctctc ctttcatttt caccgccttc   1080
gtcattcatg gtcgatcatt aagtcttgcc aggacaatag atgatgagct aggagtggtt   1140
accacttagc agtacgtaca ttatttattc cgtgttggta gaaaaggata tggtttggtg   1200
cagatcgaca caagattgaa tgaaagttgc accgtggcac cgtggcagcg tggtaggtga   1260
aaataactgt tgcacggatc cacccacatg attgttttca tgaataaact tttttaaggat  1320 gtgtctagcc acatctagat gcatgtcaca taattattgc ataccaaaac gattaaatta   1380
agcataaaaa gaaaaggaaa aaaatactca catatctcga cgtaagatca atgatatagt   1440
atttagatat gcaatatta tcttacatct aaacctttct tcattcctaa atataagaca    1500
tttgtaagat ttcactatgg acaacatacg aaacaaaatc agtggatctc tctatgcatt   1560
cattatgtag tctataataa aatctttaaa agatcgtata ttttgcaacg gagggagtaa   1620
aacataactt tttaatagta atgttgcacg gctccacact cgcagacgta cctgccgagc   1680
cagatgccgg cggcgctgaa gccgtaccgc gacgacgagc tccggaacct gcgtggcgac   1740
gaccagcagg gcccgtacca ggagcacgac cgcatctacc gctacgacgt ctacaacgac   1800
ctcggcgagg gccgcccat cctcggcggc aactccgacc accccttaccc cgcgccgcgc   1860 cgcacggagc gcaagcccaa cgccagcgac ccgagcctgg agagccggct gtcgctgctg   1920
gagcagatct acgtgccgcg ggacgagaag ttcggccacc tcaagacgtc cgacttcctg   1980
ggctactcca tcaaggccat cacgcagggc atcctgccgg ccgtgcgcac ctacgtggac   2040 accaccccg gcgagttcga ctccttccag gacatcatca acctctatga gggcggcatc   2100
aagctgccca aggtggccgc cctggaggag ctccgcaagc agttcccgct ccagctcatc   2160
aaggacctcc tccccgtcgg cggcgactcc ctgcttaagc cccccgtgcc ccacatcatc   2220
caggagaaca agcaggcgtg gaggaccgac gaggagttcg cacgggaggt gctcgccggc   2280
gtcaacccgg tcatgatcac gcgtctcacg gtgagtcagc gattatttgt tcattgtgtg   2340
tgtatggtgt ccatggtgag aaagtgcaga tcttgatttg cgttgggtcg catgcacgca   2400
tgctgcatgc atgcaggagt tcccgccaaa aagtagtctg gaccctagca agtttggtga   2460
ccacaccagc accatcacgg cggagcacat agagaagaac ctcgagggcc tcacggtgca   2520
gcaggtaatt ggtccaagcc atcgacatca actatgattt acctaggagt aattggtagc   2580
```

-continued

```
tgtagacaat ttggccccgt tgcaactaat tcgatgccgg ccgatcaagt gatcgtattg    2640
ggtttgaaat ttgcaggcgc tggaaagcaa caggctgtac atccttgatc accatgaccg    2700
gttcatgccg ttcctgatcg acgtcaacaa cctgcccggc aacttcatct acgccacgag    2760
gaccctcttc ttcctgcgcg gcgacggcag gctcacgccg ctcgccatcg agctgagcga    2820
gcccatcatc cagggcggcc ttaccacggc aagagcaag gtttacacgc cggtgcccag     2880
cggctccgtc gaaggctggg tgtgggagct cgccaaggcc tacgtcgccg tcaatgactc    2940 cggggtggcac cagctcgtca gccactggta cgttctccac ggtcgatgtg attcagtcag    3000
tcgatgcaca caactgatc gaaatatgat tgattgaaac gcgcaggctg aacactcacg     3060
cggtgatgga gccgttcgtg atctcgacga accggcacct tagcgtgacg cacccggtgc    3120
acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcagggactg ccggacgatc    3300
tcatcaagag gtacgtacct ggtaaatgtt atgaatgtgt aaaacaaatt gggcgtctcg    3360
ctcactgaca ggaacgtggt aaaaaaatg cagggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc cgaacgacgg    3540
cgtgctgcag ggcgatacgg aggtgcaggc gtgatggaag gagacgcgcg aggtcgggca    3600
cggcgacctc aaggacgccc catggtggcc caagatgcaa agtgtgccgg agctggccaa    3660
ggcgtgcacc accatcatct ggatcgggtc ggcgctgcat gcggcagtca acttcgggca    3720 gtaccgcta gcggggttcc tcccgaaccg gcgacggtg agccggcgcc gcatgccgga     3780
gcccggcacg gaggagtacg cggagctgga gcgcgacccg gagcgggcct tcatccacac    3840
catcacgagc cagatccaga ccatcatcgg cgtgtcgctg ctggaggtgc tgtcgaagca    3900
ctcctccgac gagctgtacc tcgggcagcg ggacacgccg gagtggacct cggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt ttccctacat    4080
gctgctctac cccaacscct ccgaccacaa gggcgccgct gccgggctta ccgccaaggg    4140
catccccaac agcatctcca tctaa                                          4165
```

<212> Type: DNA
<211> Length: 4165
   SequenceName: SEQ ID NO: 2
   SequenceDescription: Barley genomic sequence of mutant D112
spanning the segment, corresponding to the region between the
start and stop codons of the gene encoding LOX-1 of cv. Barke
Sequence
<213> OrganismName: Hordeum vulga cv. Barke
<400> PreSequenceString:

```
MLLGGLIDTL TGANKSARLK GTVVLMRKNV LDLNDFGATI IDGIGEFLQK GVTCQLISST    60

AVDQDNGGRG KVGAEAELEQ WVRSLPSLTT GESKFGLTFD WEVEKLGVPG AIVVNNYHSS    120

EFLLKTITLH DVPGRSGNLT FVANSWIYPA ANYRYSRVFF ANDTYLPSQM PAALKPYRDD    180

ELRNLRGDDQ QGPYQEHDRI YRYDVYNDLG EGRPILGGNS DHPYPRRGRT ERKPNASDPS    240

LESRLSLLEQ IYVPRDEKFG NLKTSDFLGY SIKAITQGIL PAVRTYVDTT PGEFDSFQDI    300

INLYEGGIKL PKVAALEELR KQFPLQLIKD LLPVGGDSLL KLPVPNIIQE NKQAWRTDEE    360

FAREVLAGVN PVMITRLTEF PPKSSLDPSK FGDHTSTITA EHIEKNLEGL TVQQALESNR    420

LYILDHHDRF MPFLIDVNNL PGNFIYATRT LFFLRGDGRL TPLAIELSEP IIQGGLTTAK    480
```

```
SKVYTPVPSG SVEGWVWELA KAYVAVNDSG WHQLVSHWLN THAVMEPFVI STNPHLSVTH      540

PVHKLLSPHY RDTMTINALA ROTLINAGGI FEMTVFPGKF ALGMSAVVYK DWKFTEQGLP      600

DDLIKRGMAV EDPSSPYKVR LLVSDYPYAA DGLAIWHAIE QYVSEYLAIY YPNDGVLQGD      660

TEVQAWWKET REVGNGDLKD APWWPKMQSV PELAKACTTI IWIGSALHAA VNFGQYPYAG      720

FLPNRPTVSR RRNPEPGTEE YABLEROPER AFIHTITSQI QTIIGVSLLE VLSKHSSDEL      780

YLGQRDTPEW TSDPKALEVF KRFSDRLVEI ESKVVGMNHD PELKNRNGPA KFPYMLLYPN      840

TSDHKGAAAG LTAKGIPNSI SI                                              862

<212> Type: PRT
<211> Length: 862
   SequenceName: SEQ ID NO: 3
   SequenceDescription: Protein sequence of full-length
LOX-1 protein of cv. Barke
Sequence
<213> OrganismName: Hordeum vulgare mutant D112
<400> PreSequenceString:
MLLGGLIDTL TGANKSARLK GTVVLMRKNV LDLNDFGATI IDGIGEFLGK GVICQLISST       60

AVDQDNGGRG KVGAEAELEQ WVTSLPSLTT GESKFGLTFD WEVEKLGVPG AIVVNNYHSS      120

EFLLKTITLH DVPGRSGNLT FVANSWIYPA ANYRYSRVFF ANDTYLPSQM PAALKPYRDD      180

ELRNLRGDDQ QGPYOEHDRI YRYDVYNDLG EGRPILGGNS DHPYPRRGRT ERKPNASDPS      240

LESRLSLLEQ IYVPRDEKFG NLKTSDFLGY SIKAITOGIL PAVRTYVDTT PGEFOSFQDI      300

INLYEGGIKL PKVAALEELR KQFPLQLIKD LLPVGGDSLL KLPVPHIIQE NKQAWRTDEE      360

FAREVLAGVN PVHITRLTEF PPKSSLOPSK FGDHTSTITA EHIEKNLEGL TVQQALESNR      420

LYILDHHDRF MPFLIDVNNL PGNFIYATRT LFFLRGDGRL TPLAIELSEP IIQGGLTTAK      480

SKVYTPVPSG SVEGWVWELA KAYVAVNDSG WHQLVSHWLN THAVMEPFVI STNRHLSVTH      540

PVHKLLSPHY RDTMTINALA ROTLINAGGI FEMTVFPGKP ALGMSAVVYK DWKFTEQGLP      600

DDLIKRGMAV EDPSSPYKVR LLVSDYPYAA DGLAIWHAIE QYVSEYLAIY YPNDGVLQGD      660

TEVQA                                                                 665

<212> Type: PRT
<211> Length: 665
   SequenceName: SEQ ID NO: 4
   SequenceDescription: Protein sequence of inactive,
truncated LOX-1 of mutant D112
Sequence
<213> OrganismName: Hordeum vulgare cv. Neruda
<400> PreSequenceString:
atgctgctgg gagggctgat cgacaccctc acggggcga acaagagcgc ccggctcaag        60
ggcacggtgg tgctcatgcg caagaacgtg ctggacctca cgacttcgg cgccaccatc      120 atcgacggca tcggcgagtt cctcggcaag ggcgtcacct gccagcttat cagctccacc      180
gccgtcgacc aagtaatca ctaccctcct ccggccttct cctctgttta caagatatag      240
tatttctttc gtgtgggccg gcggccatgg atggatggat gtgtctggat cggctaaaga      300
agataggata gctagccctg gccggtcgtc tttacctgag catgggcata tgccatcgaa      360
aaaagagaca acagcatgca tgcatggtgc gcgcaccaga ccacgcagag caccggatgc      420
tcgagacaaa gcaacacaac aagcaaggac gacacgtcaa agcaacaca acaagcaagg      480 acggcacgtc aaaagcaaca caaacctaaa ctaaagcaca aagacgtaag agcaagcaca      540
caatcagcag gctataaaca gttgtcatca aaaacaacgc tggaagagag agagaaggaa      600
ggaagtagta gccatgaaaa attaaatcac cgggcgttgc tctttgccca acaattaatc      660
aagcaggata cgtggcatgt atagttcttg taagtaaact aagcatgtga tatgagaagg      720
```

```
tacgtggtgg tgcagacaac ggcggtcgcg ggaaggtggg cgcggaggcg gagctggagc      780
agtgggtgac gagcctgccg tcgctgacga cgggggagtc caagttcggc ctcaccttcg      840
actgggaggt ggagaagctc ggggtgccgg gcgccatcgt cgtcaacaac taccacagct      900
ccgagttcct gcttaaaacc atcaccctcc acgacgtccc cggccgcagc ggcaacctca      960
ccttcgtcgc caactcatgg atctaccccg ccgccaacta ccgatacagc cgcgtcttct     1020
tcgccaacga cgtgcgtgga ttttcctcta ctttcctctc ctttcatttt caccgccttc     1080
gtcattcatg gtcgatcatt aagtcttgcc aggacastag atgatgagct aggagtggtt     1140
accacttagc agtacgtaca ttatttattc cgtgttggta gaaaaggata tggtttggtg     1200
cagatcgaca caagettgaa tgaaagttgc accgtggcac cgtggcagcg tggtaggtga     1260
aaataactgt tgcacggatc cacccacatg attgttttca tgaataaact tttttaaggat    1320 gtgtctagcc acatctagat gcatgtcaca taattattgc ataccaasac gattaaatta     1380
agcataaaaa gaaaggaaa aaaatactca catatctcga cgtaagatca atgatatagt      1440
atttagatat gcaatattta tcttacatct aaacctttct tcattcctaa atatcagaca     1500
tttgtaagat ttcaccatgg acaacatcg aaacaaaatc agtggatctc tctatgcatt      1560
cattatgtag tctataataa aatctttaaa agatcgtata ttttgcaacg gagggagtaa     1620
aacataactt tttaatagta atgttgcacg gctccacact cgcagacgta cctgccgagc     1680
cagatgccgg cggcgctgaa gccgtaccgc gacgacgagc tccggaacct gcgtggcgac     1740
gaccagcagg gcccgtacca ggagcacgac cgcatctacc gctacgacgt ctacaacgac     1800
ctcggcgagg gccgccccat cctcggcggc aactccgacc cccttaccc gcgccgcggc      1860 cgcacggagc gcaagcccaa cgccagcgac ccgagcctgg agagccggct gtcgctgctg     1920
gagcagatct acgtgccgcg ggacgagaag ttcggccacc tcaagacgtc cgacttcctg     1980
ggctactcca tcaaggccat cacgcagggc atcctgccgg ccgtgcgcac ctacgtggac     2040 accaccccg gcgagttcga ctccttccag gacatcatca acctctatga gggcggcatc      2100
aagctgccca aggtggccgc cctggaggag ctccgtaagc agttcccgct ccagctcatc     2160
aaggacctcc tccccgtcgg cggcgactcc ctgcttaagc tccccgtgcc ccacatcatc     2220 caggageaca agcaggcgtg gaggaccgac gaggagttcg cacgggaggt gctcgccggc     2280
gtcaacccgg tcatgatcac gcgtctcacg gtgagtcagc gattatttgt tcattgtgtg     2340
tgtatggtgt ccatggtgag aaagtgcaga tcttgatttg cgttgggtcg catgcacgca     2400
tgctgcatgc atgcaggagt tcccgccaaa aagtagtctg gaccctagca agtttggtga     2460
ccacaccagc accatcacgg cggagcacat agagasgeac ctcgagggcc tcacggtgca     2520
gcaggtaatt ggtccaagcc atcgacatca actatgattt acctaggagt aattggtagc     2580
tgtagataat ttggcttcgt tgcaattaat ttgatgctgg ccgatcaagt gatcgtattg     2640
ggtttgaaat ttgcaggcgc tggaaagcaa caggctgtac atccttgatc accatgaccg     2700
gttcatgccg ttcctgatcg acgtcaacaa cctgcccggc aacttcatct acgccacgag     2760
gaccctcttc ttcctgcgcg cgacggcag gctcacgccg ctcgccatcg agctgagcga      2820
gcccatcatc cagggcggcc ttaccacggc caagagcaag gtttacacgc cggtgcccag     2880
cggctccgtc gaaggctggg tgtgggagct cgccaaggcc tacgtcgccg tcaatgactc     2940
cgggtggcac cagctcgtca gccactggta cgttctccac ggtcgatgtg attcagtcag    3000
tcgatgcaca acaactgatc gaaatatgat tgattgaaac gcgcaggctg aacactcacg     3060
cggtgatgga gccgttcgtg atctcgacga accggcacct tagcgtgacg cacccggtgc     3120
```

-continued

```
acaagctgct gagcccgcac taccgcgaca ccatgaccat caacgcgctg gcgcggcaga      3180
cgctcatcaa cgccggcggc atcttcgaga tgacggtgtt cccgggcaag ttcgcgttgg      3240
ggatgtcggc cgtggtgtac aaggactgga agttcaccga gcagggactg ccggacgatc      3300
tcatcaagag gtacgtacct ggtaaatgtt atgaatgtgt aaaacaaatt gggcgtctcg      3360
ctcactgaca ggaacgtggt aaaaaaaatg caggggcatg gcggtggagg acccgtcgag      3420
cccgtacaag gtgcggttgc tggtgtcgga ctacccgtac gcggcggacg ggctggcgat      3480
ctggcacgcc attgagcagt acgtgagcga gtacctggcc atctactacc gaacgacgg       3540
cgtgctgcag ggcgatacgg aggtgcaggc gtggtggaag gagacgcgcg aggtcgggca      3600
cggcgacctc aaggacgccc catggtggcc caagatgcaa agtgtgccgg agctggccaa      3660
ggcgtgcacc accatcatct ggatcgggtc ggcgctgcat gcggcagtca acttcgggca      3720
gtaccctac gcggggttcc tcccgaaccg gccgacggtg agccggcgcc gcatgccgga      3780
gcccggcacg gaggagtacg cggagctgga gcgcgacccg gagcgggcct tcatccacac      3840
catcacgagc cagatccaga ccatcatcgg cgtgtcgctg ctggaggtgc tgtcgaagca      3900
ctcctccgac gagctgtacc tcgggcagcg ggacacgccc gagtggacct cggacccaaa      3960
ggccctggag gtgttcaagc ggttcagcga ccggctggtg gagatcgaga gcaaggtggt      4020
gggcatgaac catgacccgg agctcaagaa ccgcaacggc ccggctaagt ttccctacat      4080
gctgctctac cccaacacct ccgaccacaa gggcgccgct gccgggctta ccgccaaggg      4140
catccccaac agcatctcca tctaa                                            4165
<212> Type: DNA
<211> Length: 4165
   SequenceName: SEQ ID NO: 5
   SequenceDescription: Barley genomic sequence of cv. Neruda
spanning the start and stop codons of the gene encoding LOX-1
Sequence
<213> OrganismName: Hordeum vulgare mutant A618
<400> PreSequenceString:
atgctgctgg gagggctgat cgacaccctc acggggggcga acaagagcgc ccggctcaag       60
ggcacggtgg tgctcatgcg caagaacgtg ctggacctca cgacttcgg cgccaccatc       120
atcgacggca tcggcgagtt cctcggcaag ggcgtcacct gccagcttat cagctccacc      180
gccgtcgacc eagtaatca ctaccctcct ccggccttct cctctgttta ceagatatag      240
tatttctttc gtgtgggccg gcggccatgg atggatggat gtgtctggat cggctaaaga      300
agataggata gctagccctg gccggtcgtc tttacctgag catgggcata tgccatcgaa      360
aaaagagaca acagcatgca tgcatggtgc gcgcaccaga ccacgcagag caccggatgc      420
tcgagacaaa gcaacacaac aagcaaggac gacacgtcaa aagcaacaca acaagcaagg      480
acggcacgtc aaaagcaaca caaacctaaa ctaaagcaca aagacgtaag agcaagcaca      540
caatcagcag gctataaaca gttgtcatca aaaacaacgc tggaagagag agagaaggaa      600
ggaagtagta gccatgaaae attaaatcac cgggcgttgc tctttgccca ecaattaatc      660
aagcaggata cgtggcatgt atagttcttg taagtaaact aagcatgtga tatgagaagg      720
tacgtggtgg tgcagacaac ggcggtcgcg ggaaggtggg cgcggaggcg gagctggagc      780
agtgggtgac gagcctgccg tcgctgacga cgggggagtc caagttcggc ctcaccttcg      840
actgggaggt ggagaagctc ggggtgccgg gcgccatcgt cgtcaacaac taccacagct      900
ccgagttcct gctaaaaacc atcccctcc acgacgtccc cggccgcagc ggcaacctca      960
ccttcgtcgc caactcatgg atctaccccg ccgccaacta ccgatacagc cgcgtcttct     1020
```

```
tcgccaacga cgtgcgtgga ttttcctcta ctttcctctc ctttcatttt caccgccttc    1080
gtcattcatg gtcgatcatt aagtcttgcc aggacaatag atgatgagct aggagtggtt    1140
accacttagc agtacgtaca ttatttattc cgtgttggta gaaaaggata tggtttggtg    1200
cagatcgaca caagattgaa tgaaagttgc accgtggcac cgtggcagcg tggtaggtga    1260
aaataactgt tgcacggatc cacccacatg attgttttca tgaataaact ttttaaggat    1320
gtgtctagcc acatctagat gcatgtcaca taattattgc ataccaseac gattaaatta    1380
agcataaaaa gaaaaggaaa aaatactcca catatctcga cgtaagatca atgatatagt    1440
atttagatat gcaatattta tcttacatct aaacctttct tcattcctaa atataagaca    1500
tttgtaagat ttcactatgg acaacatacg aaacaaaatc agtggatctc tctatgcatt    1560
cattatgtag tctataataa aatctttaaa agatcgtata ttttgcaacg gagggagtaa    1620
aacataactt tttaatagta atgttgcacg gctccacact cgcagacgta cctgccgagc    1680
cagatgccgg cggcgctgaa gccgtaccgc gacgacgagc tccggaacct gcgtggcgac    1740
gaccagcagg gcccgtacca ggagcacgac cgcatctacc gctacgacgt ctacaacgac    1800
ctcggcgagg gccgccccat cctcggcggc aactccgacc accccttaccc cgcgccgcgc    1860
cgcacggagc gcaagcccaa cgccagcgac ccgagcctgg agagccggct gtcgctgctg    1920
gagcagatct acgtgccgcg ggacgagaag ttcggccacc tcaagacgtc cgacttcctg    1980
ggctactcca tcaaggccat cacgcagggc atcctgccgg ccgtgcgcac ctacgtggac    2040
accaccccg gcgagttcga ctccttccag gacatcatca acctctatga gggcggcatc    2100
aagctgccca aggtggccgc cctggaggag ctccgtaagc agttcccgct ccagctcatc    2160
aaggacctcc tccccgtcgg cggcgactcc ctgcttaagc tccccgtgcc ccacatcatc    2220
caggagaaca agcaggcgtg gaggaccgac gaggagttcg cacgggaggt gctcgccggc    2280
gtcaacccgg tcatgatcac gcgtctcacg atgagtcagc gattatttgt tcattgtgtg    2340
tgtatggtgt ccatggtgag aaagtgcaga tcttgatttg cgttgggtcg catgcacgca    2400
tgctgcatgc atgcaggagt tcccgccaaa aagtagtctg gacccctagca agtttggtga    2460
ccacaccagc accatcacgg cggagcacat agageageac ctcgagggcc tcacggtgca    2520
gcaggtaatt ggtccaagcc atcgacatca actatgattt acctaggagt aattggtagc    2580
tgtagataat ttggcttcgt tgcaattaat ttgatgctgg ccgatcaagt gatcgtattg    2640
ggtttgaaat ttgcaggcgc tggaaagcaa caggctgtac atccttgatc accatgaccg    2700
gttcatgccg ttcctgatcg acgtcaacaa cctgcccggc aacttcatct acgccacgag    2760
gaccctcttc ttcctgcgcg cgacggcag gctcacgccg ctcgccatcg agctgagcga    2820
gcccatcatc cagggcggcc ttaccacggc caagagcaag gtttacacgc cggtgcccag    2880
cggctccgtc gaaggctggg tgtgggagct cgccaaggcc tacgtcgccg tcaatgactc    2940
cgggtggcac cagctcgtca gccactggta cgttctccac ggtcgatgtg attcagtcag    3000
tcgatgcaca caactgatc gaaatatgat tgattgaaac gcgcaggctg aacactcacg    3060
cggtgatgga gccgttcgtg atctcgacga accggcacct tagcgtgacg cacccggtgc    3120
acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcagggactg ccggacgatc    3300
tcatcaagag gtacgtacct ggtaaatgtt atgaatgtgt aaaacaaatt gggcgtctcg    3360
ctcactgaca ggaacgtggt aaaaaaaatg cagggcatg gcggtggagg accgtcgag     3420
```

```
cccgtacaag gtgcggttgc tggtgtcgga ctacccgtac gcggcggacg ggctggcgat    3480
ctggcacgcc attgagcagt acgtgagcga gtacctggcc atctactacc cgaacgacgg    3540
cgtgctgcag ggcgatccgg aggtgcaggc gtggtggaag agagacgcgcg aggtcgggca   3600 cggcgacctc aaggacgccc catggtggcc caegetgcaa agtgtgccgg agctggccaa    3660
ggcgtgcacc accatcatct ggstcgggtc ggcgctgcat gcggcagtca acttcgggca    3720 gtaccccctac gcggggttcc tcccgaaccg gccgacggtg agccggcgcc gcatgccgga   3780
gcccggcacg gaggagtacg cggagctggc gcgcgacccg gagcgggcct tcatccacac    3840
catcacgagc cegatccaga ccatcatcgg cgtgtcgctg ctggaggtgc tgtcgaagca    3900
ctcctccgac gagctgtacc tcgggcagcg ggacacgccg gagtggacct cggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt ttccctacat    4080
gctgctctac cccaacacct ccgaccacaa gggcgccgct gccgggctta ccgccaaggg    4140
catccccaac agcatctcca tctaa                                          4165

<212> Type: DNA
<211> Length: 4165
  SequenceName: SEQ ID NO: 6
  SequenceDescription: Barley genomic sequence of mutant A618,
spanning the segment corresponding to the region between
the start and stop codons of the gene encoding LOX-1 of cv. Neruda
Sequence
<213> OrganismName: Hordeum vulgare cv. Neruda
<400> PreSequenceString:
MLLGGLIDTL TGANKSARLK GTVVLMRKNV LDLNDFGATI IDGIGEFLGK GVTCQLISST    60

AVDQDNGGRG KVGAEAELEQ NVTSLPSLTT GESKFGLTFD WEVEKLGVPG AIVVNNYHSS    120

EFLLKTITLH DVPGRSGNLT FVANSWIYPA ANYRYSRVFF ANDTYLPSQM PAALKPYRDD    180

ELRNLRGDDQ QGPYQEHDRI YRYDVYNDLG EGRPILGGNS DHPYPRRGRT ERKPNASDPS    240

LESRLSLLEQ IYVPRDEKFG HLKTSDFLGY SIKAITQGIL PAVRTYVDTT PGEPDSFQDI    300

INLYEGGIKL PKVAALEELR KQFPLQLIKD LLPVGGDSLL KLPVPHIIQE NKQAWRTDEE    360

FAREVLAGVN PVMITRLTEF PPKSSLDPSK PGDHTSTITA EHIEKNLEGL TVQQALESNR    420

LYILDHHDRF MPPLIDVNNL PGNFIYATRT LFFLRGDGRL TPLAIELSEP IIQGGLTTAK    480

SKVYTPVPSG SVEGWVWELA KAYVAVNDSG WHQLVSHWLN THAVHEPFVI STNRHLSVTH    540

PVHKLLSPHY RDTMTINALA RQTLINAGGI FEMTVFPGKF ALGMSAVVYK DWKFTEQGLP    600

DDLIKRGMAV EDPSSPYKVR LLVSDYPYAA DGLAIWHAIE QYVSEYLAIY YPNDGVLQGD    660

TEVQAWWKET REVGHGDLKD APWWPIUQSV PELAKACTTI IWIGSALHAA VNFGQYPYAG    720

FLPNRPTVSR RRNPEPGTEE YAELERDPER AFIHTITSQI QTIIGVSLLE VLSKHSSDEL    780

YLGQRDTPEW TSDPKALEVF KRFSDRLVEI ESKVVGMNHD PELKNRNGPA KFPYMLLYPN    840

TSDNKGAAAG LTAKGIPNSI SI                                            862

<212> Type: PRT
<211> Length: 862
  SequenceName: SEQ ID NO: 7
  SequenceDescription: Protein sequence of full-length
LOX-1 protein of cv. Neruda
Sequence
<213> OrganismName: Hordeum vulgare mutant A618
<400> PreSequenceString:
MLLGGLIDTL TGANKSARLK GTVVLMRKNV LDLNDFGATI IDGIGEFLGK GVTCQLISST    60

AVDQDNGGRG KVGAEAELEQ WVTSLPSLTT GESKFGLTFD WEVEKLGVPG AIVVNNYHSS    120

EFLLKTITLH DVPGRSGNLT FVANSWIYPA ANYRYSRVFF ANDTYLPSQM PAALKPYRRD    180
```

-continued

```
ELRNLRGDDQ QGPYQEHDRI YRYDVYNDLG EGRPILGGNS DHPYPRRGRT ERKPNASDPS    240

LESRLSLLEQ IYVPRDEKFG NLKTSDFLGY SIKAITOGIL PAVRTYVDTT PGEFDSFQDI    300

INLYEGGIKL PKVAALEELR KQFPLQLIKD LLPVGGDSLL KLPVPHIIQE NKQAWRTDEE    360

FAREVLAGVN PVMITRLTHS QRLFVHCVCN VSMVRKCRS                          399

<212> Type: PRT
<211> Length: 399
   SequenceName: SEQ ID NO: 8
   SequenceDescription: Protein sequence of inactive,
truncated LOX-1 of mutant A618
Sequence
<213> OrganismName: Oligonucleotide
<400> PreSequenceString:
gaaagcgagg ageggaggcc aagaacaa                                       28

<212> Type: DNA
<211> Length: 28
   SequenceName: SEQ ID NO: 9
   SequenceDescription: Oligonucleotide primer used for PCR
amplification (sense primer)
Sequence
<213> OrganismName: Oligonucleotide
<400> PreSequenceString:
ttattcatcc atggttgccg atggcttaga                                     30

<212> Type: DNA
<211> Length: 30
   SequenceName SEQ ID NO: 10
   SequenceDescription: Oligonucleotide primer used for PCR
amplification (antisense primer)
Sequence
<213> OrganismName: Oligonucleotide
<400> PreSequenceString:
agggactgcc ggacgatctc a                                              21

<212> Type: DNA
<211> Length: 21
   SequenceName: SEQ ID NO: 11
   SequenceDescription: Oligonucleotide primer used for PCR
amplification (sense primer)
Sequence
<213> OrganismName: Oligonucletide
<400> PreSequenceString:
gccagctccg gcacactt                                                  18

<212> Type: DNA
<211> Length: 18
   SequenceName: SEQ ID NO: 12
   SequenceDescription: Oligonucleotide primer used for PCR
amplification (antisense primer)
Sequence
<213> OrganismName: Oligonucleotide
<400> PreSequenceString:
caaggtgcgg ttgctggtgt c                                              21

<212> Type: DNA
<211> Length: 21
   SequenceName: SEQ ID NO: 13
   SequenceDescription: Oligonucleotide primer used for PCR
amplification (sense primer)
Sequence
<213> OrganismName: Oligonucleotide
<400> PreSequenceString:
ctcgcgcgtc tccttccac                                                 19

<212> Type: DNA
<211> Length: 19
   SequenceName: SEQ ID NO: 14
   SequenceDescription: Oligonucleotide primer used for PCR
amplification (antisense primer) Sequence
<213> OrganismName: Oligonucleotide
<400> PreSequenceString:
ctcgcgcgtc tccttccat                                                 19
```

-continued

```
<212> Type: DNA
<211> Length: 19
  SequenceName: SEQ ID NO: 15
  SequenceDescription: Oligonucleotide primer used for PCR
amplification (antisense primer
Sequence
<213> OrganismName: Oligonucleotide
<400> PreSequenceString:
tacgtgccgc gggacgagaa g                                                21

<212> Type: DNA
<211> Length: 21
  SequenceName: SEQ ID NO: 16
  SequenceDescription: Oligonucleotide primer used for PCR
amplification (sense primer)
Sequence
<213> OrganismName: Oligonucleotide
<400> PreSequenceString:
tgatcatgac cgggttgacg t                                                21

<212> Type: DNA
<211> Length: 21
  SequenceName: SEQ ID NO: 17
  SequenceDescription: Oligonucleotide primer used for PCR
amplification (antisense primer)
Sequence
<213> OrganismName: Oligonucleotide
<400> PreSequenceString:
catatgctgc tgggegggc t                                                 21

<212> Type: DNA
<211> Length: 21
  SequenceName: SEQ ID NO: 18
  SequenceDescription: Oligonucleotide primer used for PCR
amplification (sense primer)
Sequence
<213> OrganismName: Oligonucleotide
<400> PreSequenceString:
gaattcttag atggagatgc tgttggg                                          27

<212> Type: DNA
<211> Length: 27
  SequenceName: SEQ ID NO: 19
  SequenceDescription: Oligonucleotide primer used for PCR
amplification (antisense primer)
Sequence
<213> OrganismName: Oligonucleotide
<400> PreSequenceString:
ctccccgtac gcggcggecg ggct                                             24

<212> Type: DNA
<211> Length: 24
  SequenceName: SEQ ID NO: 20
  SequenceDescription: Oligonucleotide primer used for PCR
amplification (sense primer)
Sequence
<213> OrganismName: Oligonucleotide
<400> PreSequenceString:
tcctgaattc acgcctgcac ctccgtatcg c                                     31

<212> Type: DNA
<211> Length: 31
  SequenceName: SEQ ID NO: 21
  SequenceDescription: Oligonucleotide primer used for PCR
amplification (antisenee primer)
```

8. DEPOSIT INFORMATION

A deposit of the Carlsberg A/S proprietary barley mutants D112 and A618—disclosed above and recited in the appended claims—has been made with the American Type Culture Collection (ATTC), 10801 University Boulevard, Manassas, Va. 20110, USA. The date of deposit for mutant D112 was Sep. 11, 2003, consisting of 2,500 kernels taken from a deposit at Carlsberg A/S since prior to the filing date of this application. The date of deposit for mutant A618 was Oct. 13, 2003, consisting of 2,500 kernels taken from a doposit at Carlsberg A/S since prior to the filing date of this application. The deposits are intended to meet all of the requirements of 37 C.F.R §1.801-1.809, including providing an indication of the viability of the samples. For mutant D112, the ATCC accession number is PTA-5487. For mutant A618, the ATCC accession number is PTA-5584. Aliquots of the deposited material can be obtained from ATCC by specifying the accession number and by accepting the standard restrictions imposed by ATCC. However, it should be understood that the availability of a deposit does not constitute a license to practice the subject invention in derogation of patent rights granted by government action.

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement with ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC. 122 and the Commissioner's rules pursuant thereto (including 37 CFR. 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Throughout this application, various publications, patents and patent applications are referred. The disclosures of these publications in their entireties are hereby incorporated by reference into this publication in order to more fully describe the state of the art to which this invention pertains. The foregoing description of the invention is exemplary for purposes of illustration and explanation. It should be understood that various modifications can be made without departing from the spirit and scope of the invention. Accordingly, the following claims are intended to be interpreted to embrace all such modifications.

REFERENCES

U.S. Patent Documents
U.S. Pat. No. 4,683,195; Mullis, K. B. et al. U.S. Pat. No. 4,800,159; Mullis, K. B. et al. U.S. Pat. No. 5,283,184; Jorgensen and Napoli
U.S. Pat. No. 5,942,661; Keller, N. P. U.S. Pat. No. 6,008,034; Häusler et al.
U.S. Pat. No. 6,150,145; Häusler, A. et al. U.S. Pat. No. 6,274,358; Holtz, R. B. et al.
U.S. Pat. No. 6,355,862 B1; Handa, A. K. and Kausch, K. D; 2003/0074693 A1; Cahoon et al.

Foreign Patent Documents
WO 02/053721 A1; December 2000; PCT Int'l Appl.; Douma, A. C. et al.

OTHER PUBLICATIONS

Alonso, J. M. et al., "Genome-wide insertional mutagenesis of *Arabidopsis thaliana*." Science 301, 653-657, 2003.
American Association of Cereal Chemists, "Approved methods of the American Association of Cereal Chemists." ISBN 0-913250-86-4 (1995).
American Society of Brewing Chemists, "Methods of analysis of the American Society of Brewing Chemists." ISBN 1-881696-01-4 (1992).
Anthon, G. E. and Barrett, D. M., "Colorimetric method for the determination of lipoxygenase activity." J. Agric. Food Chem. 49:32-37, 2001.
Ashrafi, K. et al., "Genome-wide RNAi analysis of *Caenorhabditis elegans* fat regulatory genes." Nature 421:268-272, 2003.
Auld, D. L. et al., "Rapeseed mutants with reduced levels of polyunsaturated fatty acids and increased levels of oleic acid." Crop Sci. 32:657-662, 1992.
Axelrod, B. et al., "Lipoxygenase from soybeans." Methods Enzymol. 71:442-451, 1981.
Bargmann, C. I., "High-throughput reverse genetics: RNAi screens in *Caenorhabditis elegans*."Genome Biol. 2:Reviews 1005.1-1005.3, 2001.
Bell, E. et al., "A chloroplast lipoxygenase is required for wound-induced jasmonic acid accumulation in *Arabidopsis*." Proc. Natl. Acad. Sci. USA 92:8675-8679, 1995.
Bell, E. and Mullet, J. E., "Lipoxygenase gene expression is modulated in plants by water deficit, wounding, and methyl jasmonate." Mol. Gen. Genet. 230:456-462, 1991.
Bell, E. and Mullet, J. E., "Characterization of an *Arabidopsis* lipoxygenase gene responsive to methyl jasmonate and wounding." Plant Physiol. 103:1133-1137, 1993.
Bios International, "Data." Bios Intern. 4:38-42, 2001.
Blée, E. and Joyard, J., "Envelope membranes from spinach chloroplasts are a site of metabolism of fatty acid hydroperoxides." Plant Physiol. 110:445-454, 1996.
Bohland, C. et al., "Differential induction of lipoxygenase isoforms in wheat upon treatment with rust fungus elicitor, chitin oligosaccharides, chitosan, and methyl jasmonate." Plant Physiol. 114:679-685, 1997.
Burow, G. B. et al., "A peanut seed lipoxygenase responsive to *Aspergillus* colonization." Plant Mol. Biol. 42:689-701, 2000.
Casey, R., "Lipoxygenases in the breadmaking process." In: "First European Symposium on Enzymes and Grain Processing." Angelino, S. A. G. F., van Hamer, R. J., Hartingsveldt, W., Heidekamp, F., van der Lugt, J. P., eds., pp. 188-194. TNO Nutrition and Food Research Institute, 1997. ISBN 90-75202-04-0.
Christensen, A. H. et al., "Maize polyubiquitin genes: Structure, thermal perturbation of expression and transcript splicing, and promoter activity following transfer to protoplasts by electroporation." Plant Mol. Biol. 18:675-689, 1992.
Colbert, T. et al., "High-throughput screening for induced point mutations." Plant Physiol. 126:480-484, 2001.
Cornish-Bowden, A., "Nomenclature for incompletely specified bases in nucleic acid sequences: Recommendations 1984." Nucleic Acids Res. 13:3021-3030, 1985.
Croft, K. P. C. et al., "Volatile products of the lipoxygenase pathway evolved from *Phaseolus vulgaris* (L.) leaves inoculated with *Pseudomonas syringae* pv phaseolicola." Plant Physiol. 101:13-24, 1993.
Davies, C. S. and Nielsen, N. C., "Genetic analysis of null-allele for lipoxygenase-2 in soybean." Crop Sci. 26:460-463, 1986.
Dougherty, W. G. and Parks, T. D., "Transgenes and gene suppression: Telling us something new?" Curr. Opin. Cell Biol. 7:399-405, 1995.
Drost, B. W. et al., "Role of individual compounds in beer staling." Tech. Q. MBAA 11:127-134, 1974.
Drost, B. W. et al., "Flavor stability." J. Am. Soc. Brew. Chem. 48:124-131, 1990.

European Brewery Convention, "Analytica—EBC." ISBN 3-418-00759-7 (1998).

Feussner, I. and Wasternack, C., "The lipoxygenase pathway." Annu. Rev. Plant Physiol. Plant Mol. Biol. 53:275-297, 2002.

Forster, C. et al., "Molecular analysis of a null mutant for pea (*Pisum sativum* L.) seed lipoxygenase-2." Plant Mol. Biol. 39:1209-1220, 1999.

Gardner, H. W. and Grove, M. J., "Method to produce 9(S)-hydroperoxides of linoleic and linolenic acids by maize lipoxygenase." Lipids 36:529-533, 2001.

Giaever, G. et al., "Functional profiling of the *Saccharomyces cerevisiae* genome."Nature 418:387-391, 2002.

Goenczy, P. et al., "Functional genomic analysis of cell division in *C. elegans* using RNAi of genes on chromosome III." Nature 408:331-336, 2000.

Graef, G. L. et al. "Fatty acid development in a soybean mutant with high stearic acid." J. Am. Oil Chem. Soc. 62:773-775, 1985.

Griffiths, A. et al., "Fruit-specific lipoxygenase suppression in antisense-transgenic tomatoes." Postharvest Biol. Technol. 17:163-173, 1999.

Groenqvist, A. et al., "Carbonyl compounds during beer production in beer." Proceedings of the 24th EBC Congress, Oslo, pp. 421-428, 1993.

Grosch, W. and Schwartz, J. M., "Linoleic and linolenic acid as precursors of the cucumber flavor." Lipids 6:351-352, 1971.

Hamberg, M., "Trihydroxyoctadecenoic acids in beer: Qualitative and quantitative analysis." J. Agric. Food Chem. 39:1568-1572, 1991.

Hannon, G. J., "RNA interference." Nature 418:244-251, 2002.

Hildebrand, D. F. and Hymowitz, T., "Inheritance of lipoxygenase-1 activity in soybean seeds." Crop Sci. 22:851-853, 1982.

Holtman, W. L. et al., "Differential expression of lipoxygenase isoenzymes in embryos of germinating barley." Plant Physiol. 111:569-576, 1996.

Husson, F. and Belin, J. M., "Purification of hydroperoxide lyase from green bell pepper (*Capsicum annuum* L.) fruits for the generation of C6-aldehydes in vitro." J. Agric. Food Chem. 50:1991-1995, 2002.

Institute of Brewing, "Institute of Brewing. Methods of analysis." ISBN 0-900489-10-3 (1997).

IUPAC-IUB Joint Commission on Biochemical Nomenclature, "Nomenclature and symbolism for amino acids and peptides. Recommendations 1983." Biochem. J. 219:345-373, 1984.

Isshiki, M. et al., "Nonsense-mediated decay of mutant waxy mRNA in rice." Plant Physiol. 125:1388-1395, 2001.

Jalloul, A. et al., "Lipid peroxoidation in cotton: *Xanthomonas* interactions and the role of lipoxygenases during the hypersensitive reaction." Plant J. 32:1-12, 2002.

Jamieson, A. M. and Van Gheluwe, J. E. A., "Identification of a compound responsible for cardboard flavor in beer." Proc. Am. Soc. Brew. Chem. 29:192-197, 1970.

Jende-Strid, B., "Gene-enzyme relations in the pathway of flavonoid biosynthesis in barley." Theor. Appl. Genet. 81:668-674, 1991.

Jende-Strid, B., "Genetic control of flavonoid biosynthesis in barley." Hereditas 119:187-204, 1993.

Jensen, L. G. et al., "Transgenic barley expressing a protein-engineered, thermostable (1,3-1,4)-β-glucanase during germination." Proc. Natl. Acad. Sci. USA 93, 3487-3491, 1996.

Kamath, R. S. et al., "Effectiveness of specific RNA-mediated interference through ingested double-stranded RNA in *Caenorhabdtis elegans*." Genome Biol. 2:Research0002.1-0002.10, 2000.

Kamath, R. S. et al., "Systematic functional analysis of the *Caenorhabditis elegans* genome using RNAi." Nature 421: 231-237, 2003.

Kitamura et al., "Genetic analysis of a null-allele for lipoxygenase-3 in soybean seeds." Crop Sci. 23:924-927, 1983.

Kleinhofs, A. et al., "Induction and selection of specific gene mutations in Hordeum and Pisum." Mut. Res. 51:29-35, 1978.

Kolomiets, M. V. et al., "Lipoxygenase is involved in the control of potato tuber development." Plant Cell 13:613-626, 2001.

Kuroda et al., "Characterization of factors involved in the production of 2(E)-nonenal during mashing." Biosci. Biotechnol. Biochem. 67:691-697, 2003.

Kusaba, M. et al., "Low glutelin content1: A dominant mutation that suppresses the *Glutelin* multigene family via RNA silencing in rice." Plant Cell 15:1455-1467, 2003.

Laemmli, U. K., "Cleavage of structural proteins during the assembly of the head of bacteriophage T4." Nature 227: 680-685, 1970.

León, J. et al., "Lipoxygenase H1 gene silencing reveals a specifc role in supplying fatty acid hydroperoxides for aliphatic aldehyde production." J. Biol. Chem. 277:416-423, 2002.

Lermusieau, G. et al., "Nonoxidative mechanism for development of trans-2-nonenal in beer." J. Am. Soc. Brew. Chem. 57(1):29-33, 1999.

Liégeois, C. et al., "Release of deuterated (E)-2-nonenal during beer aging from labeled precursors synthesized before boiling." J. Agric. Food Chem. 50:7634-7638, 2002.

Maquat, L. E. and Carmichael, G. G., "Quality control of mRNA function." Cell 104:173-176, 2001.

Matsui, K. et al., "Effects of overexpression of fatty acid 9-hydroperoxide lyase in tomatoes (*Lycopersicon esculentum* Mill.)." J. Agric. Food Chem. 49:5418-5424, 2001.

May, C. et al., "The N-terminal β-barrel structure of lipid body lipoxygenase mediates its binding to liposomes and lipid bodies." Eur. J. Biochem. 267:1100-1109, 2000.

McElroy, D. and Jacobsen, J., "What's brewing in barley biotechnology?" Bio/Technology 13:245-249, 1995.

Meilgaard, M. C., "Flavor chemistry of beer: Part II: Flavor and threshold of 239 aroma volatiles." Tech. Q. MBAA 12:151-167, 1975.

Melan, M. A. et al., "An *Arabidopsis* lipoxygenase gene can be induced by pathogens, abscisic acid, and methyl jasmonate." Plant Physiol. 101:441-450, 1993.

Mendell, J. T. and Dietz, H. C., "When the message goes awry: Disease-producing mutations that influence mRNA content and performance." Cell 107:411-414, 2002.

Narziss, L., "Centenary Review: Technological factors of flavour stability." J. Inst. Brew. 92:346-353, 1986.

Noël, S. and Collin, S., "Trans-2-nonenal degradation products during mashing." Eur. Brew. Conv. Proc. Congr. 25th, Brussels: 483-490, 1995.

Noordermeer, M. A. et al., "Fatty acid hydroperoxide lyase: A plant cytochrome P450 enzyme involved in wound healing and pest resistance." ChemBioChem 2:494-504, 2001.

Noordermeer, M. A. et al., "Development of a biocatalytic process for the production of C6-aldehydes from vegetable oils by soybean lipoxygenase and recombinant hydroperoxide lyase." J. Agric. Food Chem. 50:4270-4274, 2002.

Norden, A .J. et al., "Variability in oil quality among peanut genotypes in the Florida breeding program." Peanut Sci. 14:7-11, 1987.

Nyborg, M. et al., "Investigations of the protective mechanism of sulfite against beer staling and formation of adducts with trans-2-nonenal." J. Am. Soc. Brew. Chem. 57:24-28, 1999.

Ohtsu, K. et al., "Flavor stability of packaged beer in relation to the oxidation of wort." Brew. Dig. 61(6):18-23, 1986.

Olsen, O. et al., "Preferential generation of A·T→G·C transitions in the barley *Ant*18 gene." Proc. Natl. Acad. Sci. USA 90:8043-8047, 1993.

Osorio, J. et al., "Mutant sunflower with high concentration of saturated fatty acids in the oil." Crop Sci. 35:739-742, 1995.

Parinov, S. and Sundaresan, V., "Functional genomics in Arabidopsis: Large-scale insertional mutagenesis complements the genome sequencing project." Curr. Opin. Biotechnol. 11:157-161, 2000.

Phillips, D. R. and Galliard, T., "Flavour biogenesis, partial purification and properties of a fatty acid hydroperoxide cleaving enzyme from fruits of cucumber." Phytochemistry 17:355-358, 1978.

Ramezanzadeh, F. M. et al., "Prevention of oxidative rancidity in rice bran during storage." J. Agric. Food Chem. 47:2997-3000, 1999.

Rancé, I. et al., "The incompatible interaction between *Phytophthora parasitica* var. *nicotianae* race 0 and tobacco is suppressed in transgeniv plants expressing antisense lipoxygenase sequences." Proc. Natl. Acad. Sci. USA 95:6554-6559, 1998.

Rasmussen, S. K. and Hatzak, F., "Identification of two low-phytate barley (*Hordeum vulgare* L.) grain mutants by TLC and genetic analysis." Hereditas 129:107-112, 1998.

Rogers, K. R. et al., "Lipid peroxidation is a consequence of elicitor activity." Plant Physiol. 86:547-553, 1988.

Rouster, J. et al., "Identification of a methyl jasmonate-responsive region in the promoter of a lipoxygenase 1 gene expressed in barley grain." Plant J. 11:513-523, 1997.

Royo, J. et al., "Antisense-mediated depletion of a potato lipoxygenase reduces wound induction of proteinase inhibitors and increases weight gain of insect pests." Proc. Natl. Acad. Sci. USA 96:1146-1151, 1999.

Rustérucci, C. et al., "Involvement of lipoxygenase-dependent production of fatty acid hydroperoxides in the development of the hypersensitive cell death induced by cryptogein on tobacco leaves." J. Biol. Chem. 274:36446-36455, 1999.

Sambrook, J. et al., "Molecular Cloning: A Laboratory Manual, 2nd Ed.", Cold Spring Harbor Laboratory Press, Cold Spring Harbor, N.Y., 1989. ISBN 0-87969-309-6.

Sambrook, J. and Russell, D. W., "Molecular Cloning. A Laboratory Manual, 3rd Ed.", Cold Spring Harbor Laboratory Press, Cold Spring Harbor, N.Y., 2001. ISBN 0-87969-577-3.

Saravitz, D. M. and Siedow, J. N., "The differential expression of wound-inducible lipoxygenase genes in soybean leaves." Plant Physiol. 110:287-299, 1996.

Schmitt, N. F. and Van Mechelen, J. R., "Expression of lipoxygenase isoenzymes in developing barley grains." Plant Sci. 128:141-150, 1997.

Soldatov, K. I., "Chemical mutagenesis in sunflower breeding." In: "Proceedings of the VIIth International Sunflower Conference, 27 Jun.-3 Jul. 1976, Krasnodar, USSR, Vol. 1", pp 352-357. International Sunflower Association, Toowoomba, Australia, 1976.

Srivastava, S. et al., "Structural and kinetic determinants of aldehyde reduction by aldose reductase." Biochemistry 38:42-54, 1999.

Start, W. G. et al., "Two soybean seed lipoxygenase nulls accumulate reduced levels of lipoxygenase transcripts." Plant Mol. Biol. 7:11-23, 1986.

Tatulian, S. A. et al., "Uncovering a calcium-regulated membrane-binding mechanism for soybean lipoxygenase-1." Biochemistry 37:15481-15490, 1998.

Tijet, N. et al., "Biogenesis of volatile aldehydes from fatty acid hydroperoxides: Molecular cloning of a hydroperoxide lyase (CYP74C) with specificity for both the 9- and 13-hydroperoxides of linoleic and linolenic acids." Arch. Biochem. Biophys. 386:281-289, 2001.

Tingay, S. et al., "*Agrobacterium tumefaciens*-mediated barley transformation." Plant J. 11:1369-1376, 1997.

Towbin, H. et al., "Electrophoretic transfer of proteins from polyacrylamide gels to nitrocellulose sheets: Procedure and some applications." Proc. Natl. Acad. Sci. USA 76:4350-4354, 1979.

Turner, J. G. et al., "The jasmonate signal pathway." Plant Cell 14:S153-S164, 2002.

Vancanneyt, G. et al., "Hydroperoxide lyase depletion in transgenic potato plants leads to an increase in aphid performance." Proc. Natl. Acad. Sci. USA 98:8139-8144, 2001.

van Mechelen, J. R. et al., "Primary structure of a lipoxygenase from barley grain as deduced from its cDNA sequence." Bioche. Biophys. Acta 1254:221-225, 1995.

van Mechelen, J. R. et al., "Molecular characterization of two lipoxygenases from barley." Plant Mol. Biol. 39:1283-1298, 1999.

von Wettstein, D. et al., "Biochemical mutant in barley renders chemical stabilization of beer superfluous." Carlsberg Res. Commun. 42:341-351, 1977.

von Wettstein, D. et al., "Proanthocyanidin-free barley for brewing: Progress in breeding for high yield and research tool in polyphenol chemistry." Tech. Q. MBAA 22:41-52, 1985.

Wan, Y. and Lemaux, P. G., "Generation of large numbers of independently transformed fertile barley plants." Plant Physiol. 104:37-48, 1994.

Wang, J. et al., "Alternatively spliced TCR mRNA induced by disruption of reading frame." Science 297:108-110, 2002.

Wang, M.-B. et al., "*Agrobacterium tumefaciens*-mediated transformation of an elite Australian barley cultivar with virus resistance and reporter genes." Aust. J. Plant Physiol. 28:149-156, 2001.

Wang, W. H. et al., "Molecular basis of a null mutation in soybean lipoxygenase 2: Substitution of glutamine for an iron-ligand histidine." Proc. Natl. Acad. Sci. USA 91:5828-5832, 1994.

Wang, W.-H. et al., "Two single-base substitutions involved in altering in a paried-box of AAATAC in the promoter region of soybean lipoxygenase L-3 gene impair the promoter function in tobacco cells." Plant Sci. 109:67-73, 1995.

Weber, H. et al., "Divinyl ether fatty acid synthesis in late blight-diseased potato leaves." Plant Cell 11:485-493, 1999.

Wesley, S. V. et al., "Construct design for efficient, effective and high-throughput gene silencing in plants." Plant J. 27:581-590, 2001.

White, J. et al., "A cassette containing the bar gene of *Streptomyces hygroscopicus*: A selectable marker for plant transformation." Nucleic Acids Res. 18:1062, 1990.

Zhang, Y. et al., "Expression of antisense SnRK1 protein kinase sequence causes abnormal pollen development and male sterility in transgenic barley." Plant J. 28:431-441, 2001.

What is claimed is:

1. A barley plant or a portion of said plant, comprising mutated LOX-1 protein lacking all or at least a portion of amino acids 520 to 862 of wild type barley LOX-1 (SEQ ID NO: 3 or 7), wherein said plant exhibits null LOX-1 activity.

2. A barley plant or portion of said plant comprising mutated LOX-1 protein truncated at or between amino acids 378 and 665 of wild-type barley LOX-1 (SEQ ID NO: 3 or 7), wherein said plant exhibits null LOX-1 activity.

3. The barley plant or portion according to claim 2, wherein said mutated LOX-1 protein consists essentially of amino acids 1-378 of wild-type barley LOX-1 (SEQ ID NO: 3 or 7).

4. The barley plant or portion according to claim 3, wherein said mutated LOX-1 protein has the amino acid sequence of SEQ ID NO: 4 or 8.

5. The barley plant or portion according to claim 2, wherein said mutated LOX-1 protein is encoded by a gene that comprises a premature stop codon at or between nucleotides 2311 and 3574 of wild-type genomic barley lox-1 (SEQ ID NO: 1 or 5).

6. The barley plant or portion according to claim 5, wherein said mutated LOX-1 protein is encoded by a gene that comprises a stop codon at nucleotides 3572-3574 of wild-type genomic barley lox-1 (SEQ ID NO: 1 or 5).

7. The barley plant or portion according to claim 5, wherein said mutated LOX-1 protein is encoded by the nucleic acid sequence of SEQ ID NO: 2 or 6.

8. The barley plant or portion according to claim 1, wherein said plant has ATCC accession No. PTA-5847 or PTA-5584.

9. The barley plant or portion according to claim 1, wherein said portion comprises a kernel.

10. The barley plant or portion according to claim 1, wherein said portion comprises an embryo.

11. The barley plant or portion according to claim 1, wherein said LOX-1 activity is determined in homogenized embryo tissue of M3 or M4 plant kernels.

12. A malt composition comprising malted kernels of the plant of claim 1.

13. A malt composition comprising malted kernels of the plant of claim 6.

* * * * *

SEQUENCE LISTING

<160> NUMBER OF SEQ ID NOS: 21

<210> SEQ ID NO 1
<211> LENGTH: 4165
<212> TYPE: DNA
<213> ORGANISM: Hordeum vulgare cv. Barke

<400> SEQUENCE: 1

| | | | | | |
|---|---|---|---|---|---|
| atgctgctgg | gagggctgat | cgacaccctc | acggggcga | acaagagcgc | ccggctcaag | 60 |
| ggcacggtgg | tgctcatgcg | caagaacgtg | ctggacctca | cgacttcgg | cgccaccatc | 120 |
| atcgacggca | tcggcgagtt | cctcggcaag | ggcgtcacct | gccagcttat | cagctccacc | 180 |
| gccgtcgacc | aaggtaatca | ctaccctcct | ccggccttct | cctctgttta | caagatatag | 240 |
| tatttctttc | gtgtgggccg | gcggccatgg | atggatggat | gtgtctggat | cggctaaaga | 300 |
| agataggata | gctagccctg | gccggtcgtc | tttacctgag | catgggcata | tgccatcgaa | 360 |
| aaaagagaca | acagcatgca | tgcatggtgc | gcgcaccaga | ccacgcagag | caccggatgc | 420 |
| tcgagacaaa | gcaacacaac | aagcaaggac | gacacgtcaa | aagcaacaca | acaagcaagg | 480 |
| acggcacgtc | aaaagcaaca | caaacctaaa | ctaaagcaca | aagacgtaag | agcaagcaca | 540 |
| caatcagcag | gctataaaca | gttgtcatca | aaaacaacgc | tggaagagag | agagaaggaa | 600 |
| ggaagtagta | gccatgaaaa | attaaatcac | cgggcgttgc | tctttgccca | acaattaatc | 660 |
| aagcaggata | cgtggcatgt | atagttcttg | taagtaaact | aagcatgtga | tatgagaagg | 720 |
| tacgtggtgg | tgcagacaac | ggcggtcgcg | ggaaggtggg | cgcggaggcg | gagctggagc | 780 |
| agtgggtgac | gagcctgccg | tcgctgacga | cgggggagtc | caagttcggc | ctcaccttcg | 840 |
| actgggaggt | ggagaagctc | ggggtgccgg | gcgccatcgt | cgtcaacaac | taccacagct | 900 |
| ccgagttcct | gcttaaaacc | atcaccctcc | acgacgtccc | cggccgcagc | ggcaacctca | 960 |
| ccttcgtcgc | caactcatgg | atctaccccg | ccgccaacta | ccgatacagc | cgcgtcttct | 1020 |
| tcgccaacga | cgtgcgtgga | ttttcctcta | ctttcctctc | ctttcatttt | caccgccttc | 1080 |
| gtcattcatg | gtcgatcatt | aagtcttgcc | aggacaatag | atgatgagct | aggagtggtt | 1140 |
| accacttagc | agtacgtaca | ttatttattc | cgtgttggta | gaaaaggata | tggtttggtg | 1200 |
| cagatcgaca | caagattgaa | tgaaagttgc | accgtggcac | cgtggcagcg | tggtaggtga | 1260 |
| aaataactgt | tgcacggatc | cacccacatg | attgttttca | tgaataaact | ttttaaggat | 1320 |
| gtgtctagcc | acatctagat | gcatgtcaca | taattattgc | ataccaaaac | gattaaatta | 1380 |
| agcataaaaa | gaaaggaaa | aaaatactca | catatctcga | cgtaagatca | atgatatagt | 1440 |
| atttagatat | gcaatattta | tcttacatct | aaacctttct | tcattcctaa | atataagaca | 1500 |
| tttgtaagat | ttcactatgg | acaacatacg | aaacaaaatc | agtggatctc | tctatgcatt | 1560 |
| cattatgtag | tctataataa | aatctttaaa | agatcgtata | ttttgcaacg | gagggagtaa | 1620 |
| aacataactt | tttaatagta | atgttgcacg | gctccacact | cgcagacgta | cctgccgagc | 1680 |
| cagatgccgg | cggcgctgaa | gccgtaccgc | gacgacgagc | tccggaacct | gcgtggcgac | 1740 |
| gaccagcagg | gcccgtacca | ggagcacgac | cgcatctacc | gctacgacgt | ctacaacgac | 1800 |
| ctcggcgagg | gccgccccat | cctcggcggc | aactccgacc | cccttaccc | cgccgcggc | 1860 |
| cgcacggagc | gcaagcccaa | gccagcgac | ccgagcctgg | agagccggct | gtcgctgctg | 1920 |
| gagcagatct | acgtgccgcg | ggacgagaag | ttcggccacc | tcaagacgtc | cgacttcctg | 1980 |
| ggctactcca | tcaaggccat | cacgcagggc | atcctgccgg | ccgtgcgcac | ctacgtggac | 2040 |

```
accaccccccg gcgagttcga ctccttccag gacatcatca acctctatga gggcggcatc    2100
aagctgccca aggtggccgc cctggaggag ctccgtaagc agttcccgct ccagctcatc    2160
aaggacctcc tccccgtcgg cggcgactcc ctgcttaagc tccccgtgcc ccacatcatc    2220
caggagaaca agcaggcgtg gaggaccgac gaggagttcg cacgggaggt gctcgccggc    2280
gtcaacccgg tcatgatcac gcgtctcacg gtgagtcagc gattatttgt tcattgtgtg    2340
tgtatggtgt ccatggtgag aaagtgcaga tcttgatttg cgttgggtcg catgcacgca    2400
tgctgcatgc atgcaggagt tcccgccaaa aagtagtctg gacctagca agtttggtga     2460 ccacaccagc accatcacgg cggagcacat agagaagaac ctcgagggcc tcacggtgca    2520
gcaggtaatt ggtccaagcc atcgacatca actatgattt acctaggagt aattggtagc    2580
tgtagataat ttggcttcgt tgcaattaat ttgatgctgg ccgatcaagt gatcgtattg    2640
ggtttgaaat ttgcaggcgc tggaaagcaa caggctgtac atccttgatc accatgaccg    2700
gttcatgccg ttcctgatcg acgtcaacaa cctgcccggc aacttcatct acgccacgag    2760
gaccctcttc ttcctgcgcg cgacggcag gctcacgccg ctcgccatcg agctgagcga     2820
gcccatcatc cagggcggcc ttaccacggc caagagcaag gtttacacgc cggtgcccag    2880
cggctccgtc gaaggctggg tgtgggagct cgccaaggcc tacgtcgccg tcaatgactc    2940
cgggtggcac cagctcgtca gccactggta cgttctccac ggtcgatgtg attcagtcag    3000
tcgatgcaca acaactgatc gaaatatgat tgattgaaac gcgcaggctg aacactcacg    3060
cggtgatgga gccgttcgtg atctcgacga accggcacct tagcgtgacg caccccggtgc   3120 acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcagggactg ccggacgatc    3300
tcatcaagag gtacgtacct ggtaaatgtt atgaatgtgt aaaacaaatt gggcgtctcg    3360
ctcactgaca ggaacgtggt aaaaaaaatg caggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc gaacgacgg     3540 cgtgctgcag ggcgatacgg aggtgcaggc gtggtggaag gagacgcgcg aggtcgggca    3600
cggcgacctc aaggacgccc catggtggcc caagatgcaa agtgtgccgg agctggccaa    3660
ggcgtgcacc accatcatct ggatcgggtc ggcgctgcat gcggcagtca acttcgggca    3720 gtaccccctac gcggggttcc tcccgaaccg gccgacggtg agccggcgcc gcatgccgga   3780
gcccggcacg gaggagtacg cggagctgga gcgcgacccg gagcgggcct tcatccacac    3840
catcacgagc cagatccaga ccatcatcgg cgtgtcgctg ctggaggtgc tgtcgaagca    3900
ctcctccgac gagctgtacc tcgggcagcg ggacacgccg gagtggacct cggacccaaa    3960
ggccctggag gtgttcaagc cggttcagcga ccggctggtg gagatcgaga gcaaggtggt   4020
gggcatgaac catgacccgg agctcaagaa ccgcaacggc ccggctaagt ttcccctacat   4080 gctgctctac cccaacacct ccgaccacaa gggcgccgct gccgggctta ccgccaaggg    4140
catccccaac agcatctcca tctaa                                          4165
```

<210> SEQ ID NO 2
<211> LENGTH: 4165
<212> TYPE: DNA
<213> ORGANISM: Hordeum vulgare mutant D112

-continued

```
<400> SEQUENCE: 2
atgctgctgg gagggctgat cgacaccctc acggggcga acaagagcgc ccggctcaag      60
ggcacggtgg tgctcatgcg caagaacgtg ctggacctca cgacttcgg cgccaccatc     120 atcgacggca tcggcgagtt cctcggcaag ggcgtcacct gccagcttat cagctccacc    180
gccgtcgacc aagtaatca ctaccctcct ccggccttct cctctgttta caagatatag     240
tatttctttc gtgtgggccg gcggccatgg atggatggag tgtctggat cggctaaaga    300 agataggata gctagccctg gccggtcgtc tttacctgag catgggcata tgccatcgaa    360
aaaagagaca acagcatgca tgcatggtgc gcgcaccaga ccacgcagag caccggatgc    420
tcgagacaaa gcaacacaac aagcaaggac gacacgtcaa agcaacaca acaagcaagg    480 acggcacgtc aaaagcaaca caaacctaaa ctaaagcaca aagacgtaag agcaagcaca    540
caatcagcag gctataaaca gttgtcatca aaaacaacgc tggaagagag agagaaggaa    600
ggaagtagta gccatgaaaa attaaatcac cgggcgttgc tctttgccca acaattaatc    660
aagcaggata cgtggcatgt atagttcttg taagtaaact aagcatgtga tatgagaagg    720
tacgtggtgg tgcagacaac ggcggtcgcg ggaaggtggg cgcggaggcg gagctggagc    780
agtgggtgac gagcctgccg tcgctgacga cgggggagtc caagttcggc ctcaccttcg    840
actgggaggt ggagaagctc ggggtgccgg gcgccatcgt cgtcaacaac taccacagct    900
ccgagttcct gcttaaaacc atcaccctcc acgacgtccc cggccgcagc ggcaacctca    960
ccttcgtcgc caactcatgg atctacccg ccgccaacta ccgatacagc cgcgtcttct   1020
tcgccaacga cgtgcgtgga ttttcctcta ctttcctctc ctttcatttt caccgccttc   1080
gtcattcatg gtcgatcatt aagtcttgcc aggacaatag atgatgagct aggagtggtt   1140
accacttagc agtacgtaca ttatttattc cgtgttggta gaaaaggata tggtttggtg   1200
cagatcgaca caagattgaa tgaaagttgc accgtggcac cgtggcagcg tggtaggtga   1260
aaataactgt tgcacggatc cacccacatg attgttttca tgaataaact ttttaaggat   1320
gtgtctagcc acatctagat gcatgtcaca taattattgc ataccaaaac gattaaatta   1380
agcataaaaa gaaaaggaaa aaaatactca catatctcga cgtaagatca atgatatagt   1440
atttagatat gcaatattta tcttacatct aaacctttct tcattcctaa atataagaca   1500
tttgtaagat ttcactatgg acaacatacg aaacaaaatc agtggatctc tctatgcatt   1560
cattatgtag tctataataa aatctttaaa agatcgtata ttttgcaacg gagggagtaa   1620
aacataactt tttaatagta atgttgcacg gctccacact cgcagacgta cctgccgagc   1680
cagatgccgg cggcgctgaa gccgtaccgc gacgacgagc tccggaacct gcgtggcgac   1740
gaccagcagg gcccgtacca ggagcacgac cgcatctacc gctacgacgt ctacaacgac   1800
ctcggcgagg gccgccccat cctcggcggc aactccgacc acccttaccc gcgccgcggc   1860
cgcacggagc gcaagcccaa cgccagcgac ccgagcctgg agagccggct gtcgctgctg   1920
gagcagatct acgtgccgcg ggacgagaag ttcggccacc tcaagacgtc cgacttcctg   1980
ggctactcca tcaaggccat cacgcagggc atcctgccgg ccgtgcgcac ctacgtggac   2040 accaccccg gcgagttcga ctccttccag gacatcatca acctctatga gggcggcatc   2100
aagctgccca aggtggccgc cctggaggag ctccgtaagc agttcccgct ccagctcatc   2160
aaggacctcc tccccgtcgg cggcgactcc ctgcttaagc tccccgtgcc ccacatcatc   2220
caggagaaca gcaggcgtg gaggaccgac gaggagttcg cacgggaggt gctcgccggc   2280
gtcaacccgg tcatgatcac gcgtctcacg gtgagtcagc gattatttgt tcattgtgtg   2340
```

```
tgtatggtgt ccatggtgag aaagtgcaga tcttgatttg cgttgggtcg catgcacgca    2400
tgctgcatgc atgcaggagt tcccgccaaa aagtagtctg gaccctagca agtttggtga    2460
ccacaccagc accatcacgg cggagcacat agagaagaac ctcgagggcc tcacggtgca    2520
gcaggtaatt ggtccaagcc atcgacatca actatgattt acctaggagt aattggtagc    2580
tgtagataat ttggcttcgt tgcaattaat ttgatgctgg ccgatcaagt gatcgtattg    2640
ggtttgaaat ttgcaggcgc tggaaagcaa caggctgtac atccttgatc accatgaccg    2700
gttcatgccg ttcctgatcg acgtcaacaa cctgcccggc aacttcatct acgccacgag    2760
gaccctcttc ttcctgcgcg cgacggcag gctcacgccg ctcgccatcg agctgagcga    2820
gcccatcatc cagggcggcc ttaccacggc aagagcaag gtttacacgc cggtgcccag    2880
cggctccgtc gaaggctggg tgtgggagct cgccaaggcc tacgtcgccg tcaatgactc    2940
cgggtggcac cagctcgtca gccactggta cgttctccac ggtcgatgtg attcagtcag    3000
tcgatgcaca caactgatc gaaatatgat tgattgaaac gcgcaggctg aacactcacg    3060
cggtgatgga gccgttcgtg atctcgacga accggcacct tagcgtgacg cacccggtgc    3120
acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcaggactg ccggacgatc    3300
tcatcaagag gtacgtacct ggtaaatgtt atgaatgtgt aaaacaaatt gggcgtctcg    3360
ctcactgaca ggaacgtggt aaaaaaatg caggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc gaacgacgg    3540
cgtgctgcag ggcgatacgg aggtgcaggc gtgatggaag gagacgcgcg aggtcgggca    3600
cggcgacctc aaggacgccc catggtggcc caagatgcaa agtgtgccgg agctggccaa    3660
ggcgtgcacc accatcatct ggatcgggtc ggcgctgcat gcggcagtca cttcgggca    3720
gtaccctac gcggggttcc tcccgaaccg gccgacggtg agccggcgcc gcatgccgga    3780
gcccggcacg gaggagtacg cggagctgga gcgcgacccg gagcgggcct tcatccacac    3840
catcacgagc cagatccaga ccatcatcgg cgtgtcgctg ctggaggtgc tgtcgaagca    3900
ctcctccgac gagctgtacc tcgggcagcg ggacacgccg gagtggacct cggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt tccctacat    4080
gctgctctac cccaacacct ccgaccacaa gggcgccgct gccgggctta ccgccaaggg    4140
catccccaac agcatctcca tctaa                                          4165
```

<210> SEQ ID NO 3
<211> LENGTH: 862
<212> TYPE: PRT
<213> ORGANISM: Hordeum vulgare cv. Barke

<400> SEQUENCE: 3

```
Met Leu Leu Gly Gly Leu Ile Asp Thr Leu Thr Gly Ala Asn Lys Ser
1               5                   10                  15

Ala Arg Leu Lys Gly Thr Val Val Leu Met Arg Lys Asn Val Leu Asp
            20                  25                  30

Leu Asn Asp Phe Gly Ala Thr Ile Ile Asp Gly Ile Gly Glu Phe Leu
        35                  40                  45
```

-continued

```
Gly Lys Gly Val Thr Cys Gln Leu Ile Ser Ser Thr Ala Val Asp Gln
         50                  55                  60
Asp Asn Gly Gly Arg Gly Lys Val Gly Ala Glu Ala Glu Leu Glu Gln
 65                  70                  75                  80
Trp Val Thr Ser Leu Pro Ser Leu Thr Thr Gly Glu Ser Lys Phe Gly
                     85                  90                  95
Leu Thr Phe Asp Trp Glu Val Glu Lys Leu Gly Val Pro Gly Ala Ile
                100                 105                 110
Val Val Asn Asn Tyr His Ser Ser Glu Phe Leu Leu Lys Thr Ile Thr
            115                 120                 125
Leu His Asp Val Pro Gly Arg Ser Gly Asn Leu Thr Phe Val Ala Asn
130                 135                 140
Ser Trp Ile Tyr Pro Ala Ala Asn Tyr Arg Tyr Ser Arg Val Phe Phe
145                 150                 155                 160
Ala Asn Asp Thr Tyr Leu Pro Ser Gln Met Pro Ala Ala Leu Lys Pro
                165                 170                 175
Tyr Arg Asp Asp Glu Leu Arg Asn Leu Arg Gly Asp Asp Gln Gln Gly
                180                 185                 190
Pro Tyr Gln Glu His Asp Arg Ile Tyr Arg Tyr Asp Val Tyr Asn Asp
            195                 200                 205
Leu Gly Glu Gly Arg Pro Ile Leu Gly Gly Asn Ser Asp His Pro Tyr
210                 215                 220
Pro Arg Arg Gly Arg Thr Glu Arg Lys Pro Asn Ala Ser Asp Pro Ser
225                 230                 235                 240
Leu Glu Ser Arg Leu Ser Leu Leu Glu Gln Ile Tyr Val Pro Arg Asp
                245                 250                 255
Glu Lys Phe Gly His Leu Lys Thr Ser Asp Phe Leu Gly Tyr Ser Ile
                260                 265                 270
Lys Ala Ile Thr Gln Gly Ile Leu Pro Ala Val Arg Thr Tyr Val Asp
            275                 280                 285
Thr Thr Pro Gly Glu Phe Asp Ser Phe Gln Asp Ile Ile Asn Leu Tyr
290                 295                 300
Glu Gly Gly Ile Lys Leu Pro Lys Val Ala Ala Leu Glu Glu Leu Arg
305                 310                 315                 320
Lys Gln Phe Pro Leu Gln Leu Ile Lys Asp Leu Leu Pro Val Gly Gly
                325                 330                 335
Asp Ser Leu Leu Lys Leu Pro Val Pro His Ile Ile Gln Glu Asn Lys
            340                 345                 350
Gln Ala Trp Arg Thr Asp Glu Glu Phe Ala Arg Glu Val Leu Ala Gly
            355                 360                 365
Val Asn Pro Val Met Ile Thr Arg Leu Thr Glu Phe Pro Pro Lys Ser
370                 375                 380
Ser Leu Asp Pro Ser Lys Phe Gly Asp His Thr Ser Thr Ile Thr Ala
385                 390                 395                 400
Glu His Ile Glu Lys Asn Leu Glu Gly Leu Thr Val Gln Gln Ala Leu
                405                 410                 415
Glu Ser Asn Arg Leu Tyr Ile Leu Asp His His Asp Arg Phe Met Pro
                420                 425                 430
Phe Leu Ile Asp Val Asn Asn Leu Pro Gly Asn Phe Ile Tyr Ala Thr
            435                 440                 445
Arg Thr Leu Phe Phe Leu Arg Gly Asp Gly Arg Leu Thr Pro Leu Ala
450                 455                 460
```

Ile Glu Leu Ser Glu Pro Ile Gln Gly Gly Leu Thr Thr Ala Lys
465                 470                 475                 480

Ser Lys Val Tyr Thr Pro Val Pro Ser Gly Ser Val Glu Gly Trp Val
            485                 490                 495

Trp Glu Leu Ala Lys Ala Tyr Val Ala Val Asn Asp Ser Gly Trp His
            500                 505                 510

Gln Leu Val Ser His Trp Leu Asn Thr His Ala Val Met Glu Pro Phe
            515                 520                 525

Val Ile Ser Thr Asn Arg His Leu Ser Val Thr His Pro Val His Lys
530                 535                 540

Leu Leu Ser Pro His Tyr Arg Asp Thr Met Thr Ile Asn Ala Leu Ala
545                 550                 555                 560

Arg Gln Thr Leu Ile Asn Ala Gly Gly Ile Phe Glu Met Thr Val Phe
                565                 570                 575

Pro Gly Lys Phe Ala Leu Gly Met Ser Ala Val Val Tyr Lys Asp Trp
            580                 585                 590

Lys Phe Thr Glu Gln Gly Leu Pro Asp Asp Leu Ile Lys Arg Gly Met
            595                 600                 605

Ala Val Glu Asp Pro Ser Pro Tyr Lys Val Arg Leu Leu Val Ser
610                 615                 620

Asp Tyr Pro Tyr Ala Ala Asp Gly Leu Ala Ile Trp His Ala Ile Glu
625                 630                 635                 640

Gln Tyr Val Ser Glu Tyr Leu Ala Ile Tyr Tyr Pro Asn Asp Gly Val
                645                 650                 655

Leu Gln Gly Asp Thr Glu Val Gln Ala Trp Trp Lys Glu Thr Arg Glu
                660                 665                 670

Val Gly His Gly Asp Leu Lys Asp Ala Pro Trp Trp Pro Lys Met Gln
            675                 680                 685

Ser Val Pro Glu Leu Ala Lys Ala Cys Thr Thr Ile Ile Trp Ile Gly
            690                 695                 700

Ser Ala Leu His Ala Ala Val Asn Phe Gly Gln Tyr Pro Tyr Ala Gly
705                 710                 715                 720

Phe Leu Pro Asn Arg Pro Thr Val Ser Arg Arg Met Pro Glu Pro
                725                 730                 735

Gly Thr Glu Glu Tyr Ala Glu Leu Glu Arg Asp Pro Gly Arg Ala Phe
            740                 745                 750

Ile His Thr Ile Thr Ser Gln Ile Gln Thr Ile Ile Gly Val Ser Leu
            755                 760                 765

Leu Glu Val Leu Ser Lys His Ser Ser Asp Glu Leu Tyr Leu Gly Gln
            770                 775                 780

Arg Asp Thr Pro Glu Trp Thr Ser Asp Pro Lys Ala Leu Glu Val Phe
785                 790                 795                 800

Lys Arg Phe Ser Asp Arg Leu Val Glu Ile Glu Ser Lys Val Val Gly
                805                 810                 815

Met Asn His Asp Pro Glu Leu Lys Asn Arg Asn Gly Pro Ala Lys Phe
            820                 825                 830

Pro Tyr Met Leu Leu Tyr Pro Asn Thr Ser Asp His Lys Gly Ala Ala
                835                 840                 845

Ala Gly Leu Thr Ala Lys Gly Ile Pro Asn Ser Ile Ser Ile
850                 855                 860

<210> SEQ ID NO 4
<211> LENGTH: 665
<212> TYPE: PRT

<213> ORGANISM: Hordeum vulgare mutant D112

<400> SEQUENCE: 4

```
Met Leu Leu Gly Gly Leu Ile Asp Thr Leu Thr Gly Ala Asn Lys Ser
1               5                   10                  15

Ala Arg Leu Lys Gly Thr Val Val Leu Met Arg Lys Asn Val Leu Asp
                20                  25                  30

Leu Asn Asp Phe Gly Ala Thr Ile Ile Asp Gly Ile Gly Glu Phe Leu
            35                  40                  45

Gly Lys Gly Val Thr Cys Gln Leu Ile Ser Ser Thr Ala Val Asp Gln
        50                  55                  60

Asp Asn Gly Gly Arg Gly Lys Val Gly Ala Glu Ala Glu Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
            100                 105                 110

Val Val Asn Asn Tyr His Ser Ser Glu Phe Leu Leu Lys Thr Ile Thr
        115                 120                 125

Leu His Asp Val Pro Gly Arg Ser Gly Asn Leu Thr Phe Val Ala Asn
130                 135                 140

Ser Trp Ile Tyr Pro Ala Ala Asn Tyr Arg Tyr Ser Arg Val Phe Phe
145                 150                 155                 160

Ala Asn Asp Thr Tyr Leu Pro Ser Gln Met Pro Ala Ala Leu Lys Pro
                165                 170                 175

Tyr Arg Asp Asp Glu Leu Arg Asn Leu Arg Gly Asp Asp Gln Gln Gly
            180                 185                 190

Pro Tyr Gln Glu His Asp Arg Ile Tyr Arg Tyr Asp Val Tyr Asn Asp
        195                 200                 205

Leu Gly Glu Gly Arg Pro Ile Leu Gly Gly Asn Ser Asp His Pro Tyr
210                 215                 220

Pro Arg Arg Gly Arg Thr Glu Arg Lys Pro Asn Ala Ser Asp Pro Ser
225                 230                 235                 240

Leu Glu Ser Arg Leu Ser Leu Glu Gln Ile Tyr Val Pro Arg Asp
                245                 250                 255

Glu Lys Phe Gly His Leu Lys Thr Ser Asp Phe Leu Gly Tyr Ser Ile
            260                 265                 270

Lys Ala Ile Thr Gln Gly Ile Leu Pro Ala Val Arg Thr Tyr Val Asp
        275                 280                 285

Thr Thr Pro Gly Glu Phe Asp Ser Phe Gln Asp Ile Ile Asn Leu Tyr
290                 295                 300

Glu Gly Gly Ile Lys Leu Pro Lys Val Ala Ala Leu Glu Glu Leu Arg
305                 310                 315                 320

Lys Gln Phe Pro Leu Gln Leu Ile Lys Asp Leu Leu Pro Val Gly Gly
                325                 330                 335

Asp Ser Leu Leu Lys Leu Pro Val Pro His Ile Ile Gln Glu Asn Lys
            340                 345                 350

Gln Ala Trp Arg Thr Asp Glu Glu Phe Ala Arg Glu Val Leu Ala Gly
        355                 360                 365

Val Asn Pro Val Met Ile Thr Arg Leu Thr Glu Phe Pro Pro Lys Ser
370                 375                 380

Ser Leu Asp Pro Ser Lys Phe Gly Asp His Thr Ser Thr Ile Thr Ala
385                 390                 395                 400
```

```
Glu His Ile Glu Lys Asn Leu Glu Gly Leu Thr Val Gln Gln Ala Leu
                405                 410                 415

Glu Ser Asn Arg Leu Tyr Ile Leu Asp His His Asp Arg Phe Met Pro
            420                 425                 430

Phe Leu Ile Asp Val Asn Asn Leu Pro Gly Asn Phe Ile Tyr Ala Thr
                435                 440                 445

Arg Thr Leu Phe Phe Leu Arg Gly Asp Gly Arg Leu Thr Pro Leu Ala
    450                 455                 460

Ile Glu Leu Ser Glu Pro Ile Ile Gln Gly Gly Leu Thr Thr Ala Lys
465                 470                 475                 480

Ser Lys Val Tyr Thr Pro Val Pro Ser Gly Ser Val Glu Gly Trp Val
                485                 490                 495

Trp Glu Leu Ala Lys Ala Tyr Val Ala Val Asn Asp Ser Gly Trp His
            500                 505                 510

Gln Leu Val Ser His Trp Leu Asn Thr His Ala Val Met Glu Pro Phe
        515                 520                 525

Val Ile Ser Thr Asn Arg His Leu Ser Val Thr His Pro Val His Lys
    530                 535                 540

Leu Leu Ser Pro His Tyr Arg Asp Thr Met Thr Ile Asn Ala Leu Ala
545                 550                 555                 560

Arg Gln Thr Leu Ile Asn Ala Gly Gly Ile Phe Glu Met Thr Val Phe
                565                 570                 575

Pro Gly Lys Phe Ala Leu Gly Met Ser Ala Val Val Tyr Lys Asp Trp
            580                 585                 590

Lys Phe Thr Glu Gln Gly Leu Pro Asp Asp Leu Ile Lys Arg Gly Met
        595                 600                 605

Ala Val Glu Asp Pro Ser Ser Pro Tyr Lys Val Arg Leu Leu Val Ser
    610                 615                 620

Asp Tyr Pro Tyr Ala Ala Asp Gly Leu Ala Ile Trp His Ala Ile Glu
625                 630                 635                 640

Gln Tyr Val Ser Glu Tyr Leu Ala Ile Tyr Tyr Pro Asn Asp Gly Val
                645                 650                 655

Leu Gln Gly Asp Thr Glu Val Gln Ala
            660                 665

<210> SEQ ID NO 5
<211> LENGTH: 4165
<212> TYPE: DNA
<213> ORGANISM: Hordeum vulgare cv. Neruda

<400> SEQUENCE: 5
atgctgctgg agggctgat cgacaccctc acggggcga acaagagcgc ccggctcaag      60
ggcacggtgg tgctcatgcg caagaacgtg ctggacctca cgacttcgg cgccaccatc    120 atcgacggca tcggcgagtt cctcggcaag ggcgtcacct gccagcttat cagctccacc    180
gccgtcgacc aaggtaatca ctaccctcct ccggccttct cctctgttta caagatatag    240
tatttctttc gtgtgggccg gcggccatgg atggatggat gtgtctggat cggctaaaga    300
agataggata gctagccctg gccggtcgtc tttacctgag catgggcata tgccatcgaa    360
aaaagagaca cagcatgca tgcatggtgc gcgcaccaga ccacgcagag caccggatgc    420
tcgagacaaa gcaacacaac aagcaaggac gacacgtcaa agcaacaca acaagcaagg    480 acggcacgtc aaaagcaaca caaacctaaa ctaaagcaca aagacgtaag agcaagcaca    540
caatcagcag gctataaaca gttgtcatca aaaacaacgc tggaagagag agagaaggaa    600
```

-continued

```
ggaagtagta gccatgaaaa attaaatcac cgggcgttgc tctttgccca acaattaatc      660
aagcaggata cgtggcatgt atagttcttg taagtaaact aagcatgtga tatgagaagg      720
tacgtggtgg tgcagacaac ggcggtcgcg ggaaggtggg cgcggaggcg gagctggagc      780
agtgggtgac gagcctgccg tcgctgacga cgggggagtc caagttcggc ctcaccttcg      840
actgggaggt ggagaagctc ggggtgccgg cgccatcgt cgtcaacaac taccacagct       900
ccgagttcct gcttaaaacc atcaccctcc acgacgtccc cggccgcagc ggcaacctca      960
ccttcgtcgc caactcatgg atctaccccg ccgccaacta ccgatacagc cgcgtcttct     1020
tcgccaacga cgtgcgtgga ttttcctcta ctttcctctc ctttcatttt caccgccttc     1080
gtcattcatg gtcgatcatt aagtcttgcc aggacaatag atgatgagct aggagtggtt     1140
accacttagc agtacgtaca ttatttattc cgtgttggta gaaaaggata tggtttggtg     1200
cagatcgaca caagattgaa tgaaagttgc accgtggcac cgtggcagcg tggtaggtga     1260
aaataactgt tgcacggatc cacccacatg attgttttca tgaataaact ttttaaggat     1320
gtgtctagcc acatctagat gcatgtcaca taattattgc ataccaaaac gattaaatta     1380
agcataaaaa gaaaaggaaa aaatactca catatctcga cgtaagatca atgatatagt      1440
atttagatat gcaatattta tcttacatct aaacctttct tcattcctaa atataagaca     1500
tttgtaagat ttcactatgg acaacatacg aaacaaaatc agtggatctc tctatgcatt     1560
cattatgtag tctataataa aatctttaaa agatcgtata ttttgcaacg gagggagtaa     1620
aacataactt tttaatagta atgttgcacg gctccacact cgcagacgta cctgccgagc     1680
cagatgccgg cggcgctgaa gccgtaccgc gacgacgagc tccggaacct gcgtggcgac     1740
gaccagcagg gcccgtacca ggagcacgac cgcatctacc gctacgacgt ctacaacgac     1800
ctcggcgagg gccgcccat cctcggcggc aactccgacc cccttaccc gcgccgcggc       1860 cgcacggagc gcaagcccaa cgccagcgac ccgagcctgg agagccggct gtcgctgctg     1920
gagcagatct acgtgccgcg ggacgagaag ttcggccacc tcaagacgtc cgacttcctg     1980
ggctactcca tcaaggccat cacgcagggc atcctgccgg ccgtgcgcac ctacgtggac     2040
accacccccg gcgagttcga ctccttccag gacatcatca acctctatga gggcggcatc     2100
aagctgccca aggtggccgc cctggaggag ctccgtaagc agttcccgct ccagctcatc     2160
aaggacctcc tccccgtcgg cggcgactcc ctgcttaagc tccccgtgcc ccacatcatc     2220
caggagaaca gcaggcgtg gaggaccgac gaggagttcg cacgggaggt gctcgccggc      2280
gtcaacccgg tcatgatcac gcgtctcacg gtgagtcagc gattatttgt tcattgtgtg     2340
tgtatggtgt ccatggtgag aaagtgcaga tcttgatttg cgttgggtcg catgcacgca     2400
tgctgcatgc atgcaggagt tcccgccaaa aagtagtctg gacccctagca gtttggtga    2460 ccacaccagc accatcacgg cggagcacat agagaagaac ctcgagggcc tcacggtgca    2520
gcaggtaatt ggtccaagcc atcgacatca actatgattt acctaggagt aattggtagc     2580
tgtagataat ttggcttcgt tgcaattaat ttgatgctgg ccgatcaagt gatcgtattg     2640
ggtttgaaat ttgcaggcgc tggaaagcaa caggctgtac atccttgatc accatgaccg     2700
gttcatgccg ttcctgatcg acgtcaacaa cctgcccggc aacttcatct acgccacgag     2760
gaccctcttc ttcctgcgcg cgacggcag gctcacgccg ctcgccatcg agctgagcga      2820
gcccatcatc cagggcggcc ttaccacggc caagagcaag gtttacacgc cggtgcccag     2880
cggctccgtc gaaggctggg tgtgggagct cgccaaggcc tacgtcgccg tcaatgactc     2940
cgggtggcac cagctcgtca gccactggta cgttctccac ggtcgatgtg attcagtcag    3000
```

-continued

```
tcgatgcaca acaactgatc gaaatatgat tgattgaaac gcgcaggctg aacactcacg    3060
cggtgatgga gccgttcgtg atctcgacga accggcacct tagcgtgacg cacccggtgc    3120
acaagctgct gagcccgcac taccgcgaca ccatgaccat caacgcgctg gcgcggcaga    3180
cgctcatcaa cgccggcggc atcttcgaga tgacggtgtt cccgggcaag ttcgcgttgg    3240
ggatgtcggc cgtggtgtac aaggactgga agttcaccga gcaggactg ccggacgatc     3300
tcatcaagag gtacgtacct ggtaaatgtt atgaatgtgt aaaacaaatt gggcgtctcg    3360
ctcactgaca ggaacgtggt aaaaaaaatg caggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc cgaacgacgg    3540
cgtgctgcag ggcgatacgg aggtgcaggc gtggtggaag gagacgcgcg aggtcgggca    3600
cggcgacctc aaggacgccc catggtggcc caagatgcaa agtgtgccgg agctggccaa    3660
ggcgtgcacc accatcatct ggatcgggtc ggcgctgcat gcggcagtca acttcgggca    3720
gtaccctac gcggggttcc tcccgaaccg gccgacggtg agccggcgcc gcatgccgga     3780
gcccggcacg gaggagtacg cggagctgga gcgcgaccg gagcgggcct tcatccacac     3840
catcacgagc cagatccaga ccatcatcgg cgtgtcgctg ctggaggtgc tgtcgaagca    3900
ctcctccgac gagctgtacc tcgggcagcg ggacacgccc gagtggacct cggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt ttccctacat    4080
gctgctctac cccaacacct ccgaccacaa gggcgccgct gccgggctta ccgccaaggg    4140
catccccaac agcatctcca tctaa                                          4165
```

<210> SEQ ID NO 6
<211> LENGTH: 4165
<212> TYPE: DNA
<213> ORGANISM: Hordeum vulgare mutant A618

<400> SEQUENCE: 6

```
atgctgctgg gagggctgat cgacaccctc acggggggcga acaagagcgc ccggctcaag    60
ggcacggtgg tgctcatgcg caagaacgtg ctggacctca cgacttcgg cgccaccatc     120
atcgacggca tcggcgagtt cctcggcaag ggcgtcacct gccagcttat cagctccacc    180
gccgtcgacc aagtaatca ctaccctcct ccggccttct cctctgttta caagatatag    240
tatttctttc gtgtgggccg gcggccatgg atggatggat gtgtctggat cggctaaaga    300
agataggata gctagccctg gccggtcgtc tttacctgag catgggcata tgccatcgaa    360
aaaagagaca acagcatgca tgcatggtgc gcgcaccaga ccacgcagag caccggatgc    420
tcgagacaaa gcaacacaac aagcaaggac gacacgtcaa aagcaacaca acaagcaagg    480
acggcacgtc aaaagcaaca caaacctaaa ctaaagcaca aagacgtaag agcaagcaca    540
caatcagcag gctataaaca gttgtcatca aaaacaacgc tggaagagag agagaaggaa    600
ggaagtagta gccatgaaaa attaaatcac cgggcgttgc tctttgccca acaattaatc    660
aagcaggata cgtggcatgt atagttcttg taagtaaact aagcatgtga tatgagaagg    720
tacgtggtgg tgcagacaac ggcggtcgcg ggaaggtggg cgcggaggcg agctggagc    780
agtgggtgac gagcctgccg tcgctgacga cgggggagtc caagttcggc ctcaccttcg    840
actgggaggt ggagaagctc ggggtgccgg gcgccatcgt cgtcaacaac taccacagct    900
```

```
ccgagttcct gcttaaaacc atcaccctcc acgacgtccc cggccgcagc ggcaacctca    960
ccttcgtcgc caactcatgg atctaccccg ccgccaacta ccgatacagc cgcgtcttct   1020
tcgccaacga cgtgcgtgga ttttcctcta ctttcctctc ctttcatttt caccgccttc   1080
gtcattcatg gtcgatcatt aagtcttgcc aggacaatag atgatgagct aggagtggtt   1140
accacttagc agtacgtaca ttatttattc cgtgttggta gaaaaggata tggtttggtg   1200
cagatcgaca caagattgaa tgaaagttgc accgtggcac cgtggcagcg tggtaggtga   1260
aaataactgt tgcacggatc cacccacatg attgttttca tgaataaact ttttaaggat   1320
gtgtctagcc acatctagat gcatgtcaca taattattgc ataccaaaac gattaaatta   1380
agcataaaaa gaaaggaaa aaaatactca catatctcga cgtaagatca atgatatagt   1440
atttagatat gcaatattta tcttacatct aaacctttct tcattcctaa atataagaca   1500
tttgtaagat ttcactatgg acaacatacg aaacaaaatc agtggatctc tctatgcatt   1560
cattatgtag tctataataa aatctttaaa agatcgtata ttttgcaacg agggagtaa    1620 aacataactt tttaatagta atgttgcacg gctccacact cgcagacgta cctgccgagc   1680
cagatgccgg cggcgctgaa gccgtaccgc gacgacgagc tccggaacct gcgtggcgac   1740
gaccagcagg gcccgtacca ggagcacgac cgcatctacc gctacgacgt ctacaacgac   1800
ctcggcgagg gccgccccat cctcggcggc aactccgacc accttaccc  gcgccgcggc   1860 cgcacggagc gcaagcccaa cgccagcgac ccgagcctgg agagccggct gtcgctgctg   1920
gagcagatct acgtgccgcg ggacgagaag ttcggccacc tcaagacgtc cgacttcctg   1980
ggctactcca tcaaggccat cacgcagggc atcctgccgg ccgtgcgcac ctacgtggac   2040 accaccccg gcgagttcga ctccttccag gacatcatca acctctatga gggcggcatc   2100
aagctgccca aggtggccgc cctggaggag ctccgtaagc agttcccgct ccagctcatc   2160
aaggacctcc tccccgtcgg cggcgactcc ctgcttaagc tccccgtgcc ccacatcatc   2220
caggagaaca agcaggcgtg gaggaccgac gaggagttcg cacgggaggt gctcgccggc   2280
gtcaacccgg tcatgatcac gcgtctcacg atgagtcagc gattatttgt tcattgtgtg   2340
tgtatggtgt ccatggtgag aaagtgcaga tcttgatttg cgttgggtcg catgcacgca   2400
tgctgcatgc atgcaggagt tcccgccaaa aagtagtctg gacccctagca agtttggtga   2460 ccacaccagc accatcacgg cggagcacat agagaagaac ctcgagggcc tcacggtgca   2520
gcaggtaatt ggtccaagcc atcgacatca actatgattt acctaggagt aattggtagc   2580
tgtagataat ttggcttcgt tgcaattaat ttgatgctgg ccgatcaagt gatcgtattg   2640
ggtttgaaat ttgcaggcgc tggaaagcaa caggctgtac atccttgatc accatgaccg   2700
gttcatgccg ttcctgatcg acgtcaacaa cctgcccggc aacttcatct acgccacgag   2760
gaccctcttc ttcctgcgcg cgacggcag gctcacgccg ctcgccatcg agctgagcga    2820
gcccatcatc cagggcggcc ttaccacggc caagagcaag gtttacacgc cggtgcccag   2880
cggctccgtc gaaggctggg tgtgggagct cgccaaggcc tacgtcgccg tcaatgactc   2940
cgggtggcac cagctcgtca gccactggta cgttctccac ggtcgatgtg attcagtcag   3000
tcgatgcaca acaactgatc gaaatatgat tgattgaaac gcgcaggctg aacactcacg   3060
cggtgatgga gccgttcgtg atctcgacga accggcacct tagcgtgacg cacccggtgc   3120
acaagctgct gagcccgcac taccgcgaca ccatgaccat caacgcgctg gcgcggcaga   3180
cgctcatcaa cgccggcggc atcttcgaga tgacggtgtt cccgggcaag ttcgcgttgg   3240
ggatgtcggc cgtggtgtac aaggactgga agttcaccga gcaggactg ccggacgatc    3300
```

-continued

```
tcatcaagag gtacgtacct ggtaaatgtt atgaatgtgt aaaacaaatt gggcgtctcg    3360
ctcactgaca ggaacgtggt aaaaaaaatg caggggcatg gcggtggagg acccgtcgag    3420
cccgtacaag gtgcggttgc tggtgtcgga ctacccgtac gcggcggacg ggctggcgat    3480
ctggcacgcc attgagcagt acgtgagcga gtacctggcc atctactacc cgaacgacgg    3540
cgtgctgcag ggcgatacgg aggtgcaggc gtggtggaag agacgcgcg aggtcgggca    3600 cggcgacctc aaggacgccc catggtggcc caagatgcaa agtgtgccgg agctggccaa    3660
ggcgtgcacc accatcatct ggatcgggtc ggcgctgcat cgcagtca acttcgggca     3720 gtaccctac gcggggttcc tcccgaaccg gccgacggtg agccggcgcc gcatgccgga    3780
gcccggcacg gaggagtacg cggagctgga gcgcgacccg gagcgggcct tcatccacac    3840
catcacgagc cagatccaga ccatcatcgg cgtgtcgctg ctggaggtgc tgtcgaagca    3900
ctcctccgac gagctgtacc tcgggcagcg ggacacgccg gagtggacct cggacccaaa    3960
ggccctggag gtgttcaagc ggttcagcga ccggctggtg gagatcgaga gcaaggtggt    4020
gggcatgaac catgacccgg agctcaagaa ccgcaacggc ccggctaagt ttccctacat    4080
gctgctctac cccaacacct ccgaccacaa gggcgccgct ccgggcttaa ccgccaaggg    4140
catccccaac agcatctcca tctaa                                          4165
```

<210> SEQ ID NO 7
<211> LENGTH: 862
<212> TYPE: PRT
<213> ORGANISM: Hordeum vulgare cv. Neruda

<400> SEQUENCE: 7

```
Met Leu Leu Gly Gly Leu Ile Asp Thr Leu Thr Gly Ala Asn Lys Ser
1               5                   10                  15

Ala Arg Leu Lys Gly Thr Val Val Leu Met Arg Lys Asn Val Leu Asp
            20                  25                  30

Leu Asn Asp Phe Gly Ala Thr Ile Ile Asp Gly Ile Gly Glu Phe Leu
        35                  40                  45

Gly Lys Gly Val Thr Cys Gln Leu Ile Ser Ser Thr Ala Val Asp Gln
    50                  55                  60

Asp Asn Gly Gly Arg Gly Lys Val Gly Ala Glu Ala Glu Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
            100                 105                 110

Val Val Asn Asn Tyr His Ser Ser Glu Phe Leu Leu Lys Thr Ile Thr
        115                 120                 125

Leu His Asp Val Pro Gly Arg Ser Gly Asn Leu Thr Phe Val Ala Asn
    130                 135                 140

Ser Trp Ile Tyr Pro Ala Ala Asn Tyr Arg Tyr Ser Arg Val Phe Phe
145                 150                 155                 160

Ala Asn Asp Thr Tyr Leu Pro Ser Gln Met Pro Ala Ala Leu Lys Pro
                165                 170                 175

Tyr Arg Asp Asp Glu Leu Arg Asn Leu Arg Gly Asp Asp Gln Gln Gly
            180                 185                 190

Pro Tyr Gln Glu His Asp Arg Ile Tyr Arg Tyr Asp Val Tyr Asn Asp
        195                 200                 205

Leu Gly Glu Gly Arg Pro Ile Leu Gly Gly Asn Ser Asp His Pro Tyr
```

-continued

```
            210                 215                 220
Pro Arg Arg Gly Arg Thr Glu Arg Lys Pro Asn Ala Ser Asp Pro Ser
225                 230                 235                 240

Leu Glu Ser Arg Leu Ser Leu Leu Glu Gln Ile Tyr Val Pro Arg Asp
            245                 250                 255

Glu Lys Phe Gly His Leu Lys Thr Ser Asp Phe Leu Gly Tyr Ser Ile
            260                 265                 270

Lys Ala Ile Thr Gln Gly Ile Leu Pro Ala Val Arg Thr Tyr Val Asp
            275                 280                 285

Thr Thr Pro Gly Glu Phe Asp Ser Phe Gln Asp Ile Ile Asn Leu Tyr
290                 295                 300

Glu Gly Gly Ile Lys Leu Pro Lys Val Ala Ala Leu Glu Glu Leu Arg
305                 310                 315                 320

Lys Gln Phe Pro Leu Gln Leu Ile Lys Asp Leu Leu Pro Val Gly Gly
            325                 330                 335

Asp Ser Leu Leu Lys Leu Pro Val Pro His Ile Ile Gln Glu Asn Lys
            340                 345                 350

Gln Ala Trp Arg Thr Asp Glu Glu Phe Ala Arg Glu Val Leu Ala Gly
            355                 360                 365

Val Asn Pro Val Met Ile Thr Arg Leu Thr Glu Phe Pro Pro Lys Ser
370                 375                 380

Ser Leu Asp Pro Ser Lys Phe Gly Asp His Thr Ser Thr Ile Thr Ala
385                 390                 395                 400

Glu His Ile Glu Lys Asn Leu Glu Gly Leu Thr Val Gln Gln Ala Leu
            405                 410                 415

Glu Ser Asn Arg Leu Tyr Ile Leu Asp His His Asp Arg Phe Met Pro
            420                 425                 430

Phe Leu Ile Asp Val Asn Asn Leu Pro Gly Asn Phe Ile Tyr Ala Thr
            435                 440                 445

Arg Thr Leu Phe Phe Leu Arg Gly Asp Gly Arg Leu Thr Pro Leu Ala
            450                 455                 460

Ile Glu Leu Ser Glu Pro Ile Ile Gln Gly Gly Leu Thr Thr Ala Lys
465                 470                 475                 480

Ser Lys Val Tyr Thr Pro Val Pro Ser Gly Ser Val Glu Gly Trp Val
            485                 490                 495

Trp Glu Leu Ala Lys Ala Tyr Val Ala Val Asn Asp Ser Gly Trp His
            500                 505                 510

Gln Leu Val Ser His Trp Leu Asn Thr His Ala Val Met Glu Pro Phe
            515                 520                 525

Val Ile Ser Thr Asn Arg His Leu Ser Val Thr His Pro Val His Lys
530                 535                 540

Leu Leu Ser Pro His Tyr Arg Asp Thr Met Thr Ile Asn Ala Leu Ala
545                 550                 555                 560

Arg Gln Thr Leu Ile Asn Ala Gly Gly Ile Phe Glu Met Thr Val Phe
            565                 570                 575

Pro Gly Lys Phe Ala Leu Gly Met Ser Ala Val Val Tyr Lys Asp Trp
            580                 585                 590

Lys Phe Thr Glu Gln Gly Leu Pro Asp Asp Leu Ile Lys Arg Gly Met
            595                 600                 605

Ala Val Glu Asp Pro Ser Ser Pro Tyr Lys Val Arg Leu Leu Val Ser
            610                 615                 620

Asp Tyr Pro Tyr Ala Ala Asp Gly Leu Ala Ile Trp His Ala Ile Glu
625                 630                 635                 640
```

```
Gln Tyr Val Ser Glu Tyr Leu Ala Ile Tyr Tyr Pro Asn Asp Gly Val
                645                 650                 655

Leu Gln Gly Asp Thr Glu Val Gln Ala Trp Trp Lys Glu Thr Arg Glu
            660                 665                 670

Val Gly His Gly Asp Leu Lys Asp Ala Pro Trp Trp Pro Lys Met Gln
        675                 680                 685

Ser Val Pro Glu Leu Ala Lys Ala Cys Thr Thr Ile Ile Trp Ile Gly
    690                 695                 700

Ser Ala Leu His Ala Ala Val Asn Phe Gly Gln Tyr Pro Tyr Ala Gly
705                 710                 715                 720

Phe Leu Pro Asn Arg Pro Thr Val Ser Arg Arg Met Pro Glu Pro
                725                 730                 735

Gly Thr Glu Glu Tyr Ala Glu Leu Arg Asp Pro Glu Arg Ala Phe
            740                 745                 750

Ile His Thr Ile Thr Ser Gln Ile Gln Thr Ile Ile Gly Val Ser Leu
        755                 760                 765

Leu Glu Val Leu Ser Lys His Ser Ser Asp Glu Leu Tyr Leu Gly Gln
    770                 775                 780

Arg Asp Thr Pro Glu Trp Thr Ser Asp Pro Lys Ala Leu Glu Val Phe
785                 790                 795                 800

Lys Arg Phe Ser Asp Arg Leu Val Glu Ile Glu Ser Lys Val Val Gly
                805                 810                 815

Met Asn His Asp Pro Glu Leu Lys Asn Arg Asn Gly Pro Ala Lys Phe
            820                 825                 830

Pro Tyr Met Leu Leu Tyr Pro Asn Thr Ser Asp His Lys Gly Ala Ala
        835                 840                 845

Ala Gly Leu Thr Ala Lys Gly Ile Pro Asn Ser Ile Ser Ile
    850                 855                 860

<210> SEQ ID NO 8
<211> LENGTH: 399
<212> TYPE: PRT
<213> ORGANISM: Hordeum vulgare mutant A618

<400> SEQUENCE: 8

Met Leu Leu Gly Gly Leu Ile Asp Thr Leu Thr Gly Ala Asn Lys Ser
1               5                   10                  15

Ala Arg Leu Lys Gly Thr Val Val Leu Met Arg Lys Asn Val Leu Asp
                20                  25                  30

Leu Asn Asp Phe Gly Ala Thr Ile Ile Asp Gly Ile Gly Glu Phe Leu
            35                  40                  45

Gly Lys Gly Val Thr Cys Gln Leu Ile Ser Ser Thr Ala Val Asp Gln
        50                  55                  60

Asp Asn Gly Gly Arg Gly Lys Val Gly Ala Glu Ala Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
            100                 105                 110

Val Val Asn Asn Tyr His Ser Ser Glu Phe Leu Leu Lys Thr Ile Thr
        115                 120                 125

Leu His Asp Val Pro Gly Arg Ser Gly Asn Leu Thr Phe Val Ala Asn
    130                 135                 140

Ser Trp Ile Tyr Pro Ala Ala Asn Tyr Arg Tyr Ser Arg Val Phe Phe
```

```
                145                 150                 155                 160
Ala Asn Asp Thr Tyr Leu Pro Ser Gln Met Pro Ala Ala Leu Lys Pro
                165                 170                 175

Tyr Arg Asp Asp Glu Leu Arg Asn Leu Arg Gly Asp Asp Gln Gln Gly
            180                 185                 190

Pro Tyr Gln Glu His Asp Arg Ile Tyr Arg Tyr Asp Val Tyr Asn Asp
        195                 200                 205

Leu Gly Glu Gly Arg Pro Ile Leu Gly Gly Asn Ser Asp His Pro Tyr
    210                 215                 220

Pro Arg Arg Gly Arg Thr Glu Arg Lys Pro Asn Ala Ser Asp Pro Ser
225                 230                 235                 240

Leu Glu Ser Arg Leu Ser Leu Leu Glu Gln Ile Tyr Val Pro Arg Asp
                245                 250                 255

Glu Lys Phe Gly His Leu Lys Thr Ser Asp Phe Leu Gly Tyr Ser Ile
            260                 265                 270

Lys Ala Ile Thr Gln Gly Ile Leu Pro Ala Val Arg Thr Tyr Val Asp
        275                 280                 285

Thr Thr Pro Gly Glu Phe Asp Ser Phe Gln Asp Ile Ile Asn Leu Tyr
    290                 295                 300

Glu Gly Gly Ile Lys Leu Pro Lys Val Ala Ala Leu Glu Glu Leu Arg
305                 310                 315                 320

Lys Gln Phe Pro Leu Gln Leu Ile Lys Asp Leu Leu Pro Val Gly Gly
                325                 330                 335

Asp Ser Leu Leu Lys Leu Pro Val Pro His Ile Ile Gln Glu Asn Lys
            340                 345                 350

Gln Ala Trp Arg Thr Asp Glu Glu Phe Ala Arg Glu Val Leu Ala Gly
        355                 360                 365

Val Asn Pro Val Met Ile Thr Arg Leu Thr Met Ser Gln Arg Leu Phe
    370                 375                 380

Val His Cys Val Cys Met Val Ser Met Val Arg Lys Cys Arg Ser
385                 390                 395

<210> SEQ ID NO 9
<211> LENGTH: 28
<212> TYPE: DNA
<213> ORGANISM: Artificial Sequence
<220> FEATURE:
<223> OTHER INFORMATION: Oligonucleotide

<400> SEQUENCE: 9
gaaagcgagg agaggaggcc aagaacaa                                          28

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide

<400> SEQUENCE: 10
ttattcatcc atggttgccg atggcttaga                                        30

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide
```

```
<400> SEQUENCE: 11
agggactgcc ggacgatctc a                                              21

<210> SEQ ID NO 12
<211> LENGTH: 18
<212> TYPE: DNA
<213> ORGANISM: Artificial Sequence
<220> FEATURE:
<223> OTHER INFORMATION: Oligonucletide

<400> SEQUENCE: 12
gccagctccg gcacactt                                                  18

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide

<400> SEQUENCE: 13
caaggtgcgg ttgctggtgt c                                              21

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide

<400> SEQUENCE: 14
ctcgcgcgtc tccttccac                                                 19

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide

<400> SEQUENCE: 15
ctcgcgcgtc tccttccat                                                 19

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
tacgtgccgc gggacgagaa g                                              21

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide

<400> SEQUENCE: 17
tgatcatgac cgggttgacg t                                              21

<210> SEQ ID NO 18
<211> LENGTH: 21
```

```
<212> TYPE: DNA
<213> ORGANISM: Artificial Sequence
<220> FEATURE:
<223> OTHER INFORMATION: Oligonucleotide

<400> SEQUENCE: 18
catatgctgc tgggagggct g                                              21

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide

<400> SEQUENCE: 19
gaattcttag atggagatgc tgttggg                                        27

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide

<400> SEQUENCE: 20
ctacccgtac gcggcggacg ggct                                           24

<210> SEQ ID NO 21
<211> LENGTH: 31
<212> TYPE: DNA
<213> ORGANISM: Artificial Sequence
<220> FEATURE:
<223> OTHER INFORMATION: Oligonucleotide

<400> SEQUENCE: 21
tcctgaattc acgcctgcac ctccgtatcg c                                   31
```